US012799082B2

(12) United States Patent
Yu et al.

(10) Patent No.: US 12,799,082 B2
(45) Date of Patent: Nov. 17, 2026

(54) QUINAZOLINE DERIVATIVES USEFUL AS SELECTIVE HDAC6 INHIBITORS

(71) Applicant: AnnJi Pharmaceutical Co., Ltd., Taipei (TW)

(72) Inventors: Chao-Wu Yu, New Taipei (TW); Pei-Yun Hung, Taipei (TW); Ajit Dhananjay Jagtap, Taipei (TW); Yi-Hsun Ho, Kaohsiung (TW); Hsin-Yi Chiang, New Taipei (TW)

(73) Assignee: AnnJi Pharmaceutical Co., Ltd., Taipei City (TW)

( * ) Notice: Subject to any disclaimer, the term of this patent is extended or adjusted under 35 U.S.C. 154(b) by 685 days.

(21) Appl. No.: 18/001,002

(22) PCT Filed: Jun. 8, 2021

(86) PCT No.: PCT/US2021/036375

§ 371 (c)(1),
(2) Date: Dec. 7, 2022

(87) PCT Pub. No.: WO2021/252475

PCT Pub. Date: Dec. 16, 2021

(65) Prior Publication Data

US 2023/0212129 A1 Jul. 6, 2023

Related U.S. Application Data

(60) Provisional application No. 63/036,282, filed on Jun. 8, 2020.

(51) Int. Cl.

*C07D 239/91* (2006.01)
*A61P 11/00* (2006.01)
*A61P 25/02* (2006.01)

(52) U.S. Cl.

CPC ............ *C07D 239/91* (2013.01); *A61P 11/00* (2018.01); *A61P 25/02* (2018.01)

(58) Field of Classification Search

CPC ........ C07D 239/91; A61P 11/00; A61P 25/02; A61P 43/00; A61K 31/517

See application file for complete search history.

(56) References Cited

U.S. PATENT DOCUMENTS 9,387,209 B2 * 7/2016 Chern ..................... A61P 15/00
2016/0304456 A1 * 10/2016 Ng ....................... C07D 401/04

FOREIGN PATENT DOCUMENTS

WO WO-2013/154870 A1 10/2013
WO WO-2021/252475 A1 12/2021

OTHER PUBLICATIONS

Porter et al. (J. Med. Chem. 2018, 61, 8054-8060).*
Yang et al. (Bioorg. Med. Chem. 22 (2014) 6146-6155).*
Yu et al., "Quinazolin-4-one Derivatives as Selective Histone Deacetylase-6 Inhibitors for the Treatment of Alzheimer's Disease," Journal of Medicinal Chemistry, 2013, 56:6775-6791.
Van Beneden et al., "HDAC inhibitors in experimental liver and kidney fibrosis" Fibrogenesis & Tissue Repair, Biomed Central Ltd, vol. 6, No. 1, Jan. 2, 2013; pp. 1-14, DOI: 10.1186/1755-1536-6-1.
International Search Report and Written Opinion for PCT/US2021/036375 mailed Aug. 23, 2021.

* cited by examiner

*Primary Examiner* — Robert H Havlin
(74) *Attorney, Agent, or Firm* — Goodwin Procter LLP

(57) ABSTRACT

Provided herein is a compound of Formula (I): or a pharmaceutically acceptable salt thereof, wherein the variables are defined herein. Also provided herein are pharmaceutical compositions comprising a compound of Formula (I) and methods of using the compounds, e.g., in the treatment of neuropathy-related disorders and fibrotic diseases.

(I)

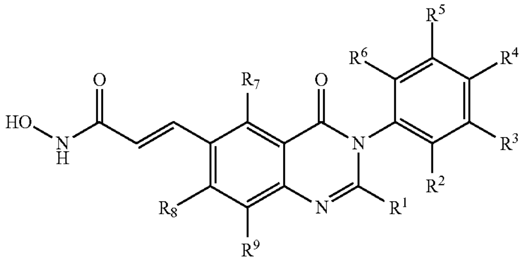

17 Claims, 7 Drawing Sheets

QUINAZOLINE DERIVATIVES USEFUL AS SELECTIVE HDAC6 INHIBITORS

RELATED APPLICATIONS

This application is a U.S. National Phase Application under 35 U.S.C. § 371 of International Patent Application No. PCT/US2021/036375, filed Jun. 8, 2021, which claims priority to and the benefit of U.S. Provisional Patent Application No. 63/036,282 filed Jun. 8, 2020, each of which is incorporated by reference in its entirety.

BACKGROUND OF THE INVENTION

WO2008040934, WO2008068170, WO2008087514, WO2009026446, WO2009045440, WO2011011186, WO2013154870, U.S. Pat. Nos. 8,188,138, 8,058,273, 7,803,800, 9,387,209, and 9,155,739 disclose histone deacetylases (HDACs) inhibitors having activities in antitumor activities and antineurodegenerative activities.

Histones play a critical role in transcriptional regulation, cell cycle progression, and developmental events. Histone acetylation/deacetylation alters chromatin structure and affects transcription. Histone deacetylase 6 (HDAC6) is a cytoplasmic class II histone deacetylase (HDAC) that, in contrast to the other HDACs, has a specificity for non-histone proteins, including α-tubulin. HDAC6 regulates multiple intracellular processes, such as protein degradation, cell motility, and cell-cell interaction. HDAC6 has been implicated in the regulation of mitochondrial transport. HDAC6 inhibition could increase α-tubulin acetylation and promote mitochondrial transport in hippocampal neurons.

Peripheral neuropathies are a heterogeneous group of diseases that are characterized by a progressive, ascending loss of nerve function arising from the peripheral regions of the limbs. The phenotypic overlap between different types of hereditary and acquired peripheral neuropathies indicates that similar pathophysiological processes are at play. Many downstream pathways in peripheral neurons, such as axonal transport, protein degradation, and interactions with Schwann cells, organelle damage, channelopathies, and neuroinflammatory signaling, have been proposed and each affects peripheral nerves in a negative way. Histone deacetylase 6 (HDAC6) plays an important role at the intersection of these converging pathogenic pathways. The enzymatic deacetylase activity of HDAC6 is upregulated in neurodegenerative disorders and typically results in downstream neuronal stress.

New and improved compounds are needed that act as inhibitors of HDAC6, as well as agents for the prevention and treatment of neuropathy-related diseases. The compounds, compositions, and methods described herein are directed toward this end.

SUMMARY OF THE INVENTION

Figure 1:
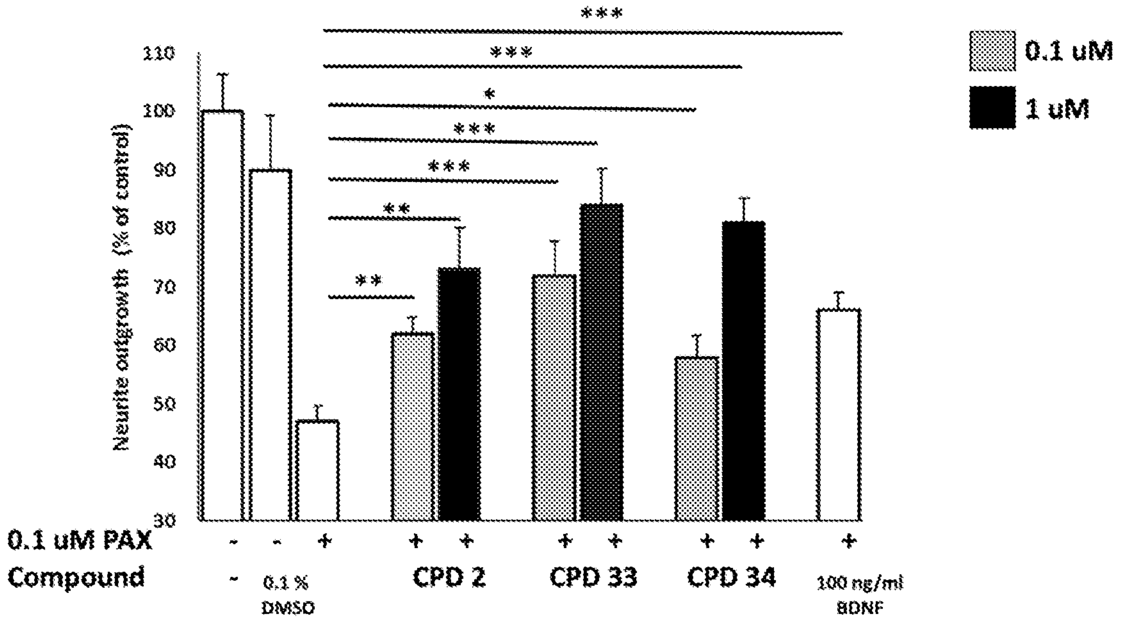
FIG. 1 depicts the Neurite outgrowth (% of control) for HDAC6 inhibitors.

In an aspect, provided herein is a compound of Formula (I):

Formula (I)

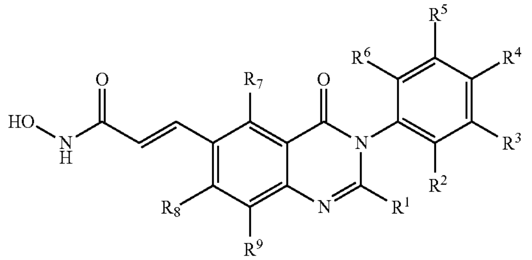

or a pharmaceutically acceptable salt thereof, wherein $R^1$ is $(C_{1-2})$alkyl, or fluoro$(C_{1-2})$alkyl; $R^2$ is hydrogen, halogen, or $(C_{1-3})$alkyl; $R^3$ is hydrogen, or $(C_{1-3})$alkyl; $R^4$ is hydrogen, halogen, $(C_{1-3})$alkyl, or methoxy, $R^5$ is hydrogen, $(C_{1-3})$ alkyl, halogen, or trifluoromethyl; $R^6$ is hydrogen, $(C_{1-3})$ alkyl, halogen; $R^7$ is hydrogen or halogen; $R^8$ is hydrogen, methyl, methoxy, or fluoro; and $R^9$ is hydrogen or fluoro.

In some aspects, $R^1$ is methyl. In other aspects, $R^1$ is ethyl. In some embodiments $R^2$ is hydrogen, whereas in other embodiments $R^2$ is halogen. In certain embodiments $R^2$ is methyl. In other embodiments $R^3$ is hydrogen. In further embodiments $R^6$ is methyl.

In further aspects, the compound is of Formula (IA)

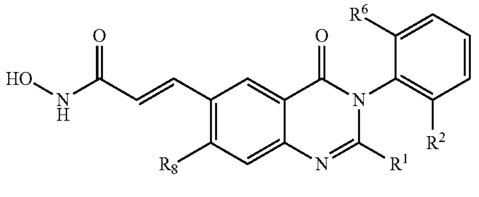

.

In other embodiments, the compound is of Formula (IB)

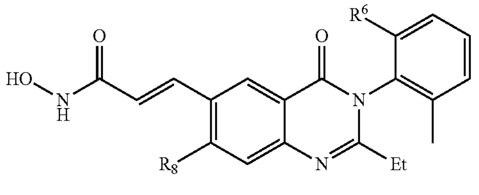

, wherein $R^8$ is fluoro.

In some embodiments, the compound is selected from Table 1.

In an aspect, provided herein is a compound of Formula (II):

Formula (II)

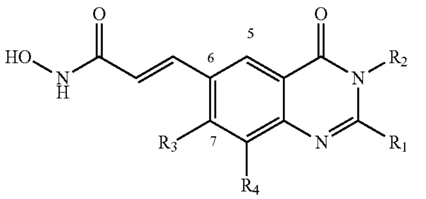

or a pharmaceutically acceptable salt thereof, wherein $R^1$ is methyl, ethyl, or fluoro($C_{1-2}$)alkyl; $R^2$ is phenyl or phenyl substituted with 1 to 3 substituents independently selected from the group consisting of methyl, ethyl, methoxy, trifluoromethyl, and halogen; $R^3$ is hydrogen, methyl, methoxy, or fluoro; and $R^4$ is hydrogen or fluoro.

In one aspect, provided herein is a pharmaceutical compositions comprising a therapeutically effective amount of the selective HDAC6 inhibitor (HDAC6i) of a compound disclosed herein, or a pharmaceutically acceptable salt thereof, and a pharmaceutically acceptable carrier or vehicle.

In some embodiments, a method for the prevention or treatment of chemotherapy-induced peripheral neuropathy in a subject, wherein said subject is administered with effective amount of the selective HDAC6 inhibitor disclosed herein, or a pharmaceutically acceptable salt, and a pharmaceutically acceptable carrier or vehicle. In other embodiments, the said chemotherapy is platinum-based chemotherapy, alkaloid-based, or taxane-based chemotherapy.

In some aspects, a method for enhancing tubulin hyperacetylation of cells in a subject, wherein said subject is treated with effective amount of the selective HDAC6 inhibitor disclosed herein, or a pharmaceutically acceptable salt thereof, and a pharmaceutically acceptable carrier or vehicle.

In other embodiments, a method for the prevention or treatment of fibrosis of a subject, wherein said subject is administered with effective amount of the selective HDAC6 inhibitor disclosed herein, or a pharmaceutically acceptable salt, and a pharmaceutically acceptable carrier or vehicle. In further embodiments, said fibrosis is pulmonary fibrosis, hepatic fibrosis, or renal fibrosis, wherein said pulmonary fibrosis is associated with increased expression of IL-6 in said subject. In other embodiments, said pulmonary fibrosis is idiopathic pulmonary fibrosis or virus-induced fibrosis.

In some aspects, a method of decreasing expression of IL-6 in a subject in need, wherein said subject is administered with effective amount of the selective HDAC6 inhibitor disclosed herein, or a pharmaceutically acceptable salt, and a pharmaceutically acceptable carrier or vehicle.

In further embodiments, a method of treating or ameliorating cytokine-induced inflammatory conditions in a subject in need, wherein said cytokine comprises IL-6, M-CSF, VCAM-1, MCP-1 tPA, MMP-1, MMP9, collagen 1 and collagen III, and said subject is administered with effective amount of the selective HDAC6 inhibitor disclosed herein, or a pharmaceutically acceptable salt, and a pharmaceutically acceptable carrier or vehicle. In other embodiments, said conditions are selected from a group consisting of pulmonary fibrosis, coronavirus-induced pulmonary inflammation, liver fibrosis, and renal fibrosis.

In some embodiments, use of the selective HDAC6 inhibitor disclosed herein in the manufacture of a medicament for the prevention or treatment of chemotherapy-induced peripheral neuropathy in a subject in need thereof.

In other embodiments, use of the selective HDAC6 inhibitor disclosed herein in the manufacture of a medicament for the prevention or treatment of fibrosis in a subject in need thereof In further embodiments, use of the selective HDAC6 inhibitor disclosed herein in the manufacture of a medicament for the treatment of pulmonary fibrosis, coronavirus-induced pulmonary inflammation, liver fibrosis, and renal fibrosis.

In some embodiments, a method for the prevention or treatment of diabetes induced neuropathy in a subject, wherein said subject is administered with effective amount of the selective HDAC6 inhibitor of disclosed herein or a pharmaceutically acceptable salt, and a pharmaceutically acceptable carrier or vehicle.

DETAILED DESCRIPTION OF CERTAIN EMBODIMENTS OF THE INVENTION

As generally described herein, the present invention provides compounds designed, for example, to act as histone deacetylases (HDACs) inhibitors, e.g. inhibitors of HDAC6. In certain embodiments, such compounds are envisioned to be useful as therapeutic agents for treating diabetic induced neuropathy, for example diabetic peripheral neuropathy. In other embodiments, such compounds are envisioned to be useful as therapeutic agents for treating chemotherapy-induced neuropathy, e.g. chemotherapy-induced peripheral neuropathy.

Definitions

Chemical Definitions

Definitions of specific functional groups and chemical terms are described in more detail below. The chemical elements are identified in accordance with the Periodic Table of the Elements, CAS version, *Handbook of Chemistry and Physics,* 75*th* Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry,* 5*th* Edition, John Wiley & Sons, Inc., New York, 2001; Larock, *Comprehensive Organic Transformations*, VCH Publishers, Inc., New York, 1989; and Carruthers, *Some Modern Methods of Organic Synthesis,* 3*rd* Edition, Cambridge University Press, Cambridge, 1987.

Isomers, e.g., stereoisomers, can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E.L. Eliel, Ed., Univ. of Notre Dame Press, Notre Dame, IN 1972). The invention additionally encompasses compounds described herein as individual isomers substantially free of other isomers, and alternatively, as mixtures of various isomers.

"Stereoisomers": It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

In the compositions provided herein, an enantiomerically pure compound can be present with other active or inactive ingredients. For example, a pharmaceutical composition comprising enantiomerically pure R-position/center/carbon compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

The term "diastereomerically pure" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of a single diastereomer. Methods for determining diastereomeric and enantiomeric purity are well-known in the art. Diastereomeric purity can be determined by any analytical method capable of quantitatively distinguishing between a compound and its diastereomers, such as high performance liquid chromatography (HPLC).

The articles "a" and "an" may be used herein to refer to one or to more than one (i.e. at least one) of the grammatical objects of the article. By way of example "an analogue" means one analogue or more than one analogue.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_1$-2, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The following terms are intended to have the meanings presented therewith below and are useful in understanding the description and intended scope of the present invention.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-4}$ alkyl", also referred to herein as "lower alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl (C), 3-pentanyl (C), amyl (C), neopentyl (C), 3-methyl-2-butanyl (C), tertiary amyl (C), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., $—CH_3$). In certain embodiments, the alkyl group is substituted $C_{1-10}$ alkyl. Common alkyl abbreviations include Me ($—CH_3$), Et ($—CH_2CH_3$), iPr ($—CH(CH_3)_2$), nPr ($—CH_2CH_2CH_3$), n-Bu ($—CH_2CH_2CH_2CH_3$), or i-Bu ($—CH_2CH(CH_3)_2$).

"Alkylene" refers to an alkyl group wherein two hydrogens are removed to provide a divalent radical, and which may be substituted or unsubstituted. Unsubstituted alkylene groups include, but are not limited to, methylene ($—CH_2—$), ethylene ($—CH_2CH_2—$), propylene ($—CH_2CH_2CH_2—$), butylene ($—CH_2CH_2CH_2CH_2—$), pentylene ($—CH_2CH_2CH_2CH_2CH_2—$), hexylene (—$CH_2CH_2CH_2CH_2CH_2CH_2$—), and the like. Exemplary substituted alkylene groups, e.g., substituted with one or more alkyl (methyl) groups, include but are not limited to, substituted methylene (—$CH(CH_3)$—, (—$C(CH_3)_2$—), substituted ethylene (—$CH(CH_3)CH_2$—, —$CH_2CH(CH_3)$—, —$C(CH_3)_2CH_2$—, —$CH_2C(CH_3)_2$—), substituted propylene (—$CH(CH_3)CH_2CH_2$—, —$CH_2CH(CH_3)CH_2$—, —$CH_2CH_2CH(CH_3)$—, —$C(CH_3)_2CH_2CH_2$—, —$CH_2C(CH_3)_2CH_2$—, —$CH_2CH_2C(CH_3)_2$—), and the like. When a range or number of carbons is provided for a particular alkylene group, it is understood that the range or number refers to the range or number of carbons in the linear carbon divalent chain. Alkylene groups may be substituted or unsubstituted with one or more substituents as described herein.

"Alkenyl" refers to a radical of a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("$C_{2-20}$ alkenyl"). In certain embodiments, alkenyl does not contain any triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds (e.g., 1, 2, 3, or 4 carbon-carbon triple bonds), and optionally one or more carbon-carbon double bonds (e.g., 1, 2, 3, or 4 carbon-carbon double bonds) ("$C_{2-20}$ alkynyl"). In certain embodiments, alkynyl does not contain any double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents; e.g., for instance from 1 to 5 substituents, 1 to 3 substituents, or 1 substituent. In certain embodiments, the alkynyl group is unsubstituted $C_{2-10}$ alkynyl. In certain embodiments, the alkynyl group is substituted $C_{2-10}$ alkynyl.

The term "heteroalkyl," as used herein, refers to an alkyl group, as defined herein, which further comprises 1 or more (e.g., 1, 2, 3, or 4) heteroatoms (e.g., oxygen, sulfur, nitrogen, boron, silicon, phosphorus) within the parent chain, wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkyl group refers to a saturated group having from 1 to 10 carbon atoms and 1, 2, 3, or 4 heteroatoms ("hetero$C_{1-10}$ alkyl"). In some embodiments, a heteroalkyl group is a saturated group having 1 to 9 carbon atoms and 1, 2, 3, or 4 heteroatoms ("hetero$C_{1-9}$ alkyl"). In some embodiments, a heteroalkyl group is a saturated group having 1 to 8 carbon atoms and 1, 2, 3, or 4 heteroatoms ("hetero$C_{1-8}$ alkyl"). In some embodiments, a heteroalkyl group is a saturated group having 1 to 7 carbon atoms and 1, 2, 3, or 4 heteroatoms ("hetero$C_{1-7}$ alkyl"). In some embodiments, a heteroalkyl group is a group having 1 to 6 carbon atoms and 1, 2, or 3 heteroatoms ("hetero$C_{1-6}$ alkyl"). In some embodiments, a heteroalkyl group is a saturated group having 1 to 5 carbon atoms and 1 or 2 heteroatoms ("hetero$C_{1-5}$ alkyl"). In some embodiments, a heteroalkyl group is a saturated group having 1 to 4 carbon atoms and lor 2 heteroatoms ("hetero$C_{1-4}$ alkyl"). In some embodiments, a heteroalkyl group is a saturated group having 1 to 3 carbon atoms and 1 heteroatom ("hetero$C_{1-3}$ alkyl"). In some embodiments, a heteroalkyl group is a saturated group having 1 to 2 carbon atoms and 1 heteroatom ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

"Aryl" refers to a radical of a monocyclic or polycyclic (e.g., bicyclic or tricyclic) 4n+2 aromatic ring system (e.g., having 6, 10, or 14 n electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

In certain embodiments, an aryl group substituted with one or more of groups selected from halo, $C_1$-$C_8$ alkyl, $C_1$-$C_8$ haloalkyl, cyano, hydroxy, $C_1$-$C_8$ alkoxy, and amino.

Examples of representative substituted aryls include the following

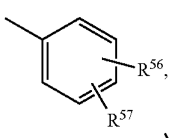

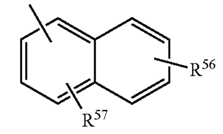

and

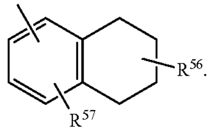

wherein one of $R^{56}$ and $R^{57}$ may be hydrogen and at least one of $R^{56}$ and $R^{57}$ is each independently selected from $C_1$-$C_8$ alkyl, $C_1$-$C_8$ haloalkyl, 4-10 membered heterocyclyl, alkanoyl, $C_1$-$C_8$ alkoxy, heteroaryloxy, alkylamino, arylamino, heteroarylamino, $NR^{58}COR^{59}$, $NR^{58}SOR^{59}NR^{58}SO_2R^{59}$, COOalkyl, COOaryl, $CONR^{58}R^{59}$, $CONR^{58}OR^{59}$, $NR^{58}R^{59}$, $SO_2NR^{58}R^{59}$, S-alkyl, SOalkyl, $SO_2$alkyl, Saryl, SOaryl, $SO_2$aryl; or $R^{56}$ and $R^{57}$ may be joined to form a cyclic ring (saturated or unsaturated) from 5 to 8 atoms, optionally containing one or more heteroatoms selected from the group N, O, or S. $R^{60}$ and $R^{61}$ are independently hydrogen, $C_1$-$C_8$ alkyl, $C_1$-$C_4$haloalkyl, $C_3$-$C_{10}$ cycloalkyl, 4-10 membered heterocyclyl, $C_6$-$C_{10}$ aryl, substituted $C_6$-$C_{10}$ aryl, 5-10 membered heteroaryl, or substituted 5-10 membered heteroaryl.

"Fused aryl" refers to an aryl having two of its ring carbon in common with a second aryl or heteroaryl ring or with a carbocyclyl or heterocyclyl ring.

"Heteroaryl" refers to a radical of a 5-10 membered monocyclic or bicyclic 4n+2 aromatic ring system (e.g., having 6 or 10 $\pi$ electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following:

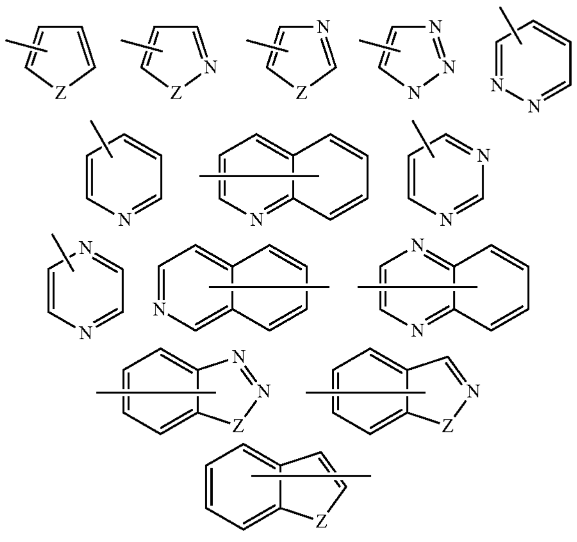

wherein each Z is selected from carbonyl, N, $NR^{65}$, O, and S; and $R^{65}$ is independently hydrogen, $C_1$-$C_8$ alkyl, $C_3$-$C_{10}$ cycloalkyl, 4-10 membered heterocyclyl, $C_6$-$C_{10}$ aryl, and 5-10 membered heteroaryl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl (C), cyclopentenyl (C), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Nitrogen-containing heterocyclyl" group means a 4- to 7-membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl, cycloalkyl, e.g., heterocyclyl, aryl, e.g., heteroaryl, cycloalkenyl, e.g., cycloheteroalkenyl, and the like having from 1 to 5, and particularly from 1 to 3 heteroatoms.

"Acyl" refers to a radical —C(O)$R^{20}$, where $R^{20}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. "Alkanoyl" is an acyl group wherein $R^{20}$ is a group other than hydrogen. Representative acyl groups include, but are not limited to, formyl (—CHO), acetyl (—C(═O)$CH_3$), cyclohexylcarbonyl, cyclohexylmethylcarbonyl, benzoyl (—C(═O)Ph), benzylcarbonyl (—C(═O)$CH_2$Ph), C(O)—$C_1$-$C_8$ alkyl, —C(O)—$(CH_2)_t$($C_6$-$C_{10}$ aryl), —C(O)—$(CH_2)_t$(5-10 membered heteroaryl), —C(O)—$(CH_2)_t$($C_3$-$C_{10}$ cycloalkyl), and —C(O)—$(CH_2)_t$(4-10 membered heterocyclyl), wherein t is an integer from 0 to 4. In certain embodiments, $R^{21}$ is $C_1$-$C_8$ alkyl, substituted with halo or hydroxy; or $C_3$-$C_{10}$ cycloalkyl, 4-10 membered heterocyclyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

"Alkoxy" refers to the group —$OR^{29}$ where $R^{29}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

In certain embodiments, $R^{29}$ is a group that has 1 or more substituents, for instance from 1 to 5 substituents, and particularly from 1 to 3 substituents, in particular 1 substituent, selected from the group consisting of amino, substituted amino, $C_6$-$C_{10}$ aryl, aryloxy, carboxyl, cyano, $C_3$-$C_{10}$ cycloalkyl, 4-10 membered heterocyclyl, halogen, 5-10 membered heteroaryl, hydroxyl, nitro, thioalkoxy, thioaryloxy, thiol, alkyl-S(O)—, aryl-S(O)—, alkyl-$S(O)_2$— and aryl-$S(O)_2$—. Exemplary 'substituted alkoxy' groups include, but are not limited to, —O—$(CH_2)_t$($C_6$-$C_{10}$ aryl), —O—$(CH_2)_t$(5-10 membered heteroaryl), —O—$(CH_2)_t$($C_3$-$C_{10}$ cycloalkyl), and —O—$(CH_2)_t$(4-10 membered heterocyclyl), wherein t is an integer from 0 to 4 and any aryl, heteroaryl, cycloalkyl or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Particular exemplary 'substituted alkoxy' groups are —$OCF_3$, —$OCH_2CF_3$, —$OCH_2$Ph, —$OCH_2$-cyclopropyl, —$OCH_2CH_2OH$, and —$OCH_2CH_2NMe_2$.

"Amino" refers to the radical —$NH_2$.

"Oxo group" refers to —C(═O)—.

"Substituted amino" refers to an amino group of the formula —$N(R^{38})_2$ wherein $R^{38}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of $R^{38}$ is not a hydrogen. In certain embodiments, each $R^{38}$ is independently selected from hydrogen, $C_1$-$C_8$ alkyl, $C_3$-$C_8$ alkenyl, $C_3$-$C_8$ alkynyl, $C_6$-$C_{10}$ aryl, 5-10 membered heteroaryl, 4-10 membered heterocyclyl, or $C_3$-$C_{10}$ cycloalkyl; or $C_1$-$C_8$ alkyl, substituted with halo or hydroxy; $C_3$-$C_8$ alkenyl, substituted with halo or hydroxy; $C_3$-$C_8$ alkynyl, substituted with halo or hydroxy, or —$(CH_2)_t$($C_6$-$C_{10}$ aryl), —$(CH_2)_t$(5-10 membered heteroaryl), —$(CH_2)_t$($C_3$-$C_{10}$ cycloalkyl), or —$(CH_2)_t$(4-10 membered heterocyclyl), wherein t is an integer between 0 and 8, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; or both $R^{38}$ groups are joined to form an alkylene group.

Exemplary "substituted amino" groups include, but are not limited to, —$NR^{39}$—$C_1$-$C_8$ alkyl, —$NR^{39}$—$(CH_2)_t$($C_6$-$C_{10}$ aryl), —$NR^{39}$—$(CH_2)_t$(5-10 membered heteroaryl), —$NR^{39}$—$(CH_2)_t$($C_3$-$C_{10}$ cycloalkyl), and —$NR^{39}$—$(CH_2)_t$(4-10 membered heterocyclyl), wherein t is an integer from 0 to 4, for instance 1 or 2, each $R^{39}$ independently represents H or $C_1$-$C_8$ alkyl; and any alkyl groups present, may themselves be substituted by halo, substituted or unsubstituted amino, or hydroxy; and any aryl, heteroaryl, cycloalkyl, or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. For the avoidance of doubt the term 'substituted amino' includes the groups alkylamino, substituted alkylamino, alkylarylamino, substituted alkylarylamino, arylamino, substituted arylamino, dialkylamino, and substituted dialkylamino as defined below. Substituted amino encompasses both monosubstituted amino and disubstituted amino groups.

"Carboxy" refers to the radical —C(O)OH.

"Cyano" refers to the radical —CN.

"Halo" or "halogen" refers to fluoro (F), chloro ($C_1$), bromo (Br), and iodo (I). In certain embodiments, the halo group is either fluoro or chloro.

"Haloalkyl" refers to an alkyl radical in which the alkyl group is substituted with one or more halogens. Typical haloalkyl groups include, but are not limited to, trifluoromethyl, difluoromethyl, fluoromethyl, chloromethyl, dichloromethyl, dibromoethyl, tribromomethyl, tetrafluoroethyl, and the like.

"Hydroxy" refers to the radical —OH.

"Nitro" refers to the radical —$NO_2$.

"Thioketo" refers to the group =S.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —$NO_2$, —$N_3$, —$SO_2H$, —$SO_3H$, —OH, —$OR^{aa}$, —$ON(R^{bb})_2$, —$N(R^{bb})_2$, —$N(R^{bb})_3{}^+X^-$, —$N(OR^{cc})R^{bb}$, —SH, —$SR^{aa}$, —$SSR^{cc}$, —$C(=O)R^{aa}$, —$CO_2H$, —CHO, —$C(OR^{cc})_2$, —$CO_2R^{aa}$, —$OC(=O)R^{aa}$, —$OCO_2R^{aa}$, —$C(=O)N(R^{bb})_2$, —$OC(=O)N(R^{bb})_2$, —$NR^{bb}C(=O)R^{aa}$, —$NR^{bb}CO_2R^{aa}$, —$NR^{bb}C(=O)N(R^{bb})_2$, —$C(=NR^{bb})R^{aa}$, —$C(=NR^{bb})OR^{aa}$, —$OC(=NR^{bb})R^{aa}$, —$OC(=NR^{bb})OR^{aa}$, —$C(=NR^{bb})N(R^{bb})_2$, —$OC(=NR^{bb})N(R^{bb})_2$, —$NR^{bb}C(=NR^{bb})N(R^{bb})_2$, —$C(=O)NR^{bb}SO_2R^{aa}$, —$NR^{bb}SO_2R^{aa}$, —$SO_2N(R^{bb})_2$, —$SO_2R^{aa}$, —$SO_2OR^{aa}$, —$OSO_2R^{aa}$, —$S(=O)R^{aa}$, —$OS(=O)R^{aa}$, —$Si(R^{aa})_3$, —$OSi(R^{aa})_3$—$C(=S)N(R^{bb})_2$, —$C(=O)SR^{aa}$, —$C(=S)SR^{aa}$, —$SC(=S)SR^{aa}$, —$SC(=O)SR^{aa}$, —$OC(=O)SR^{aa}$, —$SC(=O)OR^{aa}$, —$SC(=O)R^{aa}$, —$P(=O)_2R^{aa}$, —$OP(=O)_2R^{aa}$, —$P(=O)(R^{aa})_2$, —$OP(=O)(R^{aa})_2$, —$OP(=O)(OR^{cc})_2$—$P(=O)_2N(R^{bb})_2$, —$OP(=O)_2N(R^{bb})_2$, —$P(=O)(NR^{bb})_2$, —$OP(=O)(NR^{bb})_2$, —$NR^{bb}P(=O)(OR^{cc})_2$, —$NR^{bb}P(=O)(NR^{bb})_2$, —$P(R^{cc})_2$, —$P(R^{cc})_3$, —$OP(R^{cc})_2$, —$OP(R^{cc})_3$, —$B(R^{aa})_2$, —$B(OR^{cc})_2$, —$BR^{aa}(OR^{cc})$, $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^{dd}$ groups; or two geminal hydrogens on a carbon atom are replaced with the group =O, =S, =$NN(R^{bb})_2$, =$NNR^{bb}C(=O)R^{aa}$, =$NNR^{bb}C(=O)OR^{aa}$, =$NNR^{bb}S(=O)_2R^{aa}$, =$NR^{bb}$, or =$NOR^{cc}$;

each instance of $R^{aa}$ is, independently, selected from $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —$OR^{aa}$, —$N(R^{cc})_2$, —CN, —$C(=O)R^{aa}$, —$C(=O)N(R^{cc})_2$, —$CO_2R^{aa}$, —$SO_2R^{aa}$, —$C(=NR^{cc})OR^{aa}$, —$C(=NR^{cc})N(R^{cc})_2$, —$SO_2N(R^{cc})_2$, —$SO_2R^{cc}$, —$SO_2OR^{cc}$, —$SOR^{aa}$, —$C(=S)N(R^{cc})_2$, —$C(=O)SR^{cc}$, —$C(=S)SR^{cc}$, —$P(=O)_2R^{aa}$, —$P(=O)(R^{aa})_2$, —$P(=O)_2N(R^{cc})_2$, —$P(=O)(NR^{cc})_2$, $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —$NO_2$, —$N_3$, —$SO_2H$, —$SO_3H$, —OH, —$OR^{ee}$, —$ON(R^{ff})_2$, —$N(R^{ff})_2$, —$N(R^{f})_3^+X^-$, —$N(OR^{ee})R^{ff}$, —SH, —$SR^{ee}$, —$SSR^{ee}$, —C(=O)$R^{ee}$, —$CO_2H$, —$CO_2R^{ee}$, —OC(=O)Ree, —$OCO_2R^{ee}$, —C(=O)$N(R^{ff})_2$, —OC(=O)$N(R^{ff})_2$, —$NR^{ff}$C(=O)$R^{ee}$, —$NR^{ff}CO_2R^{ee}$, —$NR^{ff}$C(=O)$N(R^{ff})_2$, —C(=$NR^{ff}$)$OR^{ee}$, —OC(=$NR^{ff}$)$R^{ee}$, —OC(=$NR^{ff}$)$OR^{ee}$, —C(=$NR^{ff}$)$N(R^{ff})_2$, —OC(=$NR^{ff}$)$N(R^{ff})_2$, —$NR^{ee}$(=$NR^{ff}$)$N(R^{ff})_2$, —$NRSO_2R^{ee}$, —$SO_2N(R^{ff})_2$, —$SO_2R^{ee}$, —$SO_2OR^{ee}$, —$OSO_2R^{ee}$, —S(=O)$R^{ee}$, —$Si(R^{ee})_3$, —$OSi(R^{ee})_3$, —C(=S)$N(R^{ff})_2$, —C(=O)$SR^{ee}$, —C(=S)$SR^{ee}$, —SC(=S)$SR^{ee}$, —P(=O)$_2R^{ee}$, —P(=O)$(R^{ee})_2$, —OP(=O)$(R^{ee})_2$, —OP(=O)$(OR^{ee})_2$, $C_{1-6}$ alkyl, $C_{1-6}$ haloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ haloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ haloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{f}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —$NO_2$, —$N_3$, —$SO_2H$, —$SO_3H$, —OH, —$OC_{1-6}$ alkyl, —$ON(C_{1-6}$ alkyl$)_2$, —$N(C_{1-6}$ alkyl$)_2$, —$N(C_{1-6}$ alkyl$)_3^+X^-$, —$NH(C_{1-6}$ alkyl$)_2^+X^-$, —$NH_2(C_{1-6}$ alkyl$)^+X^-$, —$NH_3^+X^-$, —$N(OC_{1-6}$ alkyl)($C_{1-6}$ alkyl), —N(OH)($C_{1-6}$ alkyl), —NH(OH), —SH, —$SC_{1-6}$ alkyl, —SS($C_{1-6}$ alkyl), —C(=O)($C_{1-6}$ alkyl), —$CO_2H$, —$CO_2(C_{1-6}$ alkyl), —OC(=O)($C_{1-6}$ alkyl), —$OCO_2(C_{1-6}$ alkyl), —C(=O)$NH_2$, —C(=O)$N(C_{1-6}$ alkyl$)_2$, —OC(=O)NH($C_{1-6}$ alkyl), —NHC(=O)($C_{1-6}$ alkyl), —N($C_{1-6}$ alkyl)C(=O)($C_{1-6}$ alkyl), —$NHCO_2(C_{1-6}$ alkyl), —NHC(=O)$N(C_{1-6}$ alkyl$)_2$, —NHC(=O)NH($C_{1-6}$ alkyl), —NHC(=O)$NH_2$, —C(=NH)O($C_{1-6}$ alkyl), —OC(=NH)($C_{1-6}$ alkyl), —OC(=NH)$OC_{1-6}$ alkyl, —C(=NH)$N(C_{1-6}$ alkyl$)_2$, —C(=NH)NH($C_{1-6}$ alkyl), —C(=NH)$NH_2$, —OC(=NH)$N(C_{1-6}$ alkyl$)_2$, —OC(NH)NH($C_{1-6}$ alkyl), —OC(NH)$NH_2$, —NHC(NH)$N(C_{1-6}$ alkyl$)_2$, —NHC(=NH)$NH_2$, —$NHSO_2(C_{1-6}$ alkyl), —$SO_{2N}(C_{1-6}$ alkyl$)_2$, —$SO_2NH(C_{1-6}$ alkyl), —$SO_2NH_2$, —$SO_2C_{1-6}$ alkyl, —$SO_2OC_{1-6}$ alkyl, —$OSO_2C_{1-6}$ alkyl, —$SOC_{1-6}$ alkyl, —$Si(C_{1-6}$ alkyl$)_3$, —$OSi(C_{1-6}$ alkyl$)_3$—C(=S)$N(C_{1-6}$ alkyl$)_2$, C(=S)NH($C_{1-6}$ alkyl), C(=S)$NH_2$, —C(=O)S($C_{1-6}$ alkyl), —C(=S)$SC_{1-6}$ alkyl, —SC(=S)$SC_{1-6}$ alkyl, —P(=O)$_2(C_{1-6}$ alkyl), —P(=O)$(C_{1-6}$ alkyl$)_2$, —OP(=O)$(C_{1-6}$ alkyl$)_2$, —OP(=O)$(OC_{1-6}$ alkyl$)_2$, $C_{1-6}$ alkyl, $C_{1-6}$ haloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^9$ substituents can be joined to form =O or =S; wherein X is a counterion.

A "counterion" or "anionic counterion" is a negatively charged group associated with a cationic quaternary amino group in order to maintain electronic neutrality. Exemplary counterions include halide ions (e.g., $F^-$, $Cl^-$, $Br^-$, $I^-$), $NO_3^-$, $ClO_4^-$, $OH^-$, $H_2PO_4^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

These and other exemplary substituents are described in more detail in the Detailed Description, and Claims. The invention is not intended to be limited in any manner by the above exemplary listing of substituents.

Other Definitions

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like. The term "pharmaceutically acceptable cation" refers to an acceptable cationic counterion of an acidic functional group. Such cations are exemplified by sodium, potassium, calcium, magnesium, ammonium, tetraalkylammonium cations, and the like. See, e.g., Berge, et al., *J. Pharm. Sci.* (1977) 66(1): 1-79.

The term "prodrug" is intended to encompass therapeutically inactive compounds that, under physiological conditions, are converted into the therapeutically active agents of the present invention. One method for making a prodrug is to design selected moieties that are hydrolyzed or cleaved at a targeted in vivo site of action under physiological conditions to reveal the desired molecule which then produces its therapeutic effect. In certain embodiments, the prodrug is converted by an enzymatic activity of the subject.

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base. Tautomeric forms may be relevant to the attainment of the optimal chemical reactivity and biological activity of a compound of interest.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal.

In certain embodiments, the substituent present on an oxygen atom is an oxygen protecting group (also referred to as a hydroxyl protecting group). Oxygen protecting groups include, but are not limited to, $—R^{aa}$, $—N(R^{bb})_2$, $—C(═O)SR^{aa}$, $—C(═O)R^{aa}$, $—CO_2R^{aa}$, $—C(═O)N(R^{bb})_2$, $—C(═NR^{bb})R^{aa}$, $—C(═NR^{bb})OR^{aa}$, $—C(═NR^{bb})N(R^{bb})_2$, $—S(═O)R^{aa}$, $—SO_2R^{aa}$, $—Si(R^{aa})_3$, $—P(R^{cc})_2$, $—P(R^{cc})_3$, $—P(═O)_2R^{aa}$, $—P(═O)(R^{aa})_2$, $—P(═O)(OR^{cc})_2$, $—P(═O)_2N(R^{bb})_2$, and $—P(═O)(NR^{bb})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Exemplary oxygen protecting groups include, but are not limited to, methyl, methoxymethyl (MOM), 2-methoxyethoxymethyl (MEM), benzyl (Bn), triisopropylsilyl (TIPS), t-butyldimethylsilyl (TBDMS), t-butylmethoxyphenylsilyl (TBMPS), methanesulfonate (mesylate), and tosylate (Ts).

In certain embodiments, the substituent present on an sulfur atom is an sulfur protecting group (also referred to as a thiol protecting group). Sulfur protecting groups include, but are not limited to, $—R^{aa}$, $—N(R^{bb})_2$, $—C(═O)SR^{aa}$, $—C(═O)R^{aa}$, $—CO_2R^{aa}$, $—C(═O)N(R^{bb})_2$, $—C(═NR^{bb})R^{aa}$, $—C(═NR^{bb})OR^{aa}$, $—C(═NR^{bb})N(R^{bb})_2$, $—S(═O)R^{aa}$, $—SO_2R^{aa}$, $—Si(R^{aa})_3$, $—P(R^{cc})_2$, $—P(R^{cc})_3$, $—P(═O)_2R^{aa}$, $—P(═O)(R^{aa})_2$, $—P(═O)(OR^{cc})_2$, $—P(═O)_2N(R^{bb})_2$, and $—P(═O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference.

In certain embodiments, the substituent present on a nitrogen atom is an amino protecting group (also referred to herein as a nitrogen protecting group). Amino protecting groups include, but are not limited to, —OH, $—OR^{aa}$, $—N(R^{cc})_2$, $—C(═O)R^{aa}$, $—C(═O)OR^{aa}$, $—C(═O)N(R^{cc})_2$, $—S(═O)_2Ra$, $—C(═NR^{cc})R^{aa}$, $—C(═NR^{cc})OR^{aa}$, $—C(═NR^{cc})N(R^{cc})_2$, $—SO_2N(R^{cc})_2$, $—SO_2R^{cc}$, $—SO_2OR^{cc}$, $—SOR^{aa}$, $—C(═S)N(R^{cc})_2$, $—C(═O)SR^{cc}$, $—C(═S)SR^{cc}$, $C_{1-10}$ alkyl, $C_{2-10}$ alkenyl, $C_{2-10}$ alkynyl, $C_{3-10}$ carbocyclyl, 3-14-membered heterocyclyl, $C_{6-14}$ aryl, and 5-14-membered heteroaryl groups, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Amino protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Exemplary amino protecting groups include, but are not limited to amide groups (e.g., $—C(═O)R^{aa}$), which include, but are not limited to, formamide and acetamide; carbamate groups (e.g., $—C(═O)OR^{aa}$), which include, but are not limited to, 9-fluorenylmethyl carbamate (Fmoc), t-butyl carbamate (BOC), and benzyl carbamate (Cbz); sulfonamide groups (e.g., $—S(═O)_2R^{aa}$), which include, but are not limited to, p-toluenesulfonamide (Ts), methanesulfonamide (Ms), and N-[2-(trimethylsilyl)ethoxy]methylamine (SEM).

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition.

In general, the "effective amount" of a compound refers to an amount sufficient to elicit the desired biological response, e.g., to treat a neuropathy-related disorder. As will be appreciated by those of ordinary skill in this art, the effective amount of a compound of the invention may vary depending on such factors as the desired biological endpoint, the pharmacokinetics of the compound, the disease being treated, the mode of administration, and the age, weight, health, and condition of the subject.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

In an alternate embodiment, the present invention contemplates administration of the compounds of the present invention or a pharmaceutically acceptable salt or a pharmaceutically acceptable composition thereof, as a prophylactic before a subject begins to suffer from the specified disease, disorder or condition. As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

Compounds

In an aspect, provided herein is a compound of Formula (I):

Formula (I)

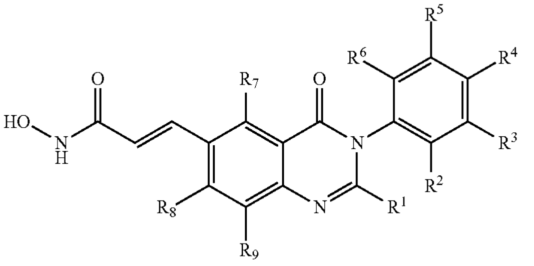

or a pharmaceutically acceptable salt thereof, wherein $R^1$ is $(C_{1-2})$alkyl, or fluoro$(C_{1-2})$alkyl;

$R^2$ is hydrogen, halogen, or $(C_{1-3})$alkyl;

$R^3$ is hydrogen, or $(C_{1-3})$alkyl;

$R^4$ is hydrogen, halogen, or $(C_{1-3})$alkyl, methoxy or $N(C_{1-3})(C_{1-3})$;

$R^5$ is hydrogen, $(C_{1-3})$alkyl, halogen, or trifluoromethyl;

$R^6$ is hydrogen, $(C_{1-3})$alkyl, halogen;

$R^7$ is hydrogen or halogen;

$R^8$ is hydrogen, methyl, methoxy, or fluoro; and $R^9$ is hydrogen or fluoro.

In some embodiments, the compound is of Formula (IA)

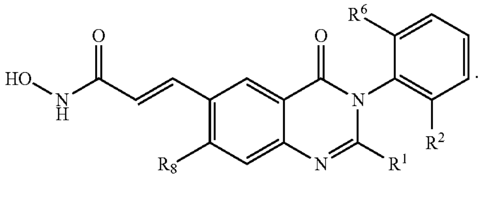

In some embodiments, the compound is of Formula (IB)

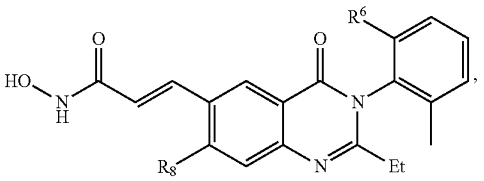

Group $R^1$

In some embodiments, $R^1$ is $(C_{1-2})$alkyl, or fluoro$(C_{1-2})$alkyl.

In some aspects, $R^1$ is methyl.

In some aspects, $R^1$ is ethyl.

In some aspects, $R^1$ is hydrogen.

Group $R^2$

In some embodiments, $R^2$ is hydrogen, halogen, or $(C_{1-3})$alkyl

In some embodiments, $R^2$ is methyl.

In some embodiments, $R^2$ is ethyl.

In some embodiments, $R^2$ is fluoro.

In some embodiments, $R^2$ is isopropyl.

Group $R^3$

In some embodiments, $R^3$ is hydrogen, or $(C_{1-3})$alkyl.

In some embodiments, $R^3$ is hydrogen.

In some embodiments, $R^3$ is methyl.

In some embodiments, $R^3$ is ethyl.

Group $R^4$

In some embodiments, $R^4$ is hydrogen, halogen, $(C_{1-3})$alkyl, methoxy, or $N(C_{1-3})(C_{1-3})$ In some embodiments, $R^4$ is hydrogen.

In some embodiments, $R^4$ is methyl.

In some embodiments, $R^4$ is ethyl.

In some embodiments, $R^4$ is methoxy.

In some embodiments, $R^4$ is dimethylamino.

In some embodiments, $R^4$ is fluoro

In some embodiments, $R^4$ is chloro.

In some embodiments, $R^4$ is bromo.

Group $R^5$

In some embodiments, $R^5$ is hydrogen, $(C_{1-3})$alkyl, halogen, or trifluoromethyl.

In some embodiments, $R^5$ is hydrogen.

In some embodiments, $R^5$ is methyl.

In some embodiments, $R^5$ is ethyl.

In some embodiments, $R^5$ is trifluoromethyl

Group $R^6$

In some embodiments, $R^6$ is hydrogen, $(C_{1-3})$alkyl, or halogen.

In some embodiments, $R^6$ is hydrogen.

In some embodiments, $R^6$ is methyl.

In some embodiments, $R^6$ is ethyl.

In some embodiments, $R^6$ is isopropyl.

Group $R^7$

In some embodiments, $R^7$ is hydrogen or halogen.

In some embodiments, $R^7$ is hydrogen.

In some embodiments, $R^7$ is fluoro.

Group $R^8$

In some embodiments, $R^8$ is hydrogen, methyl, methoxy, or fluoro.

In some embodiments, $R^8$ is hydrogen.

In some embodiments, $R^8$ is methyl.

In some embodiments, $R^8$ is ethyl.

In some embodiments, $R^8$ is methoxy

In some embodiments, $R^8$ is fluoro.

Group $R^9$

In some embodiments, $R^9$ is hydrogen or fluoro.

In some embodiments, $R^9$ is hydrogen.

In some embodiments, $R^9$ is fluoro.

In some embodiments, the compound is of Formula (IA) and $R^2$ and $R^6$ are each methyl. In some embodiments, the compound is of Formula (IA) and $R^2$ and $R^6$ are each methyl and $R^1$ is ethyl. In some embodiments, the compound is of Formula (IA) and $R^2$ and $R^6$ are each methyl and $R^1$ is ethyl and $R^8$ is fluoro.

In some embodiments, the compound is of Formula (IA) and $R^2$ and $R^6$ are each hydrogen. In some embodiments, the compound is of Formula (IA) and $R^2$ and $R^6$ are each hydrogen and $R^1$ is ethyl. In some embodiments, the compound is of Formula (IA) and $R^2$ and $R^6$ are each hydrogen and $R^1$ is ethyl and $R^8$ is fluoro.

In some embodiments, the compound is of Formula (IA) and $R^1$ is ethyl.

In some embodiments, the compound is of Formula (IA) and $R^8$ is fluoro.

In some embodiments, the compound is selected from the group consisting of the compounds identified in Table 1 below:

TABLE 1

| Compound No. | Structure |
|---|---|
| 1 | 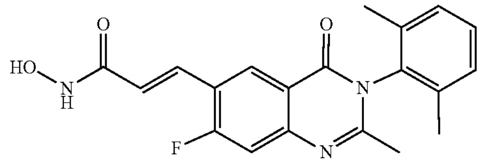 [SMILES: Cc1cccc(C)c1-n1c(C)nc2cc(F)c(/C=C/C(=O)NO)cc2c1=O] |
| 2 | 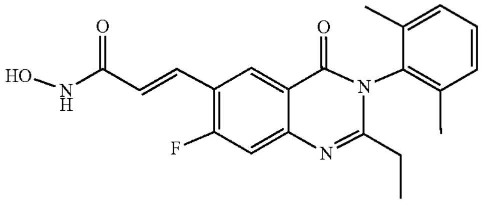 [SMILES: CCc1nc2cc(F)c(/C=C/C(=O)NO)cc2c(=O)n1-c1c(C)cccc1C] |
| 3 | 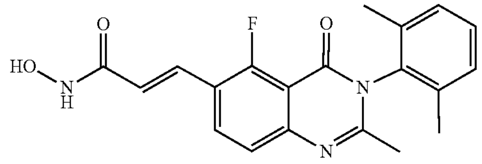 [SMILES: Cc1cccc(C)c1-n1c(C)nc2ccc(/C=C/C(=O)NO)c(F)c2c1=O] |
| 4 | 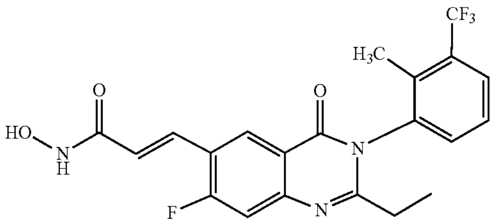 [SMILES: CCc1nc2cc(F)c(/C=C/C(=O)NO)cc2c(=O)n1-c1cccc(C(F)(F)F)c1C] |
| 5 | 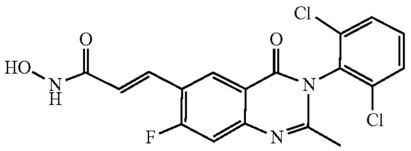 [SMILES: Cc1nc2cc(F)c(/C=C/C(=O)NO)cc2c(=O)n1-c1c(Cl)cccc1Cl] |

TABLE 1-continued

| Compound No. | Structure |
|---|---|
| 6 | 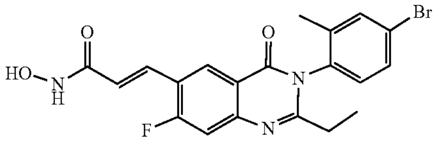 [SMILES: CCc1nc2cc(F)c(/C=C/C(=O)NO)cc2c(=O)n1-c1ccc(Br)cc1C] |
| 7 | 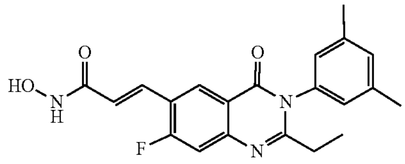 [SMILES: CCc1nc2cc(F)c(/C=C/C(=O)NO)cc2c(=O)n1-c1cc(C)cc(C)c1] |
| 8 | 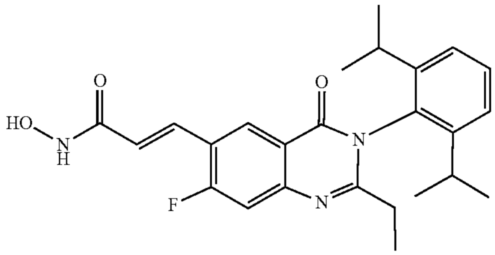 [SMILES: CCc1nc2cc(F)c(/C=C/C(=O)NO)cc2c(=O)n1-c1c(C(C)C)cccc1C(C)C] |
| 9 | 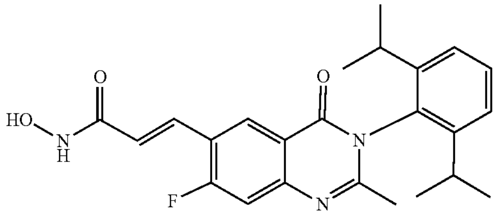 [SMILES: Cc1nc2cc(F)c(/C=C/C(=O)NO)cc2c(=O)n1-c1c(C(C)C)cccc1C(C)C] |
| 10 | 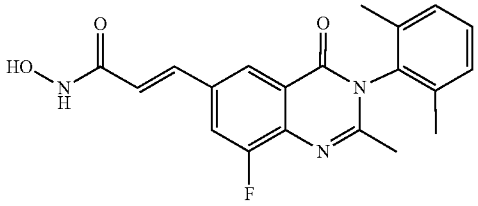 [SMILES: Cc1cccc(C)c1-n1c(C)nc2c(F)cc(/C=C/C(=O)NO)cc2c1=O] |
| 11 | 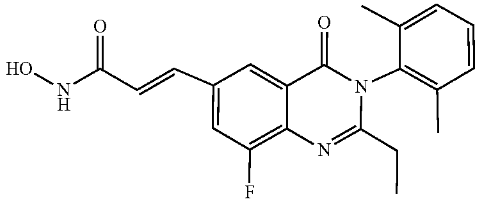 [SMILES: CCc1nc2c(F)cc(/C=C/C(=O)NO)cc2c(=O)n1-c1c(C)cccc1C] |
| 12 | 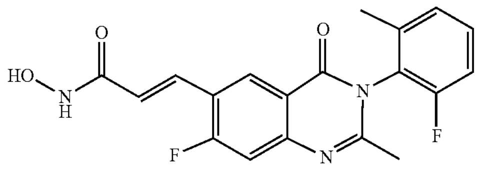 [SMILES: Cc1cccc(F)c1-n1c(C)nc2cc(F)c(/C=C/C(=O)NO)cc2c1=O] |

TABLE 1-continued
| Compound No. | Structure |
|---|---|
| 13 | 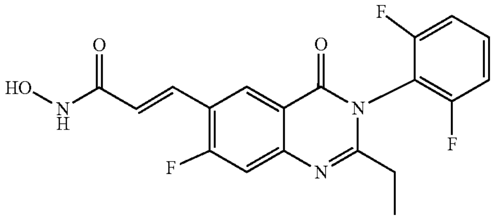 [SMILES: CCc1nc2cc(F)c(/C=C/C(=O)NO)cc2c(=O)n1-c1c(F)cccc1F] |
| 14 | 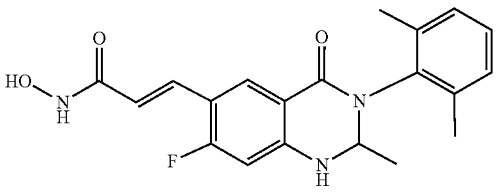 [SMILES: Cc1cccc(C)c1N1C(=O)c2cc(/C=C/C(=O)NO)c(F)cc2NC1C] |
| 15 | 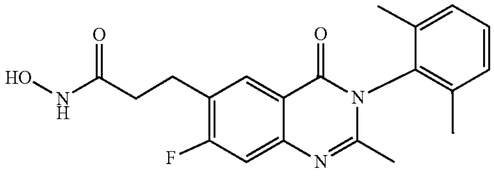 [SMILES: Cc1cccc(C)c1-n1c(C)nc2cc(F)c(CCC(=O)NO)cc2c1=O] |
| 16 | 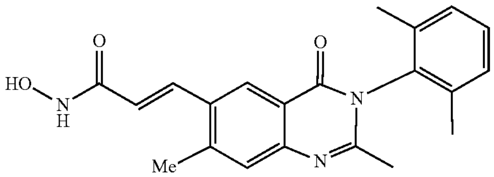 [SMILES: Cc1cc2nc(C)n(-c3c(C)cccc3C)c(=O)c2cc1/C=C/C(=O)NO] |
| 17 | 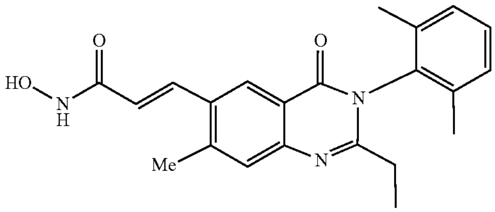 [SMILES: CCc1nc2cc(C)c(/C=C/C(=O)NO)cc2c(=O)n1-c1c(C)cccc1C] |
| 18 | 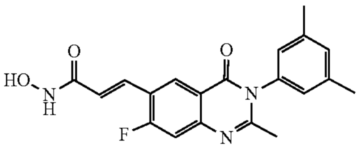 [SMILES: Cc1cc(C)cc(-n2c(C)nc3cc(F)c(/C=C/C(=O)NO)cc3c2=O)c1] |
| 19 | 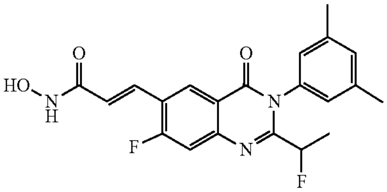 [SMILES: Cc1cc(C)cc(-n2c(C(C)F)nc3cc(F)c(/C=C/C(=O)NO)cc3c2=O)c1] |
| 20 | 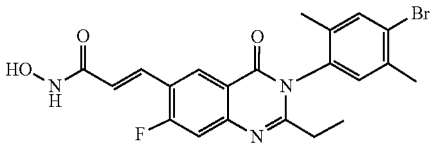 [SMILES: CCc1nc2cc(F)c(/C=C/C(=O)NO)cc2c(=O)n1-c1cc(C)c(Br)cc1C] |
TABLE 1-continued
| Compound No. | Structure |
|---|---|
| 21 | 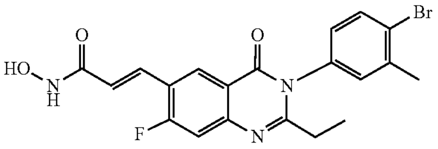 [SMILES: CCc1nc2cc(F)c(/C=C/C(=O)NO)cc2c(=O)n1-c1ccc(Br)c(C)c1] |
| 22 | 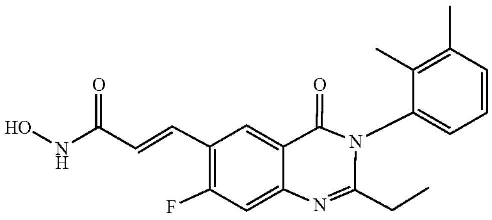 [SMILES: CCc1nc2cc(F)c(/C=C/C(=O)NO)cc2c(=O)n1-c1cccc(C)c1C] |
| 23 | 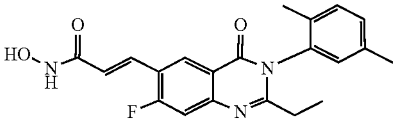 [SMILES: CCc1nc2cc(F)c(/C=C/C(=O)NO)cc2c(=O)n1-c1cc(C)ccc1C] |
| 24 | 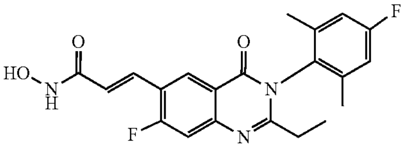 [SMILES: CCc1nc2cc(F)c(/C=C/C(=O)NO)cc2c(=O)n1-c1c(C)cc(F)cc1C] |
| 25 | 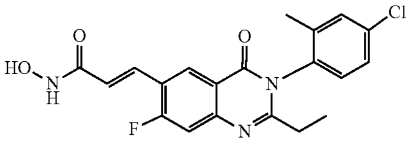 [SMILES: CCc1nc2cc(F)c(/C=C/C(=O)NO)cc2c(=O)n1-c1ccc(Cl)cc1C] |
| 26 | 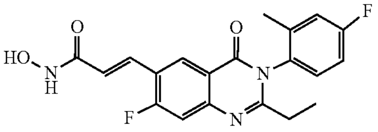 [SMILES: CCc1nc2cc(F)c(/C=C/C(=O)NO)cc2c(=O)n1-c1ccc(F)cc1C] |
| 27 | 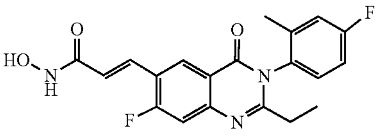 [SMILES: CCc1nc2cc(F)c(/C=C/C(=O)NO)cc2c(=O)n1-c1ccc(F)cc1C] |
| 28 | 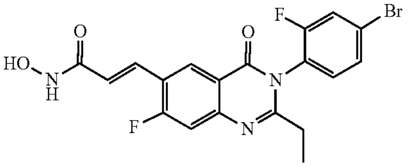 [SMILES: CCc1nc2cc(F)c(/C=C/C(=O)NO)cc2c(=O)n1-c1ccc(Br)cc1F] |
| 29 | 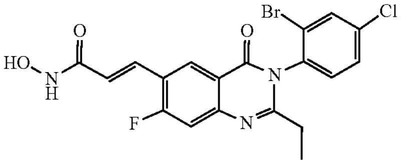 [SMILES: CCc1nc2cc(F)c(/C=C/C(=O)NO)cc2c(=O)n1-c1ccc(Cl)cc1Br] |

TABLE 1-continued

| Compound No. | Structure |
|---|---|
| 30 | 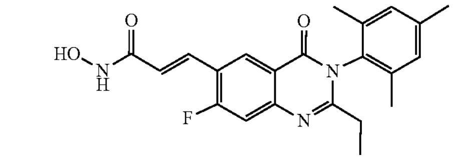 [SMILES: CCc1nc2cc(F)c(/C=C/C(=O)NO)cc2c(=O)n1-c1c(C)cc(C)cc1C] |
| 31 | 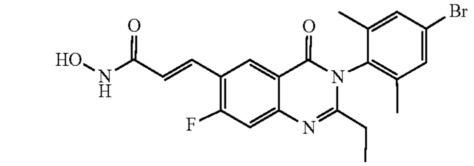 [SMILES: CCc1nc2cc(F)c(/C=C/C(=O)NO)cc2c(=O)n1-c1c(C)cc(Br)cc1C] |
| 32 | 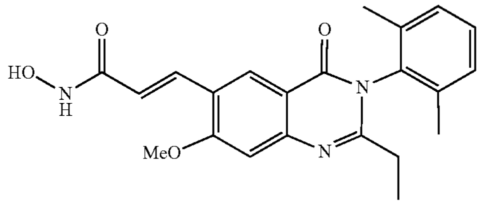 [SMILES: CCc1nc2cc(OC)c(/C=C/C(=O)NO)cc2c(=O)n1-c1c(C)cccc1C] |
| 33 | 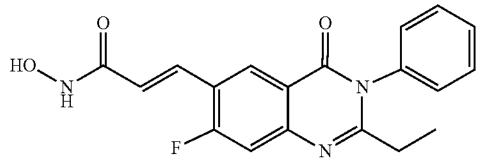 [SMILES: CCc1nc2cc(F)c(/C=C/C(=O)NO)cc2c(=O)n1-c1ccccc1] |
| 34 | 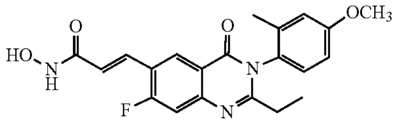 [SMILES: CCc1nc2cc(F)c(/C=C/C(=O)NO)cc2c(=O)n1-c1ccc(OC)cc1C] |
| 35 | 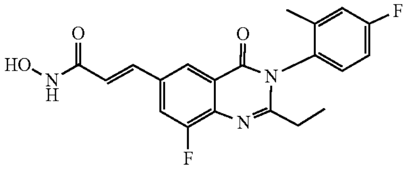 [SMILES: CCc1nc2c(F)cc(/C=C/C(=O)NO)cc2c(=O)n1-c1ccc(F)cc1C] |
| 36 | 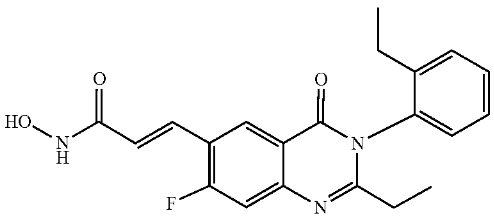 [SMILES: CCc1ccccc1-n1c(CC)nc2cc(F)c(/C=C/C(=O)NO)cc2c1=O] |
| 37 | 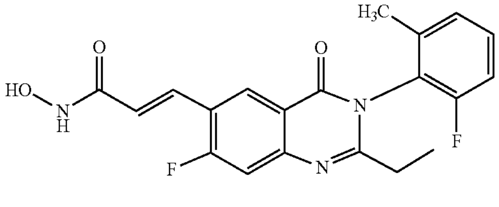 [SMILES: CCc1nc2cc(F)c(/C=C/C(=O)NO)cc2c(=O)n1-c1c(C)cccc1F] |

TABLE 1-continued

| Compound No. | Structure |
|---|---|
| 38 | 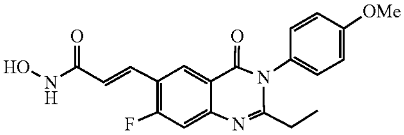 [SMILES: CCc1nc2cc(F)c(/C=C/C(=O)NO)cc2c(=O)n1-c1ccc(OC)cc1] |
| 39 | 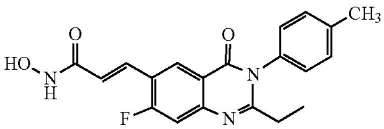 [SMILES: CCc1nc2cc(F)c(/C=C/C(=O)NO)cc2c(=O)n1-c1ccc(C)cc1] |
| 40 | 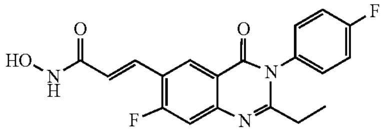 [SMILES: CCc1nc2cc(F)c(/C=C/C(=O)NO)cc2c(=O)n1-c1ccc(F)cc1] |
| 41 | 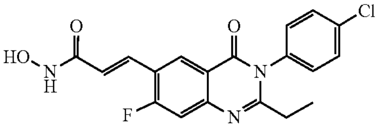 [SMILES: CCc1nc2cc(F)c(/C=C/C(=O)NO)cc2c(=O)n1-c1ccc(Cl)cc1] |
| 42 | 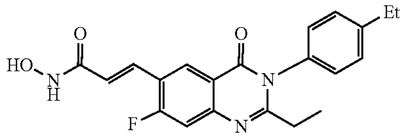 [SMILES: CCc1ccc(-n2c(CC)nc3cc(F)c(/C=C/C(=O)NO)cc3c2=O)cc1] |
| 43 | 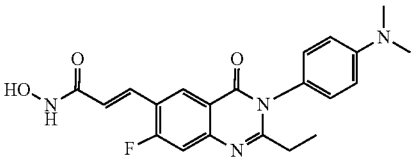 [SMILES: CCc1nc2cc(F)c(/C=C/C(=O)NO)cc2c(=O)n1-c1ccc(N(C)C)cc1] |
| 44 | 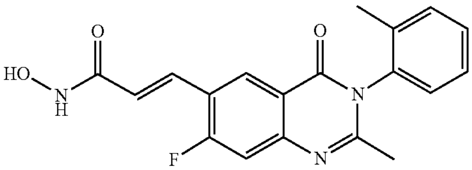 [SMILES: Cc1ccccc1-n1c(C)nc2cc(F)c(/C=C/C(=O)NO)cc2c1=O] |

In one aspect, provided here in is a compound described herein. In another aspect, provided herein is a pharmaceutically acceptable salt of a compound described herein (e.g., a compound of Formula (I) or Formula (II)).

In one aspect, provided herein is a pharmaceutical composition comprising a compound described herein (e.g., a compound of Formula (I) or Formula (II)) or a pharmaceutically acceptable salt thereof, and a pharmaceutically acceptable excipient. In certain embodiments, the compound of the present invention is provided in an effective amount in the pharmaceutical composition. In certain embodiments, the compound of the present invention is provided in a therapeutically effective amount.

ALTERNATIVE EMBODIMENTS

In an alternative embodiment, compounds described herein may also comprise one or more isotopic substitutions. For example, hydrogen may be $^2$H (D or deuterium) or $^3$H (T or tritium); carbon may be, for example, $^{13}C$ or $^{14}C$; oxygen may be, for example, $^{18}O$; nitrogen may be, for example, $^{15}N$, and the like. In other embodiments, a particular isotope (e.g., $^{3}H$, $^{13}C$, $^{14}C$, $^{18}O$, or $^{15}N$) can represent at least 1%, at least 5%, at least 10%, at least 15%, at least 20%, at least 25%, at least 30%, at least 35%, at least 40%, at least 45%, at least 50%, at least 60%, at least 65%, at least 70%, at least 75%, at least 80%, at least 85%, at least 90%, at least 95%, at least 99%, or at least 99.9% of the total isotopic abundance of an element that occupies a specific site of the compound.

Methods of Use and Treatment

In some aspects, compounds of Formula (I) or Formula (II) are useful for enhancing tubulin hyperacetylation in cells. The microtubule network is formed by the polymerization of a/P tubulin heterodimers and plays an important role in the regulation of cell shape, intracellular transport, cell motility, and cell division. α and β tubulin sub-units are subject to numerous post-translational modifications including tyrosination, phosphorylation, polyglutamylation, polyglycylation and acetylation. Tubulin represents one of the major acetylated cytoplasmic protein, and is a major substrate of the histone deacetylase HDAC6. Inhibition of HDAC6 results in higher levels of tublin acetylation, and is known to enhance mitochondrial movement in hipocampal neurons. It is envisioned that inhibiting HDAC6 may increase mitochondrial transporation in neuron cells and enhance neuron regeneration.

In some aspects described herein, e.g., compounds of Formula (I) or Formula (II), are useful to promote neurite outgrowth and neurite regeneration in a subject in need of. In some aspects disclosed herein, compounds of Formula (I) are useful in ameliorating conditions related to neurite degeneration of a subject in need of.

In some other aspects, disclosed herein are methods using the compounds described herein, e.g., compounds of Formula (I) or Formula (II), to be useful as therapeutic agents for the treatment of nerve or neuron damage.

In some further aspects, herein are methods using the compounds described herein, e.g., compounds of Formula (I) or Formula (II), to be useful as therapeutic agents for inducing nerve or neuron regeneration.

In some aspects disclosed described herein, e.g., compounds of Formula (I) or Formula (II), are useful as therapeutic agents for treating neuropathic related diseases.

In some aspects, compounds described herein, e.g., compounds of Formula (I) or Formula (II), are useful as therapeutic agents for treating neuropathy.

Examples of the neuropathic related diseases are, for example, neuropathic pain, but it can also be applied to diabetic neuropathy, post-herpes zoster pain, postherpetic neuralgia from shingles, fiber muscle pain, and the like. However, neuropathic related diseases are not limited to pain, and may be various peripheral neuropathic pains and central neuropathic pains, painful diabetic neuropathy, complex regional pain syndrome, nerve damage induced by chemotherapy, cancer pain, HIV-associated sensory neuropathy, HIV-associated myelopathy, phantom limb pain, trigeminal neuralgia, postherpetic neuralgia, painful radiculopathy, central post-stroke pain, sciatic neuralgia, orofacial pain, acute or chronic inflammatory demyelinating polyradiculopathy, alcoholic neuropathy, carpal tunnel syndrome, knuckle pain, snapping finger, iatrogenic nerve damage, neurothlipsia by tumor or nerve damage by infiltration, post radiation nerve damage, toxic peripheral neuropathy, post-traumatic peripheral nerve injury pain, glossopharyngeal neuralgia, autoimmune nerve damage, acute, chronic or intractable muscle and fascia pain, postapoplectic pain, post-traumatic spinal cord injury pain, pain accompanying multiple sclerosis or Parkinson's disease, spinal canal stenosis or hernia pain, so-called low back pain, pain resulting from cervical spondylosis or ligamentum osteosis, pain of stomatitis, perishoulder arthritis, rheumatoid arthritis or osteoarthritis, nociceptive pain, pain of incised wound, abrasion, bone fracture, or bruise, pain caused by insertion of dialysis needle or pain resulting from dialysis at the time of dialysis, senile or nervous itch, itch of scalp, atopic dermatitis, restless legs syndrome, numbness of hand and foot, pain after odontectomy, postoperative pain, pain prophylaxis by preoperative administration, and the like.

In some embodiments, compounds of Formula (I) or Formula (II) are used for treating peripheral neuropathic pain disorders such as those that have a generalized (usually symmetrical) distribution and those that have a focal distribution. Peripheral neuropathies include those associated with diabetes mellitus, pre-diabetes and other metabolic dysfunctions, infectious diseases (mainly HIV infection and leprosy), chemotherapy, immune (for example, Guillain-Barre syndrome) and inflammatory disorders, inherited neuropathies and channelopathies (such as inherited erythromelalgia, a disorder in which blood vessels are episodically blocked then become hyperaemic and inflamed).

In some aspects, compounds described herein, e.g., compounds of Formula (I) or Formula (II), are useful as therapeutic agents for treating trigeminal neuralgia.

In some embodiments, compounds of Formula (I) or Formula (II) can be used in treating diabetic neuropathy, a type of nerve damage that occurs in diabetic patients and is a serious diabetes complication that may affect as many as 50% of people with diabetes.

In some aspects, compounds described herein, e.g., compounds of Formula (I) or Formula (II), are envisioned to be useful as therapeutic agents for treating chemotherapy-induced peripheral neuropathy (CIPN). Chemotherapy-induced peripheral neuropathy (CIPN) is one of the most commonly and widely reported adverse side effects of cancer treatment. The overall incidence of CIPN ranges from 30%-80% in patients treated for cancer, depending on the chemotherapy regimens used and the duration of treatment. The occurrence of CIPN can limit the chemotherapeutic dosage, delay additional treatment cycles, and even lead to early termination of treatment. Moreover, CIPN frequently persists or even worsens after completion of chemotherapy, thereby greatly reducing quality of life for cancer survivors.

In some embodiments, the chemotherapy is platinum-based chemotherapy, alkaloid-based, or taxane-based chemotherapy.

In some aspects disclosed herein, compounds described herein, e.g., compounds of Formula (I) are useful in treating or ameliorating conditions associated with acute inflammatory responses in organ tissues. In some embodiments, said compounds are used in treating or ameliorating acute respiratory distress syndrome. In some embodiments described herein, said compounds are used in treating or amediorating conditions associated with acute pulmonary inflammation.

In some aspects disclosed herein, compounds described herein, e.g., compounds of Formula (I) or Formula (II), are useful as therapeutic agents for treating inflammation-related diseases. In some embodiments, the inflammation-related diseases are associated with cytokine storms.

In some aspects, compounds disclosed herein, e.g. compounds of Formula (I) or Formula (II), are useful as therapeutic agents in treating or ameliorating conditions arising from excessive fibrosis in response to injuries that are related to inflammatory response. In some embodiments, compounds disclosed herein, e.g. compounds of Formula (I) or Formula (II), are useful as therapeutic agents for decreasing expression of collagens, such as collagen I or collagen III in a subject in need.

In further embodiments, said fibrosis is pulmonary fibrosis, hepatic fibrosis, or renal fibrosis, and in some embodiments, pulmonary fibrosis is associated with increased expression of TNF-α, IL-1, or IL-6. In other embodiments, said pulmonary fibrosis is idiopathic pulmonary fibrosis or virus-induced fibrosis. In further embodiments, use of the selective HDAC6 inhibitor disclosed herein in the manufacture of a medicament for the treatment of pulmonary fibrosis, liver fibrosis, and renal fibrosis.

In some aspects, compounds described herein, e.g., compounds of Formula (I) or Formula (II), are useful as therapeutic agents for treating or ameliorating cytokine-induced inflammatory conditions in a subject in need. Such cytokines may be TNF-α, IL-1, IL-6, M-CSF, MCP-1, MMP-1, and MMP9.

In some aspects, compounds described herein, e.g., compounds of Formula (I) or Formula (II), are useful as therapeutic agents for decreasing expression of TNF-α, IL-1, and IL-6 in a subject in need of.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Materials and Methods

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include (but are not limited to) trituration, column chromatography, HPLC, or supercritical fluid chromatography (SFC). The following schemes are presented with details as to the preparation of representative oxysterols that have been listed herein. The compounds provided herein may be prepared from known or commercially available starting materials and reagents by one skilled in the art of organic synthesis. Exemplary chiral columns available for use in the separation/purification of the enantiomers/diastereomers provided herein include, but are not limited to, CHIRALPAK®AD-10, CHIRALCEL® OB, CHIRALCEL® OB-H, CHIRALCEL® OD, CHIRALCEL® OD-H, CHIRALCEL® OF, CHIRALCEL® OG, CHIRALCEL® OJ and CHIRALCEL® OK.

$^1$H-NMR reported herein (e.g., for the region between δ (ppm) of about 0.5 to about 4 ppm) will be understood to be an exemplary interpretation of the NMR spectrum (e.g., exemplary peak integrations) of a compound.

Abbreviations: PE: petroleum ether; EtOAc: ethyl acetate; THF: tetrahydrofuran; PCC: pyridinium chlorochromate; TLC: thin layer chromatography; PCC: pyridinium chlorochromate; t-BuOK: potassium tert-butoxide; 9-BBN: 9-borabicyclo[3.3.1]nonane; $Pd(t-Bu_3P)_2$: bis(tri-tert-butylphosphine)palladium(0); AcCl: acetyl chloride; i-PrMgCl: Isopropylmagnesium chloride; TBSCl: tert-Butyl (chloro)dimethylsilane; $(i-PrO)_4Ti$: titanium tetraisopropoxide; BHT: 2,6-di-t-butyl-4-methylphenoxide; Me: methyl; i-Pr: iso-propyl; t-Bu: tert-butyl; Ph: phenyl; Et: ethyl; Bz: benzoyl; BzCl: benzoyl chloride; CsF: cesium fluoride; DCC: dicyclohexylcarbodiimide; DCM: dichloromethane; DMAP: 4-dimethylaminopyridine; DMP: Dess-Martin periodinane; EtMgBr: ethylmagnesium bromide; EtOAc: ethyl acetate; TEA: triethylamine; AlaOH: alanine; Boc: t-butoxycarbonyl. Py: pyridine; TBAF: tetra-n-butylammonium fluoride; THF: tetrahydrofuran; TBS: t-butyldimethylsilyl; TMS: trimethylsilyl; $TMSCF_3$: (Trifluoromethyl) trimethylsilane; Ts: p-toluenesulfonyl; Bu: butyl; $Ti(OiPr)_4$: tetraisopropoxytitanium; LAH: Lithium Aluminium Hydride; LDA: lithium diisopropylamide; $LiOH·H_2O$: lithium hydroxide hydrates; MAD: methyl aluminum bis(2,6-di-t-butyl-4-methylphenoxide); MeCN: acetonitrile; NBS: N-bromosuccinimide; $Na_2SO_4$: sodium sulfate; $Na_2S_2O_3$: sodium thiosulfate; MeCN: acetonitrile; MeOH: methanol; Boc: t-butoxycarbonyl; MTBE: methyl tert-butyl ether; K-selectride: Potassium tri(s-butyl)borohydride; 9-BBNdimer: 9-borabicyclo(3.3.1)nonane(dimer); DIPEA: diisopropylethylamine; DMF: dimethylformamide; FA: formic acid; SM: starting material.

Example 1: Scheme 1-2a

Scheme 1-2[a]

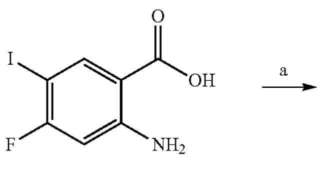

2a

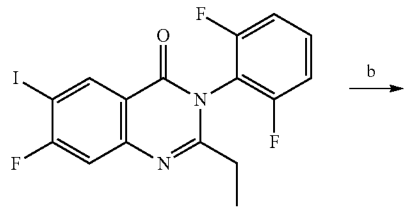

3o

-continued

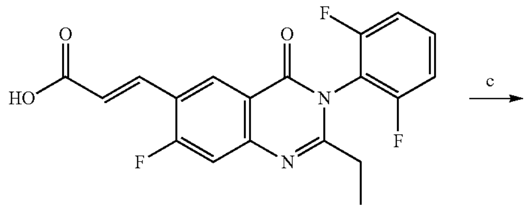

4o

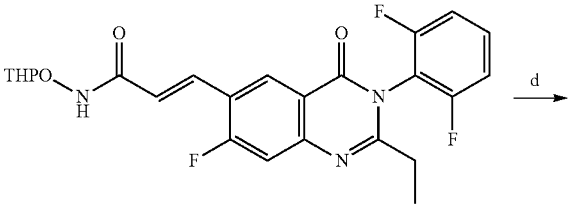

5o

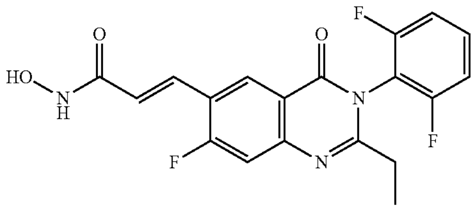

6o

[a]Reagents and conditions: (a) (i) propionic anhydride, $P(OPh)_3$, 0° C.-rt, 20 min; (ii) 2,6-difluoroaniline, pyridine, MW, 200 W, 20 min, 40%; (b) acrylic acid, $Pd(OAc)_2$, $[(t\text{-}Bu)_3PH]BF_4$, $Cs_2CO_3$, DMF, MW 200 W, 25 min, 86%; (c) (i) EDCI HCl, HOBt (ii) $NH_2OTHP$, DMF, rt, 23 h, 66%; (d) TFA, MeOH, 86%

Example 2

Scheme 1-3[a]

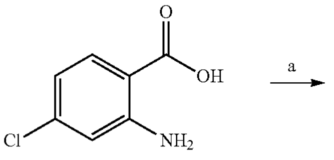

1d

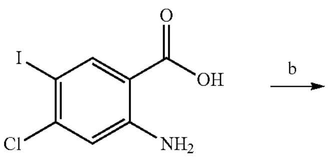

2d

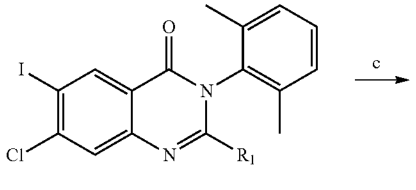

3q: $R_1$ = Me
3r: $R_1$ = Et, 43%

-continued

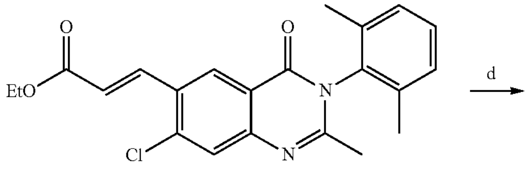

4q: $R_1$ = Me, 22% (two steps)
4r: $R_1$ = Et, 55%

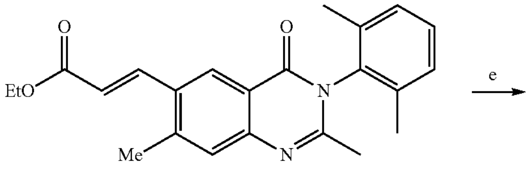

5q: $R_1$ = Me, 35%
5r: $R_1$ = Et, 50%

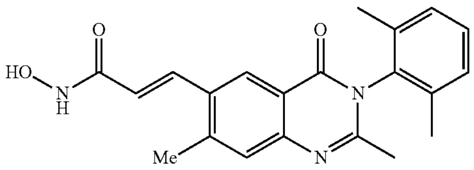

6q: $R_1$ = Me, 69%
6r: $R_1$ = Et, 78%

[a]Reagents and conditions: (a) NIS, AcOH, 85° C., 4 h, 96% (b) (i) acetyl chloride or propionic anhydride, $P(OPh)_3$, 0° C.-rt, 20 min; (ii) 2,6-difluoroaniline, pyridine, MW, 200 W, 20 min; (c) Pd(OAc)2, PPh3, ethyl acrylate, NaOAc, DMA, MW 250 W, 25 min; (d) Pd(dba)3, $[(t\text{-}Bu)_3PH]BF_4$, Me2Zn, THF, MW 115° C., 60 min,; (e) NaOH, NH2OH, MeOH, 0° C.

Example 3

Scheme 1-4[a]

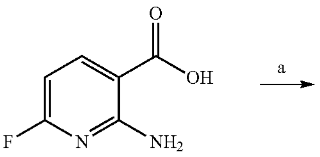

1a

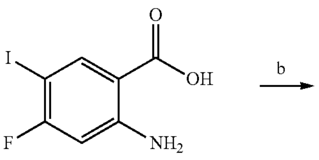

2a

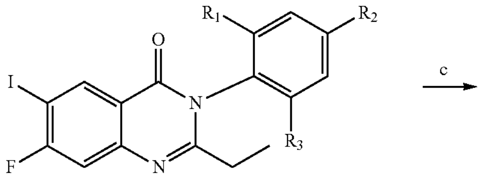

3x: R1 = Br, R2 = F, R3 = Br, 38%
3z: R1 = Br, R2 = H, R3 = Cl, 40%

-continued

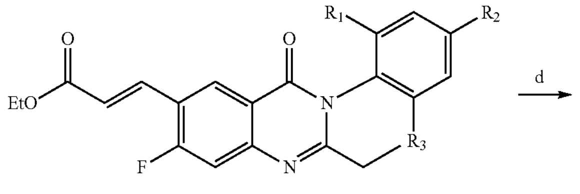

4x: R1 = Br, R2 = F, R3 = Br, 17%
4z: R1 = Br, R2 = H, R3 = Cl, 37%

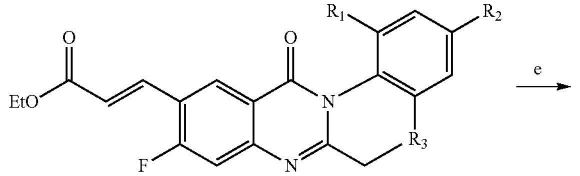

5x: R1 = Me, R2 = F, R3 = Me, 73%
5ac: R1 = Me, R2 = H, R3 = Cl, 59%

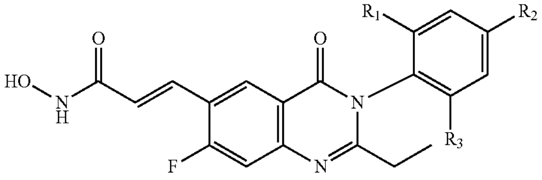

6x: R1 = Me, R2 = F, R3 = Me, 19%
6ac: R1 = Me, R2 = H, R3 = Cl, 16%

[a]Reagents and conditions: (a) NIS, AcOH, 85° C., 4 h, 84% (b) propionic anhydride, $P(OPh)_3$, 0° C.-rt, MW 200 W, 20 min; (ii) 4-fluoro2,6-dimethylaniline, pyridine, MW, 200 W, 20 min; (c) Pd(OAc)2, PPh3, ethyl acrylate, NaOAc, DMA, MW 250 W, 25 min; (d) Pd2(dba)3, $[(t\text{-}Bu)_3PH]BF_4$, Me2Zn, THF, MW 115° C., 40 min,; (e) NaOH, NH2OH, MeOH, 0° C.-rt, 2.5 h

Example 4

Scheme 1-5[a]

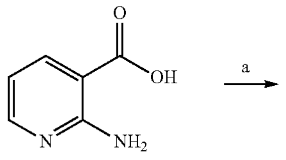

65

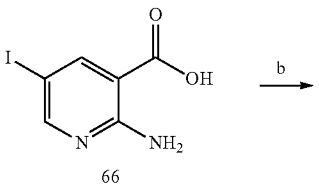

66

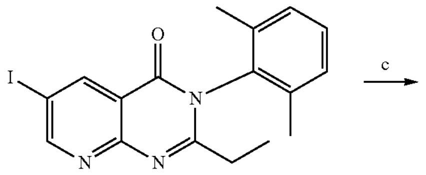

67

-continued

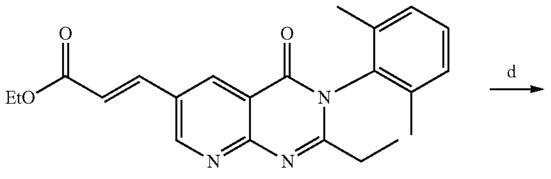

68

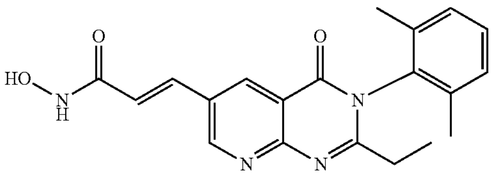

5aj

[a]Reagents and conditions: (a) N-Iodosuccinimide, , AcOH, 90° C., 4 h, 94% (b) (i) propionic anhydride, $P(OPh)_3$, MW 250W, 25 min; (ii) amine, pyridine, 110° C., MW 250 W, 25 min, 58%; (c) $Pd(OAc)_2$, $PPh_3$, ethyl acrylate, NaOAc, DMA, MW 250 W, 25 min, 52%; (d) NaOH, $NH_2OH$, 0-rt., 70%

Example 5

Scheme 1-6[a]

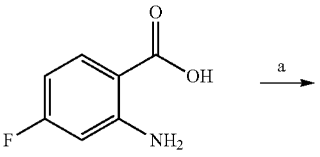

1

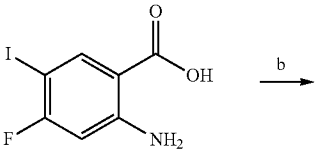

2a

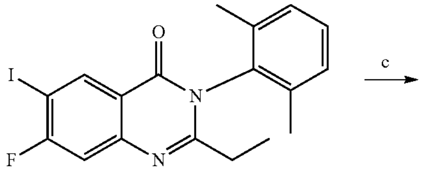

3d

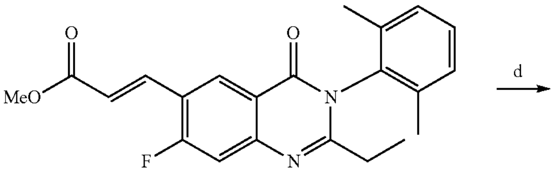

3af

-continued

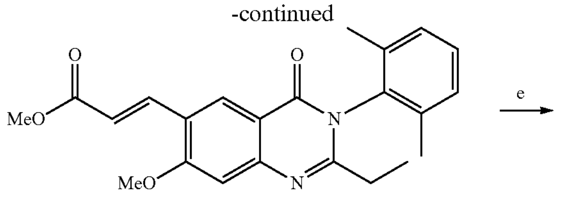

4af

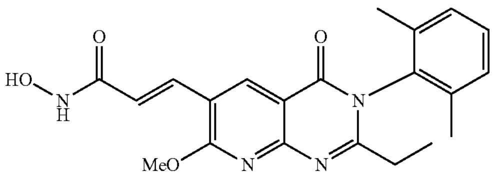

5af

[a]Reagents and conditions: (a) NIS, AcOH, 85° C., 4 h, 84% (b) propionic anhydride, P(OPh)3, 0° C.-rt, MW 250W, 20 min; (ii) 2,4-dimethylaniline, pyridine, MW 250 W, 20 min, 58%; (c) Pd(OAc)2, PPh3, methyl acrylate, NaOAc, DMA, MW 250 W, 25 min, 35%; (d) NaOMe, DMF, MeOH, 80° C., 4 h, 31%; (e) NaOH, NH2OH, MeOH, 0° C.-rt., 4 h, 37%

-continued

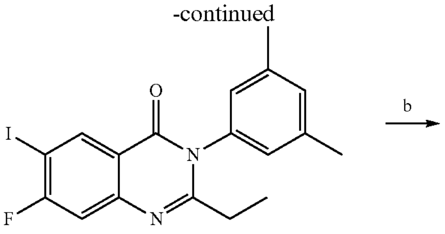

3v

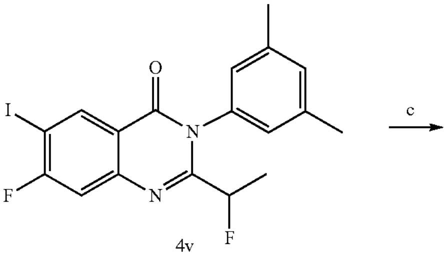

4v

Example 6

Scheme 1-7

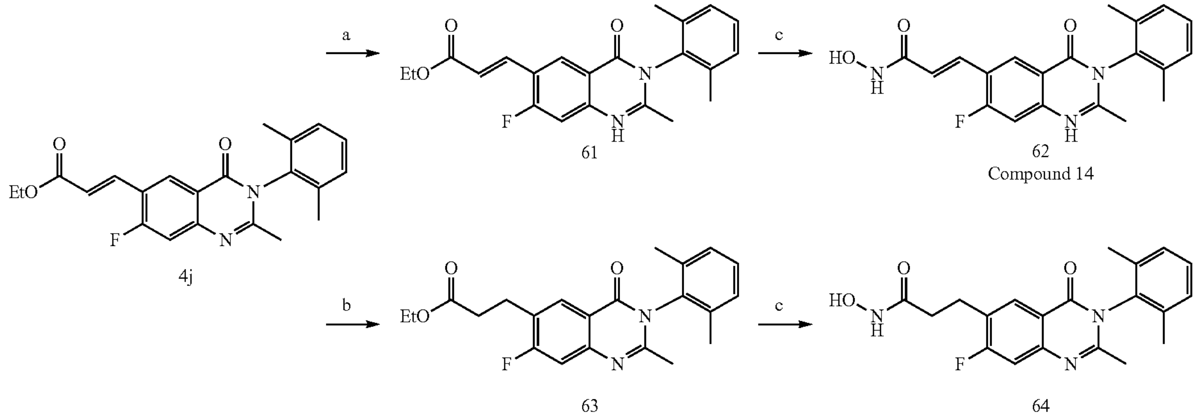

61

62
Compound 14

4j

63

64
Compound 15

[a]Reagents and conditions: (a) NaBH4, THF, MeOH, rt, 4 h, 40%; (b) (i) Ni(OAc)2 4 H2O, (ii) NaBH4, MeOH, DCM, 0° C., 3.5 h, 42%; (c) NaOH, $NH_2OH$, rt

Example 7

Scheme 1-8[a]

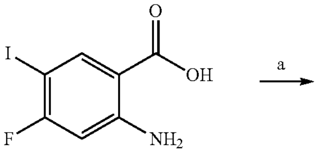

2a

-continued

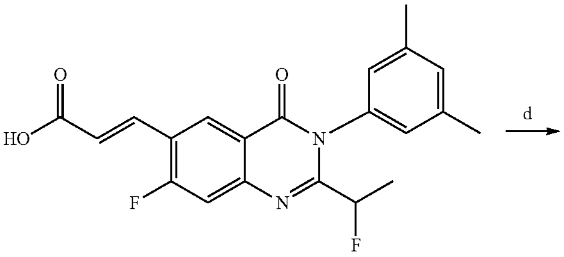

5v

-continued

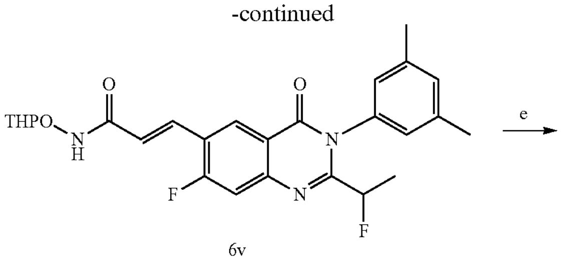

6v

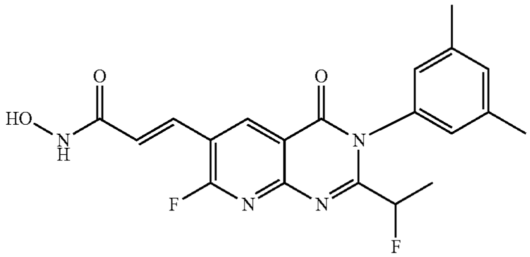

7v

[a]Reagents and conditions: (i) propionic anhydride, $P(OPh)_3$, 0° C.-rt, 20 min; (ii) 2,6-difluoroaniline, pyridine, MW 200 W, 20 min, 53%; (b) selectfluor, DMF, 90° C., 6 h, 43%; (c) acrylic acid, $Pd(OAc)_2$, $[(t\text{-}Bu)_3PH]BF_4$, $Cs_2CO_3$, DMF, MW 200 W, 25 min, 67%; (c) (i) EDCI HCl, HOBt (ii) $NH_2OTHP$, DMF, rt, 18 h, 88%;
(d) TFA, MeOH, 73%

Example 8: 2-amino-4-fluoro-5-iodobenzoic acid (2a)

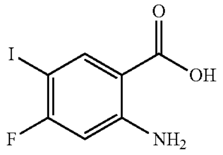 [SMILES: Nc1cc(F)c(I)cc1C(=O)O]

NIS (30.5 g, 135.37 mmol) was added to the solution of 2-amino-4-fluorobenzoic acid (20.0 g, 128.92 mmol) in AcOH (210 mL) at 90° C. for 4 h. After cooling to rt, the reaction mixture was poured into the solution of $NaHSO_3$ (5.2 g, 50.22 mmol) in iced-water (1.2 L) to precipitate the brown solid then filtered. The solid was washed with $H_2O$ (100 mL) and dried in vacuo oven to give the product as brown solid. (35.0 g, 97%). Rf=0.13 (EA/Hex=1:2) ESIMS (+) m/z 282 $[M+H]^+$ Example 9: 6-amino-2-fluoro-3-iodobenzoic acid (2b)

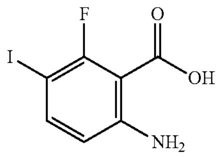 [SMILES: Nc1ccc(I)c(F)c1C(=O)O]

The mixture solution of 2-amino-6-fluorobenzoic acid (7 g, 45.12 mmol), NIS (10.7 g, 47.38 mmol) in AcOH (75 mL) was heated at 95° C. for 1.5 h. After cooling to rt, the reaction mixture was pour into ice-water (200 mL) and the precipitated solid was filtered. The solid was dried in vacuo to give the product as brown solid (12.5 g, 98%).

Example 10: 2-amino-3-fluoro-5-iodobenzoic acid (2c)

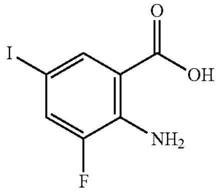 [SMILES: Nc1c(F)cc(I)cc1C(=O)O]

The mixture solution of 2-amino-3-fluorobenzoic acid (7.5 g, 48.35 mmol), NIS (11.42 g, 50.76 mmol) in AcOH (80 mL) was heated at 95° C. for 3.5 h. After cooling to rt, the reaction mixture was poured into the solution of $NaHSO_3$ (1.95 g, 18.83 mmol) in iced-water (450 mL) then filtered. The solid was washed with $H_2O$ (80 mL) then re-dissolved with EtOAc (200 mL). The organic layer was washed with the solution of NaCl (sat. 100 mL×2) and dried over $MgSO_4$. The $MgSO_4$ was removed by filtration and the filtrate was concentrated in vacuo to give the crude solid. The crude was washed with DCM to give the product as brown solid. (8.9 g, 66%). The filtrate was concentrated and wash with DCM again to give the product as brown solid. (0.3 g, 2%) total (9.2 g, 68%) Rf=0.32 (EA/Hex=1:2)

Example 11: 2-amino-4-chloro-5-iodobenzoic acid (2d)

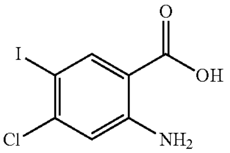

The mixture solution of 2-amino-4-chlorobenzoic acid (5.0 g, 29.24 mmol), NIS (4.2 g, 30.70 mmol) in AcOH (49 mL) was heated at 90° C. for 4.5 h. after cooling to rt., the resulting solution was poured into the iced-solution of NaHSO3 (1.4 g, 13.45 mmol) in H2O (300 mL) to precipitate the solid. The solid was collected and was with H2O (100 mL) and dried in vacuo to give the product as brown solid. (8.3 g, 96%). Rf=0.4 (EA/Hex=1/2)

Example 12: 2-amino-5-iodonicotinic acid (66)

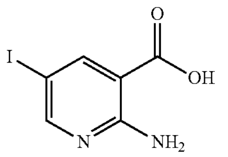 [SMILES: Nc1ncc(I)cc1C(=O)O]

The slurry solution of 2-aminonicotinic acid (4.0 g, 28.96 mmol), NIS (6.8 g, 30.41 mmol) in AcOH (48 mL) was stirred at 90° C. for 4 h. The resulting solution was poured into H2O (600 mL) to precipitate the product. The slurry solution was filtered and the filtered solid was further washed with ether (30 mL) to give the product as brown solid. (7.2 g, 94%)

Example 13: 3-(4-bromophenyl)-2-ethyl-7-fluoro-6-iodoquinazolin-4(3H)-one (3b)

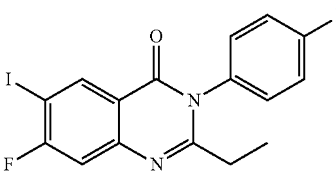

The solution of 2a (5.2 g, 18.50 mmol) in pyridine (25 mL) was added propionic anhydride (3.6 mL, 27.76 mmol) dropwise at 0° C. then stirred at rt. for 20 min. The resulting solution was added $P(OPh)_3$ (6.3 mL, 24.06 mmol) and irritated by MW 250 W 20 min. The reaction mixture was added 4-bromoaniline (4.8 g, 27.76 mmol) and irritated by MW 250 W 20 min. After cooling to rt., the resulting solution was quenched with 3 N HCl (55 mL) until pH=2 and extracted with EA (100 mL×2), $H_2O$ (100 mL). The organic layer was dried over $MgSO_4$ and concentrated to give the crude as brown-dark oil. The crude was purified by precipitate (ether/Hex=1/1) to give the product as brown solid. (1.99 g, 23%). The filtrate was concentrated and precipitated again (ether/Hex=1/1) to give the product as brown solid. (1.99 g, 23%). Total (4.0 g, 46%). Rf=0.4 (EA/Hex=1:3);

2-ethyl-7-fluoro-6-iodo-3-(2-methyl-3-(trifluoromethyl)phenyl)quinazolin-4(3H)-one (3c)

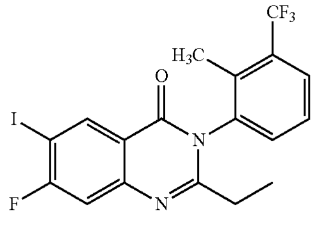 [SMILES: CCc1nc2cc(F)c(I)cc2c(=O)n1-c1cccc(C(F)(F)F)c1C]

The solution of 2a (3.2 g, 11.40 mmol) in pyridine (15 mL) was added propionic anhydride (2.2 mL, 17.12 mmol) dropwise at 0° C. then stirred at rt. for 30 min. The resulting solution was added $P(OPh)_3$ (3.9 mL, 14.84 mmol) and irritated by MW 250 W 20 min. The reaction mixture was added 2-methyl-3-(trifluoromethyl)aniline (3.0 g, 17.12 mmol) and irritated by MW 250 W 20 min. After cooling to rt., the resulting solution was quenched with 3 N HCl (50 mL) until pH=2 and extracted with EA (100 mL×2). The organic layer was dried over $MgSO_4$ and concentrated to give the crude as brown-dark oil. The crude was purified by flash column (¢4.5×8.5, EA/HEX=1/8-1-7) to give the mixture as yellow oil. The yellow was added ether (10 mL) and Hex (5 mL) then put at −20° C. overnight to give the product as yellowish solid. (2.5 g, 46%). The filtrate was concentrated and added Hex (15 mL) and put at −20° C. 3 h to give the product as yellowish solid. (0.5 g, 9%). Total (3.0 g, 55%). Rf=0.63 (EA/Hex=1:2); ESIMS(+) m/z 477 $[M+H]^+$ 3-(2,6-dimethylphenyl)-2-ethyl-7-fluoro-6-iodoquinazolin-4(3H)-one (3d)

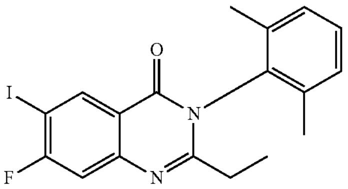 [SMILES: CCc1nc2cc(F)c(I)cc2c(=O)n1-c1c(C)cccc1C]

The solution of 2a (9.0 g, 32.03 mmol) in pyridine (42 mL) was added propionic anhydride (6.2 mL, 48.05 mmol), $P(OPh)_3$ (10.9 mL, 41.64 mmol) and stirred at rt. for 10 mins. The resulting solution was irritated by MW 250 W 20 min. The reaction mixture was added 2,6-dimethylaniline (5.1 mL, 41.64 mmol) and irritated by MW 250 W 20 min. After cooling to rt., the resulting solution was quenched with 3 N HCl (150 mL) until pH=2 and extracted with DCM (100 mL×3). The organic layer was dried over $MgSO_4$ and concentrated to give the crude as orange oil. The crude was precipitated by EA (5 mL), Hex (15 mL) ang sonicated for 2 mins to precipitate the product (clear to slurry). The slurry solution was added Hex (50 mL) during sonication to precipitate the product as orange solid. (8.9 g, 66%). Rf=0.48 (EA/Hex=1:2);

3-(3,5-dimethylphenyl)-2-ethyl-7-fluoro-6-iodoquinazolin-4(3H)-one (3e)

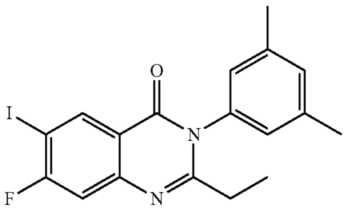 [SMILES: CCc1nc2cc(F)c(I)cc2c(=O)n1-c1cc(C)cc(C)c1]

The solution of 2a (5.0 g, 17.79 mmol) in pyridine (24 mL) was added propionic anhydride (3.4 mL, 26.69 mmol) dropwise at 0° C. then stirred at rt. for 10 min. The resulting solution was added $P(OPh)_3$ (6 mL, 23.13 mmol) nd irritated by MW 250 W 20 min. The reaction mixture was added 3,5-dimethylaniline (3.3 mL, 26.69 mmol) and irritated by MW 250 W 20 min. After cooling to rt., the resulting solution was quenched with 3 N HCl (68 mL) until pH=2 and extracted with DCM (100 mL×2). The organic layer was dried over $MgSO_4$ and concentrated to give the crude as yellowish solid. The solid was further washed with EA/Hex (1/7 mL) to give the product as clear orange solid. (4.0 g, 53%). Rf=0.53 (EA/Hex=1:2);

3-(4-bromo-2-methylphenyl)-2-ethyl-7-fluoro-6-iodoquinazolin-4(3H)-one (3f)

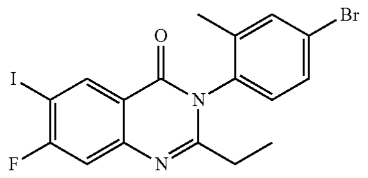 [SMILES: CCc1nc2cc(F)c(I)cc2c(=O)n1-c1ccc(Br)cc1C]

The solution of 2a (5.0 g, 17.79 mmol) in pyridine (24 mL) was added propionic anhydride (3.4 mL, 26.69 mmol) dropwise at 0° C. then stirred at rt. for 10 min. The resulting solution was added $P(OPh)_3$ (6 mL, 23.13 mmol) nd irritated by MW 250 W 20 min. The reaction mixture was added 4-bromo-2-methylaniline (5 g, 26.69 mmol) and irritated by MW 250 W 20 min. After cooling to rt., the resulting solution was quenched with 3 N HCl (68 mL) until pH=2 and extracted with DCM (100 mL×2). The organic layer was dried over $MgSO_4$ and concentrated to give the crude as brown-yellow oil. The crude was added EA/Hex (5/25 mL) and concentrated to give the slurry liquid. The crude was washed with EA/Hex (5/25 mL) to give the product as clear orange solid. (4.5 g, 52%). Rf=0.58 (EA/Hex=1:2);

3-(2,6-diisopropylphenyl)-2-ethyl-7-fluoro-6-iodo-quinazolin-4(3H)-one (3g)

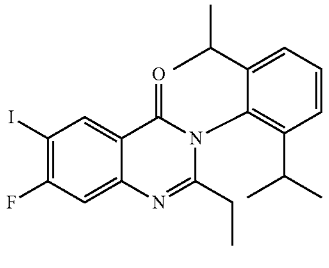 [SMILES: CCc1nc2cc(F)c(I)cc2c(=O)n1-c1c(C(C)C)cccc1C(C)C]

The solution of 2a (5.0 g, 17.79 mmol) in pyridine (24 mL) was added propionic anhydride (3.4 mL, 26.69 mmol) dropwise at 0° C. then stirred at rt. for 10 min. The resulting solution was added $P(OPh)_3$ (6 mL, 23.13 mmol) nd irritated by MW 250 W 20 min. The reaction mixture was added 2,6-diisopropylaniline (7.0 mL, 26.69 mmol) and irritated by MW 250 W 20 min. After cooling to rt., the resulting solution was quenched with 3 N HCl (68 mL) until pH=2 and extracted with DCM (100 mL×2). The organic layer was dried over $MgSO_4$ and concentrated to give the crude as slurry oil. The crude was washed with EA/Hex (3/18 mL) to give the product as white solid. (4.3 g, 50%). Rf=0.5 (EA/Hex=1:2);

3-(2,6-dimethylphenyl)-2-ethyl-8-fluoro-6-iodoquinazolin-4(3H)-one (3m)

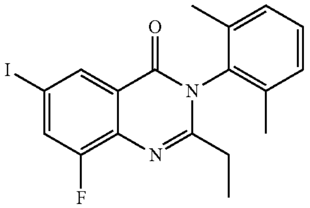

The solution of 2c (4.7 g, 16.72 mmol) in pyridine (22 mL) was added propionic anhydride (3.2 mL, 25.09 mmol) dropwise at 0° C. then stirred at rt. for 10 min. The resulting solution was added $P(OPh)_3$ (5.6 mL, 25.09 mmol) and irritated by MW 250 W 20 min. The reaction mixture was added 2,6-dimethylaniline (2.7 mL, 21.74 mmol) and irritated by MW 250 W 20 min. After cooling to rt., the resulting solution was quenched with 3 N HCl (66 mL) until pH=2 and extracted with DCM (100 mL×2). The organic layer was dried over $MgSO_4$ and concentrated to give the crude as black slurry oil. The crude was filtered to give the product as clear orange solid. (1.21 g, 17%). The filtrate was purified by flash column (¢4.5×7, EA/Hex=1/7-1-6.5) to give the product as yellow oil. The oil was put under −20° C. for 0.5 h to give the product as white solid. (2.5 g, 35%). Total (3.7 g, 52%). Rf=0.6 (EA/Hex=1:2);

3-(4-bromo-2,5-dimethylphenyl)-2-ethyl-7-fluoro-6-iodoquinazolin-4(3H)-one (3s)

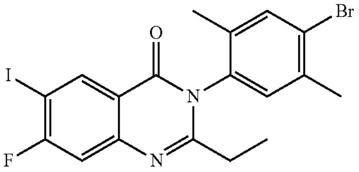 [SMILES: CCc1nc2cc(F)c(I)cc2c(=O)n1-c1cc(C)c(Br)cc1C]

The solution of 2a (5.8 g, 20.60 mmol) in pyridine (27 mL) was added propionic anhydride (4.0 mL, 30.90 mmol) at 0° C. then stirred at rt. for 5 min. The resulting solution was added $P(OPh)_3$ (7 mL, 26.78 mmol) and irritated by MW 250 W 20 min. The reaction mixture was added 4-bromo-2,5-dimethylaniline (5.4 g, 26.78 mmol) and irritated by MW 250 W 20 min. After cooling to rt., the resulting solution was quenched with 3 N HCl (70 mL) until pH=2 and extracted with DCM (100 mL×2). The organic layer was dried over $MgSO_4$ and concentrated to give the crude as brown oil. The crude was purified by flash column (¢4.5×9, EA/Hex=2/15-1/6) to give the product as brown oil. The oil was added Hex (50 mL) and sonicated at rt for 5 min to precipitate the product as white solid. (5.3 g, 51%). Total (5.8 g, 50%). Rf=0.63 (EA/Hex=1:2); ESIMS(+) m/z 501 $[M+H]^+$ 3-(4-bromo-3-methylphenyl)-2-ethyl-7-fluoro-6-iodoquinazolin-4(3H)-one (3t)

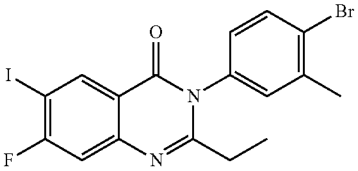 [SMILES: CCc1nc2cc(F)c(I)cc2c(=O)n1-c1ccc(Br)c(C)c1]

The solution of 2a (5.0 g, 17.79 mmol) in pyridine (24 mL) was added propionic anhydride (3.4 mL, 26.69 mmol) at 0° C. then stirred at rt. for 10 min. The resulting solution was added $P(OPh)_3$ (6 mL, 23.13 mmol) and irritated by MW 250 W 20 min. The reaction mixture was added 4-bromo-3-methylaniline (4.3 g, 23.13 mmol) and irritated by MW 250 W 20 min. After cooling to rt., the resulting solution was quenched with 3 N HCl (65 mL) until pH=2 and extracted with DCM (75 mL×2). The organic layer was dried over $MgSO_4$ and concentrated to give the crude as brown slurry oil. The crude was added EA (3 mL), Hex (15 mL), ether (5 mL) and sonicated to precipitate the product as beige solid. (3.3 g, 38%). The filtrate was concentrated and purified by flash column (¢4×8, EA/Hex=1/9-1/7) to give the product as yellow oil. The oil was diluted with EA (5 mL), Hex (50 mL) and put at 0° C. for 18 h to precipitate the product as white solid. (1.2 g, 14%). Total (4.5 g, 52%). Rf=0.53 (EA/Hex=1:2);

3-(2,3-dimethylphenyl)-2-ethyl-7-fluoro-6-iodoquinazolin-4(3H)-one (3u)

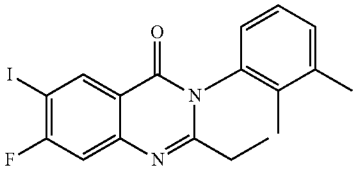 [SMILES: CCc1nc2cc(F)c(I)cc2c(=O)n1-c1cccc(C)c1C]

The solution of 2a (5.0 g, 17.79 mmol) in pyridine (24 mL) was added propionic anhydride (3.4 mL, 26.69 mmol) at 0° C. then stirred at rt. for 10 min. The resulting solution was added $P(OPh)_3$ (6 mL, 23.13 mmol) and irritated by MW 250 W 20 min. The reaction mixture was added 2,3-dimethylaniline hydrochloride (3.6 g, 23.13 mmol) and irritated by MW 250 W 20 min. After cooling to rt., the resulting solution was quenched with 3 N HCl (60 mL) until pH=2 and extracted with DCM (75 mL×2). The organic layer was dried over $MgSO_4$ and concentrated to give the crude as brown slurry oil. The crude was filtered and the filtrate was concentrated and purified by flash column (¢4.5×9, EA/Hex=1/9) to give the product as yellow oil. (4.0 g, 53%). Rf=0.53 (EA/Hex=1:2); ESIMS(+) m/z 423 $[M+H]^+$ 3-(2,5-dimethylphenyl)-2-ethyl-7-fluoro-6-iodoquinazolin-4(3H)-one (3w)

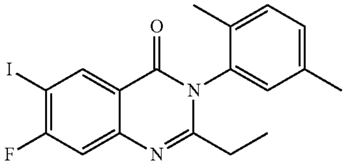 [SMILES: CCc1nc2cc(F)c(I)cc2c(=O)n1-c1cc(C)ccc1C]

The solution of 2a (5.0 g, 17.79 mmol) in pyridine (24 mL) was added propionic anhydride (3.4 mL, 26.69 mmol) dropwise at 0° C. then stirred at rt. for 10 min. The resulting solution was added $P(OPh)_3$ (6 mL, 23.13 mmol) nd irritated by MW 250 W 20 min. The reaction mixture was added 2,5-dimethylaniline (3 mL, 23.13 mmol) and irritated by MW 250 W 20 min. After cooling to rt., the resulting solution was quenched with 3 N HCl (63 mL) until pH=2 and extracted with DCM (75 mL×2). The organic layer was dried over $MgSO_4$ and concentrated to give the crude as brown oil. The crude was purified by flash column (¢4.5×11.5, EA/Hex=1/10-1/5) to give the product as beige solid. (3.2 g, 42%). Rf=0.58 (EA/Hex=1:2);

3-(2,4-dimethylphenyl)-2-ethyl-7-fluoro-6-iodoquinazolin-4(3H)-one (3y)

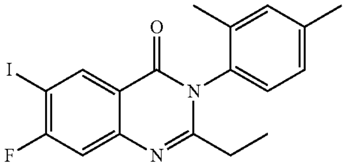 [SMILES: CCc1nc2cc(F)c(I)cc2c(=O)n1-c1ccc(C)cc1C]

The solution of 2a (4.5 g, 16.01 mmol) in pyridine (21 mL) was added propionic anhydride (3.3 mL, 24.02 mmol) then stirred at rt. for 10 min. The resulting solution was added $P(OPh)_3$ (5.4 mL, 20.82 mmol) and irritated by MW 250 W 20 min. The reaction mixture was added 2,4-dimethylaniline (3 mL, 20.82 mmol) and irritated by MW 250 W 20 min. After cooling to rt., the resulting solution was quenched with 3 N HCl (66 mL) until pH=2 and extracted with DCM (75 mL×2), H2O (20 mL). The organic layer was dried over $MgSO_4$ and concentrated to give the crude as yellow oil which was put at rt. overnight to give the product as orange crystal. The crystal was further washed with EA (3 mL), Hex (20 mL) to give the product. (3.5 g, 52%). Rf=0.63 (EA/Hex=1:2);

3-(2-bromo-4-chlorophenyl)-2-ethyl-7-fluoro-6-iodoquinazolin-4(3H)-one (3z)

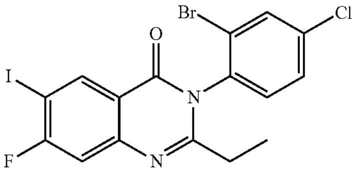 [SMILES: CCc1nc2cc(F)c(I)cc2c(=O)n1-c1ccc(Cl)cc1Br]

The solution of 2a (5.0 g, 17.79 mmol) in pyridine (23 mL) was added propionic anhydride (3.4 mL, 26.69 mmol) dropwise at 0° C. then stirred at rt. for 10 min. The resulting solution was added $P(OPh)_3$ (6 mL, 23.13 mmol) and irritated by MW 250 W 20 min. The reaction mixture was added 2-bromo-4-chloroaniline (4.8 g, 23.13 mmol) and irritated by MW 250 W 20 min. After cooling to rt., the resulting solution was quenched with 3 N HCl (60 mL) until pH=2 and extracted with DCM (75 mL×2). The organic layer was dried over $MgSO_4$ and concentrated to give the crude as brown-green oil. The crude was purified by flash column (¢4.5×8, EA/Hex=1/10) to give the product as yellow oil. The oil was added Hex (50 mL) and sonicated at rt. for 2 min to precipitated the product as white solid. (3.6 g, 40%). Rf=0.58 (EA/Hex=1:2); ESIMS(+) m/z 509 $[M+H]^+$ 2-ethyl-7-fluoro-3-(4-fluoro-2-methylphenyl)-6-iodoquinazolin-4(3H)-one (3aa)

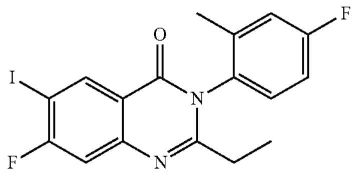 [SMILES: CCc1nc2cc(F)c(I)cc2c(=O)n1-c1ccc(F)cc1C]

The solution of 2a (4.5 g, 16.01 mmol) in pyridine (21 mL) was added propionic anhydride (3.3 mL, 24.02 mmol) then stirred at rt. for 10 min. The resulting solution was added $P(OPh)_3$ (5.4 mL, 20.82 mmol) and irritated by MW 250 W 20 min. The reaction mixture was added 4-fluoro-2-methylaniline (2.3 mL, 20.82 mmol) and irritated by MW 250 W 20 min. After cooling to rt., the resulting solution was quenched with 3 N HCl (60 mL) until pH=2 and extracted with DCM (75 mL×2), H2O (50 mL). The organic layer was dried over $MgSO_4$ and concentrated to give the crude as red-wine oil. The crude was purified by flash column (¢4× 12, EA/Hex=1/10-1/9.5) to give the product as yellow oil. The oil was added Hex (30 mL), ether (3 mL) and put at −20° C. overnight to give the product as beige crystal. (5.8 g, 85%). Rf=0.65 (EA/Hex=1:2);

3-(4-bromo-2-fluorophenyl)-2-ethyl-7-fluoro-6-iodo-quinazolin-4(3H)-one (3ab)

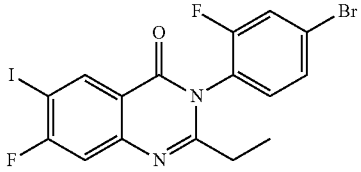 [SMILES: CCc1nc2cc(F)c(I)cc2c(=O)n1-c1ccc(Br)cc1F]

The solution of 2a (5.0 g, 17.79 mmol) in pyridine (23 mL) was added propionic anhydride (3.4 mL, 26.69 mmol) dropwise at 0° C. then stirred at rt. for 10 min. The resulting solution was added $P(OPh)_3$ (6 mL, 23.13 mmol) and irritated by MW 250 W 20 min. The reaction mixture was added 4-bromo-2-fluoroaniline (4.4 g, 23.13 mmol) and irritated by MW 250 W 20 min. After cooling to rt., the resulting solution was quenched with 3 N HCl (65 mL) until pH=2 and extracted with DCM (75 mL×2), H2O (50 mL). The organic layer was dried over $MgSO_4$ and concentrated to give the crude as yellow oil. The crude was purified by flash column (¢4.5×11, EA/Hex=1/10-1-8) to give the product as yellow slurry oil. The oil was added Hex (50 mL) and sonicated at rt. for 2 min to precipitated the product as white solid. (4.5 g, 52%). Rf=0.53 (EA/Hex=1:2);

2-ethyl-7-fluoro-6-iodo-3-mesitylquinazolin-4(3H)-one (3ad)

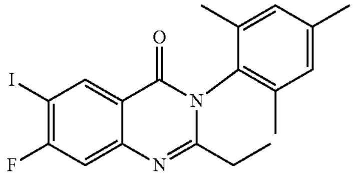 [SMILES: CCc1nc2cc(F)c(I)cc2c(=O)n1-c1c(C)cc(C)cc1C]

The solution of 2a (5.0 g, 17.79 mmol) in pyridine (24 mL) was added propionic anhydride (3.4 mL, 26.69 mmol), $P(OPh)_3$ (6.0 mL, 23.13 mmol) and stirred at rt. for 10 min. The resulting solution was irritated by MW 250 W 20 min. The reaction mixture was added 2,4,6-trimethylaniline (3.3 mL, 23.13 mmol) and irritated by MW 250 W 20 min. After cooling to rt., the resulting solution was quenched with 2 N HCl (110 mL) until pH=2 and extracted with DCM (75 mL×2). The organic layer was dried over $MgSO_4$ and concentrated to give the crude as orange oil. The crude was purified by flash column (¢4.5×10, EA/Hex=1/10-1/9) to give the product as yellow oil and directly to the next step. (9.2 g, >100%). Rf=0.6 (EA/Hex=1:2);

3-(4-bromo-2,6-dimethylphenyl)-2-ethyl-7-fluoro-6-iodoquinazolin-4(3H)-one (3ae)

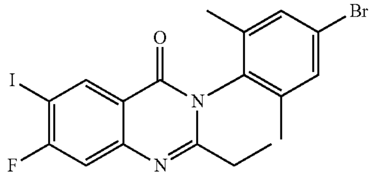 [SMILES: CCc1nc2cc(F)c(I)cc2c(=O)n1-c1c(C)cc(Br)cc1C]

The solution of 2a (8.0 g, 28.47 mmol) in pyridine (38 mL) was added propionic anhydride (5.5 mL, 42.70 mmol), $P(OPh)_3$ (9.7 mL, 37.01 mmol) and stirred at rt. for 10 min. The resulting solution was irritated by MW 250 W 20 min. The reaction mixture was added 4-bromo-2,6-dimethylaniline (7.4 g, 37.01 mmol) and irritated by MW 250 W 20 min. After cooling to rt., the resulting solution was quenched with 2 N HCl (190 mL) until pH=2 and extracted with DCM (100 mL×2). The slurry organic layer was filtered and the filtrate was purified by flash column (¢5.5×8, EA/Hex=1/10-1/8) to give the product as yellow oil. The oil was added Hex (30 mL) and sonicated to precipitate the product as white solid. (1.5 g, 11%). Rf=0.58 (EA/Hex=1:2);

2-ethyl-7-fluoro-6-iodo-3-phenylquinazolin-4(3H)-one (3ag)

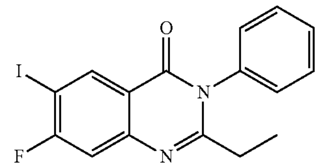 [SMILES: CCc1nc2cc(F)c(I)cc2c(=O)n1-c1ccccc1]

The solution of 2a (5.0 g, 17.79 mmol) in pyridine (24 mL) was added propionic anhydride (3.4 mL, 26.69 mmol), $P(OPh)_3$ (6.0 mL, 23.13 mmol) and stirred at rt. for 10 min. The resulting solution was irritated by MW 250 W 20 min. The reaction mixture was added aniline (2.1 mL, 23.13 mmol) and irritated by MW 250 W 20 min. After cooling to rt., the resulting solution was quenched with 3 N HCl (68 mL) until pH=2 and extracted with DCM (75 mL×2), H2O (20 mL). The organic layer was dried over $MgSO_4$ and concentrated to give the crude as yellow oil. The crude was purified by flash column (¢4.5×10, EA/HEX=1/10-1/8) to give the product as beige solid. The solid was washed with Hex (50 mL) to give the product as beige solid. (4.1 g, 58%). Rf=0.5 (EA/Hex=1:2);

2-ethyl-7-fluoro-6-iodo-3-(4-methoxy-2-methylphenyl)quinazolin-4(3H)-one (3ah)

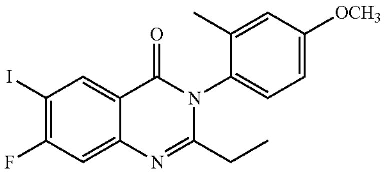 [SMILES: CCc1nc2cc(F)c(I)cc2c(=O)n1-c1ccc(OC)cc1C]

The solution of 2a (5.0 g, 17.79 mmol) in pyridine (23 mL) was added propionic anhydride (3.4 mL, 26.69 mmol), $P(OPh)_3$ (6.0 mL, 23.13 mmol) and stirred at rt. for 10 min. The resulting solution was irritated by MW 250 W 20 min. The reaction mixture was added 4-methoxy-2-methylaniline (3 mL, 23.13 mmol) and irritated by MW 250 W 20 min. After cooling to rt., the resulting solution was quenched with 3 N HCl (68 mL) until pH=2 and extracted with DCM (100 mL×2), H2O (20 mL). The organic layer was dried over $MgSO_4$ and concentrated to give the crude as wine oil. The crude was purified by flash column (¢4.5×10, EA/HEX=1/10-1/8) to give the product as yellow oil. The oil was added Hex (50 mL) and sonicated to precipitated the product as white solid. (2.6 g, 34%). Rf=0.43 (EA/Hex=1:2);

2-ethyl-8-fluoro-3-(4-fluoro-2-methylphenyl)-6-iodoquinazolin-4(3H)-one (3ai)

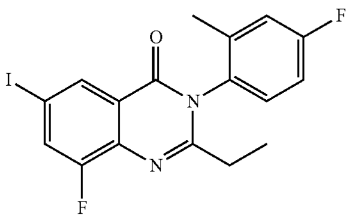 [SMILES: CCc1nc2c(F)cc(I)cc2c(=O)n1-c1ccc(F)cc1C]

The solution of 2c (4.6 g, 16.37 mmol) in pyridine (22 mL) was added propionic anhydride (3.1 mL, 24.55 mmol), $P(OPh)_3$ (5.5 mL, 21.28 mmol) and stirred at rt. for 10 min. The resulting solution was irritated by MW 250 W 20 min. The reaction mixture was added 4-fluoro-2-methylaniline (2.4 mL, 21.28 mmol) and irritated by MW 250 W 20 min. After cooling to rt., the resulting solution was quenched with 3 N HCl (62 mL) until pH=2 and extracted with DCM (100 mL×2), H2O (50 mL). The organic layer was dried over $MgSO_4$ and concentrated to give the crude as wine red solid. The solid was washed with ether (10 mL) to give the product as rose pink solid. (5.2 g, 77%). Rf=0.58 (EA/Hex=1:2);

3-(2,6-dimethylphenyl)-2-ethyl-6-iodopyrido[2,3-d]pyrimidin-4(3H)-one (67)

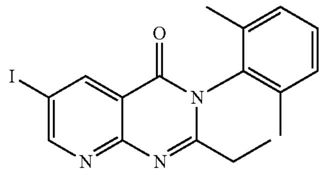 [SMILES: CCc1nc2ncc(I)cc2c(=O)n1-c1c(C)cccc1C]

The solution of 66 (4.0 g, 15.15 mmol) in pyridine (20 mL) was added propionic anhydride (2.9 mL, 22.73 mmol), $P(OPh)_3$ (5.1 mL, 19.70 mmol) and stirred at rt. for 10 min. The resulting solution was irritated by MW 250 W 20 min. The reaction mixture was added 2,6-dimethylaniline (2.4 mL, 19.70 mmol) and irritated by MW 250 W 20 min. After cooling to rt., the resulting solution was quenched with 2 N HCl (100 mL) until pH=2 and extracted with DCM (75 mL×2). The organic layer was dried over $MgSO_4$ and concentrated to give the crude as brown oil. The crude was purified by flash column (¢4.5×10, EA/HEX=1/6-EA/DCM/Hex=1/7/12) to give the product as yellow crystal. The solid was washed with Hex (20 mL) to give the product as white crystal. (3.5 g, 58%). Rf=0.25 (EA/Hex=1:2);

3-(2,6-diisopropylphenyl)-7-fluoro-6-iodo-2-methylquinazolin-4(3H)-one (3h)

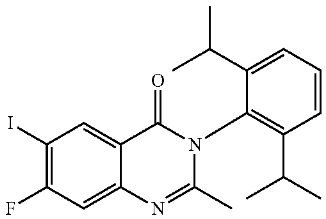 [SMILES: Cc1nc2cc(F)c(I)cc2c(=O)n1-c1c(C(C)C)cccc1C(C)C]

The solution of 2a (7.0 g, 24.91 mmol) in pyridine (33 mL) was added acetyl chloride (2.7 mL, 37.37 mmol) dropwise at 0° C. then stirred at rt. for 10 min. The resulting solution was added $P(OPh)_3$ (8.5 mL, 32.38 mmol) and irritated by MW 250 W 20 min. The reaction mixture was added 2,6-diisopropylaniline (7.0 mL, 37.37 mmol) and irritated by MW 250 W 20 min. After cooling to rt., the resulting solution was quenched with 3 N HCl (115 mL) until pH=2 and extracted with EA (100 mL), DCM (100 mL×2). The organic layer was dried over $MgSO_4$ and concentrated to give the crude. The crude was washed with (EA/ether=1/3) and filtered to give the product as orange solid. (4.3 g, 37%). The filtrate was concentrated and precipitated again EA/ether=1/3) to give the product as brown solid. (1.48 g, 13%). Total (5.8 g, 50%). Rf=0.43 (EA/Hex=1:2); ESIMS(+) m/z 465 [M+H]$^+$ 3-(2,6-dichlorophenyl)-7-fluoro-6-iodo-2-methylquinazolin-4(3H)-one (3i)

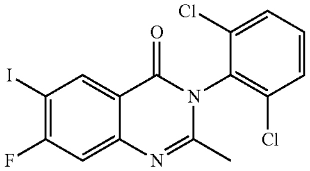 [SMILES: Cc1nc2cc(F)c(I)cc2c(=O)n1-c1c(Cl)cccc1Cl]

The solution of 2a (6.0 g, 21.35 mmol) in pyridine (28 mL) was added acetyl chloride (2.3 mL, 32.03 mmol) dropwise at 0° C. then stirred at rt. for 15 min. The resulting solution was added P(OPh)$_3$ (7 mL, 27.76 mmol) nd irritated by MW 250 W 20 min. The reaction mixture was added 2,6-dichlorolaniline (5.2 g, 32.03 mmol) and irritated by MW 250 W 20 min. After cooling to rt., the resulting solution was quenched with 3 N HCl (80 mL) until pH=2 and extracted with DCM (75 mL×3), H2O (75 mL). The organic layer was dried over MgSO$_4$ and concentrated to give the crude. The crude was purified by flash column (¢4.5×8, EA/Hex=1/7-1/5) to give the product as yellowish solid. (5 g, 52%). Rf=0.35 (EA/Hex=1:2);

3-(2,6-dimethylphenyl)-7-fluoro-6-iodo-2-methylquinazolin-4(3H)-one (3j)

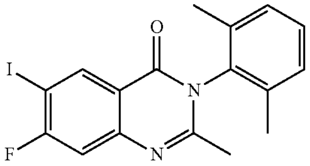 [SMILES: Cc1cccc(C)c1-n1c(C)nc2cc(F)c(I)cc2c1=O]

The solution of 2a (5.0 g, 17.79 mmol) in pyridine (24 mL) was added acetyl chloride (1.9 mL, 26.69 mmol) dropwise at 0° C. then stirred at rt. for 20 min. The resulting solution was added P(OPh)3 (6 mL, 23.13 mmol) nd irritated by MW 250 W 20 min. The reaction mixture was added 2,6-dimethylaniline (3.3 mL, 26.69 mmol) and irritated by MW 250 W 20 min. After cooling to rt., the resulting solution was quenched with 3 N HCl (80 mL) until pH=2 and extracted with DCM (100 mL×2), NaCl (sat. 75 mL), H2O (5 mL). The organic layer was dried over MgSO4 and concentrated to give the crude as dark oil. The crude was added ether/Hex (3/3 mL) and put under −20° C. overnight to get the clear orange solid. (2.7 g, 37%) The filtrate was further purified by flash column (¢4.5×8, EA/HEX=1/8-1/6.5) to give the product as yellow oil. The oil was precipitated by ether/Hex (5/5 mL) and put under −20° C. for 2 h to give the product as white solid. (2 g, 28%). Total (4.7 g, 65%) Rf=0.38 (EA/Hex=1:2);

3-(2,6-dimethylphenyl)-5-fluoro-6-iodo-2-methylquinazolin-4(3H)-one (3k)

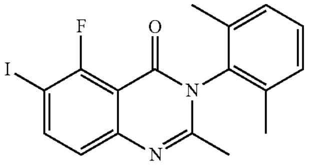 [SMILES: Cc1cccc(C)c1-n1c(C)nc2ccc(I)c(F)c2c1=O]

The solution of 2b (5.0 g, 17.79 mmol) in pyridine (24 mL) was added acetyl chloride (1.9 mL, 26.69 mmol) dropwise at 0° C. then stirred at rt. for 20 min. The resulting solution was added P(OPh)$_3$ (6 mL, 23.13 mmol) nd irritated by MW 250 W 20 min. The reaction mixture was added 2,6-diisopropylaniline (7.0 mL, 37.37 mmol) and irritated by MW 250 W 20 min. After cooling to rt., the resulting solution was quenched with 3 N HCl until pH=2 and extracted with DCM (100 mL×2). The organic layer was dried over MgSO$_4$ and concentrated to give the crude as dark oil. The crude was purified by flash column (¢4.5×9, EA/HEX=1/5-1/3) to give the product as yellow solid. The solid was washed with ether (30 mL) to give the product as yellowish solid. (2.5 g, 35%). Rf=0.25 (EA/Hex=1:2); ESIMS(+) m/z 431 [M+Na]$^+$ 3-(2,6-dimethylphenyl)-8-fluoro-6-iodo-2-methylquinazolin-4(3H)-one (3l)

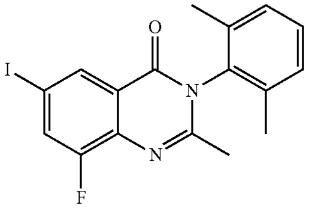 [SMILES: Cc1cccc(C)c1-n1c(C)nc2c(F)cc(I)cc2c1=O]

The solution of 2c (4.5 g, 16.01 mmol) in pyridine (21 mL) was added acetic chloride (1.7 mL, 24.02 mmol) dropwise at 0° C. then stirred at rt. for 10 min. The resulting solution was added P(OPh)$_3$ (5.4 mL, 20.81 mmol) and irritated by MW 250 W 20 min. The reaction mixture was added 2,6-dimethylaniline (2.6 mL, 20.81 mmol) and irritated by MW 250 W 20 min. After cooling to rt., the resulting solution was quenched with 3 N HCl (60 mL) until pH=2 and extracted with DCM (100 mL×2). The organic layer was dried over MgSO$_4$ and concentrated to give the crude as brown oil. The crude was added EA (3 mL), ether (20 mL), Hex (5 mL) and concentrated to give the product as clear orange solid. (2.3 g, 35%) The filtrate was purified by column (¢4.5×6, EA/Hex=1/7-1-6) to give the product as yellow oil. The oil was added ether (20 mL) and put under −20° C. overnight to give the white solid. (1.9 g, 29%). Total (4.2 g, 64%). Rf=0.6 (EA/Hex=1:2);

3-(2,6-difluorophenyl)-7-fluoro-6-iodo-2-methylquinazolin-4(3H)-one (3n)

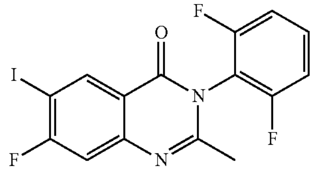 [SMILES: Cc1nc2cc(F)c(I)cc2c(=O)n1-c1c(F)cccc1F]

The solution of 2a (5 g, 17.79 mmol) in pyridine (23 mL) was added acetic chloride (1.9 mL, 26.69 mmol) dropwise at 0° C. then stirred at rt. for 20 min. The resulting solution was added $P(OPh)_3$ (6 mL, 23.13 mmol) and irritated by MW 250 W 20 min. The reaction mixture was added 2,6-difluoroaniline (2.7 mL, 23.13 mmol) and irritated by MW 250 W 20 min. After cooling to rt., the resulting solution was quenched with 3 N HCl (60 mL) until pH=2 and extracted with $CHCl_3$ (100 mL×2), $H_2O$ (50 mL). The organic layer was dried over $MgSO_4$ and concentrated to give the crude as brown slurry oil. The oil was wash with ether (10 mL) to give the product as orange solid. (4.1 g, 56%). The filtrate was purified by flash column (¢4.5×7.5, EA/Hex=1-7) to give the product as white solid. (0.9 g, 12%). Total (5.0 g, 68%). Rf=0.45 (EA/Hex=1:2);

3-(2,6-difluorophenyl)-2-ethyl-7-fluoro-6-iodoquinazolin-4(3H)-one (3o)

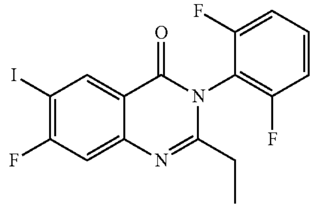 [SMILES: CCc1nc2cc(F)c(I)cc2c(=O)n1-c1c(F)cccc1F]

The solution of 2a (5 g, 17.79 mmol) in pyridine (23 mL) was added propionic anhydride (3.4 mL, 26.69 mmol) dropwise at 0° C. then stirred at rt. for 10 min. The resulting solution was added $P(OPh)_3$ (6 mL, 23.13 mmol) and irritated by MW 250 W 20 min. The reaction mixture was added 2,6-difluoroaniline (2.7 mL, 23.13 mmol) and irritated by MW 250 W 20 min. After cooling to rt., the resulting solution was quenched with 3 N HCl (68 mL) until pH=2 and extracted with DCM (100 mL×2). The organic layer was dried over $MgSO_4$ and concentrated to give the crude as black oil. The crude was purified by flash column (¢4.5×8, EA/Hex=1/7-1-6) to give the product as yellow oil. The oil was added Hex (35 mL) and sonicated at rt. for 1 min to precipitated the product as white solid. (3.1 g, 40%). Rf=0.45 (EA/Hex=1:2);

3-(3,5-dimethylphenyl)-7-fluoro-6-iodo-2-methylquinazolin-4(3H)-one (3p)

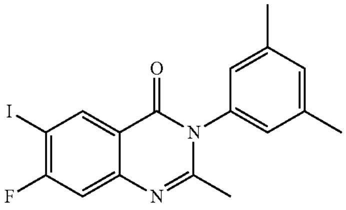 [SMILES: Cc1cc(C)cc(-n2c(C)nc3cc(F)c(I)cc3c2=O)c1]

The mixture solution of 2a (5.0 g, 17.79 mmol) in pyridine (23 mL) was added acetyl chloride (1.9 mL, 26.69 mmol) dropwise at 0° C. then stirred at rt. for 10 min. The resulting solution was added $P(OPh)_3$ (6 mL, 23.13 mmol) and irritated by MW 250 W 20 min. The reaction mixture was added 3,5-dimethylaniline (2.9 mL, 23.13 mmol) and irritated by MW 250 W 20 min. After cooling to rt., the resulting solution was quenched with 3 N HCl (65 mL) until pH=2 and extracted with DCM (75 mL×2). The organic layer was dried over $MgSO_4$ and concentrated to give the crude as orange solid. The crude was washed with EA/Hex (30/10 mL) and sonicated at rt. for 3 min to give the product as orange solid. (4.2 g, 58%). Rf=0.0.5 (EA/Hex=1:2);

7-chloro-3-(2,6-dimethylphenyl)-6-iodo-2-methylquinazolin-4(3H)-one (3q)

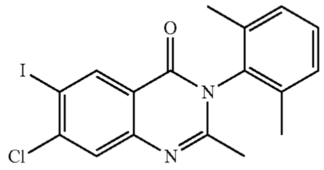 [SMILES: Cc1cccc(C)c1-n1c(C)nc2cc(Cl)c(I)cc2c1=O]

The mixture solution of 2d (5.0 g, 16.84 mmol) in pyridine (22 mL) was added acetyl chloride (1.8 mL, 25.26 mmol) dropwise at 0° C. then stirred at rt. for 15 min. The resulting solution was added $P(OPh)_3$ (6 mL, 21.89 mmol) and irritated by MW 250 W 20 min. The reaction mixture was added 2,6-dimethylaniline (2.7 mL, 21.89 mmol) and irritated by MW 250 W 20 min. After cooling to rt., the resulting solution was quenched with 3 N HCl (68 mL) until pH=2 and extracted with DCM (75 mL×2). The organic layer was dried over $MgSO_4$ and concentrated to give the crude as brown oil. The crude was purified by flash column (¢4.5×7.5, DCM/Hex=3/4–EA/Hex=1/4) to give the product as yellow oil. (>100%). Rf=0.53 (EA/Hex=1:2);

7-chloro-3-(2,6-dimethylphenyl)-2-ethyl-6-iodoquinazolin-4(3H)-one (3r)

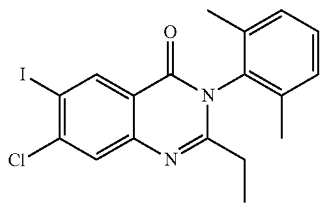 [SMILES: CCc1nc2cc(Cl)c(I)cc2c(=O)n1-c1c(C)cccc1C]

The mixture solution of 2d (6.2 g, 20.74 mmol) in pyridine (27 mL) was added propionic anhydride (4 mL, 31.11 mmol) dropwise at 0° C. then stirred at rt. for 10 min. The resulting solution was added $P(OPh)_3$ (7 mL, 26.96 mmol) and irritated by MW 250 W 20 min. The reaction mixture was added 2,6-dimethylaniline (3.8 mL, 31.11 mmol) and irritated by MW 250 W 20 min. After cooling to rt., the resulting solution was quenched with 3 N HCl (70 mL) until pH=2 and extracted with DCM (75 mL×2). The organic layer was dried over $MgSO_4$ and concentrated to give the crude as brown-dark oil. The crude was purified by precipitate (EA/Hex=1/7) to give the product as white solid. (3 g, 33%). The filtrate was concentrated and purified by flash column (¢4.5×6, EA/Hex=1/8) to give the product as brown solid. (0.9 g, 10%). Total (3.9 g, 43%). Rf=0.55 (EA/Hex=1:2);

(E)-ethyl 3-(3-(4-bromophenyl)-2-ethyl-7-fluoro-4-oxo-3,4-dihydroquinazolin-6-yl)acrylate (4b)

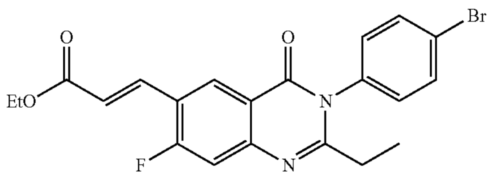

The reaction mixture of 3b (4.0 g, 8.48 mmol), $Pd(OAc)_2$ (0.1 g, 0.43 mmol), $PPh_3$ (0.2 g, 0.85 mmol), NaOAc (1.0 g, 12.71 mmol), ethyl acrylate (1.4 mL, 12.71 mmol) in DMA (14 mL) was irritated by MW 250 W 20 min. After cooling to rt., the resulting solution was filtered and extracted with EtOAc (100 mL×3) and saturated NaCl (100 mL). The organic layer was dried over $MgSO_4$, filtered and concentrated in vacuo to give the crude as dark oil. The crude was purified by flash column (¢4.5×10.5, EA/HEX=1/3) to give the mixture solid. The mixture solid was further washed with ether (10 mL) to give the product as orange solid. (1.26 g, 33%). Rf=0.6 (EA/Hex=1:2);

(E)-ethyl 3-(2-ethyl-7-fluoro-3-(2-methyl-3-(trifluoromethyl)phenyl)-4-oxo-3,4-dihydroquinazolin-6-yl) acrylate (4c)

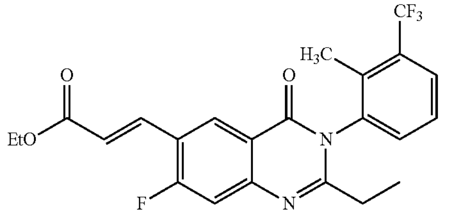 [SMILES: CCOC(=O)/C=C/c1cc2c(=O)n(-c3cccc(C(F)(F)F)c3C)c(CC)nc2cc1F]

The reaction mixture of 3c (3.0 g, 6.30 mmol), $Pd(OAc)_2$ (0.07 g, 0.32 mmol), $PPh_3$ (0.2 g, 0.63 mmol), NaOAc (0.8 g, 9.45 mmol), ethyl acrylate (1 mL, 9.45 mmol) in DMA (12 mL) was irritated by MW 250 W 25 min. After cooling to rt., the resulting solution was diluted with DCM and filtered. The filtrate was extracted with DCM (100 mL×2) and saturated NaCl (75 mL). The organic layer was dried over $MgSO_4$, filtered and concentrated in vacuo to give the crude as dark oil. The crude was purified by precipitate (MeOH 40 mL) to give the product as brown solid (1.6 g, 58%). The filtrate was concentrated and precipitated with ether to give the product as yellow solid. (0.1 g, 4%). Total (1.7 g, 61%); Rf=0.5 (EA/Hex=1:2); ESIMS(+) m/z 471 $[M+Na]^+$ (E)-ethyl 3-(3-(2,6-dimethylphenyl)-2-ethyl-7-fluoro-4-oxo-3,4-dihydroquinazolin-6-yl)acrylate (4d)

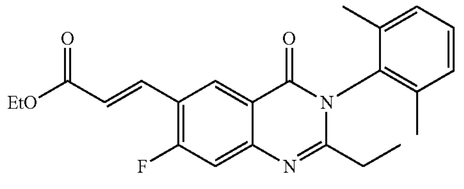 [SMILES: CCOC(=O)/C=C/c1cc2c(=O)n(-c3c(C)cccc3C)c(CC)nc2cc1F]

The reaction mixture of 3d (5.2 g, 12.32 mmol), $Pd(OAc)_2$ (0.1 g, 0.62 mmol), $PPh_3$ (0.3 g, 1.23 mmol), NaOAc (1.5 g, 18.48 mmol), ethyl acrylate (1.4 mL, 13.55 mmol) in DMA (24 mL) was irritated by MW 250 W 25 min. After cooling to rt., the resulting solution was filtered. The filtrate was extracted with DCM (100 mL×2) and saturated NaCl (sat. 100 mL). The organic layer was dried over $MgSO_4$, filtered and concentrated in vacuo to give the crude as brown solid. The crude was washed with MeOH (50 mL) to give the product as brown solid. (3.1 g, 64%).; Rf=0.55 (EA/Hex=1:2);

(E)-ethyl 3-(3-(3,5-dimethylphenyl)-2-ethyl-7-fluoro-4-oxo-3,4-dihydroquinazolin-6-yl)acrylate (4e)

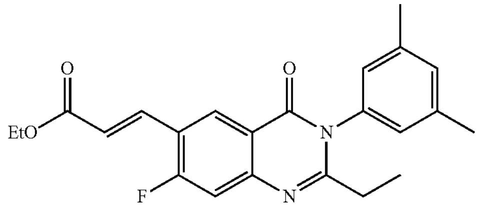 [SMILES: CCOC(=O)/C=C/c1cc2c(=O)n(-c3cc(C)cc(C)c3)c(CC)nc2cc1F]

The reaction mixture of 3e (4.0 g, 9.48 mmol), $Pd(OAc)_2$ (0.1 g, 0.47 mmol), $PPh_3$ (0.3 g, 0.95 mmol), NaOAc (1.2 g, 14.22 mmol), ethyl acrylate (1 mL, 10.43 mmol) in DMA (19 mL) was irritated by MW 250 W 25 min. After cooling to rt., the resulting solution was diluted with DCM and filtered. The filtrate was extracted with DCM (100 mL×2) and saturated NaCl (sat. 100 mL). The organic layer was dried over $MgSO_4$, filtered and concentrated in vacuo to give the crude as dark solid. The crude was washed with MeOH (50 mL×2) to give the product as brown solid. (2.4 g, 64%); Rf=0.5 (EA/Hex=1:2);

(E)-ethyl 3-(3-(4-bromo-2-methylphenyl)-2-ethyl-7-fluoro-4-oxo-3,4-dihydroquinazolin-6-yl)acrylate (4f)

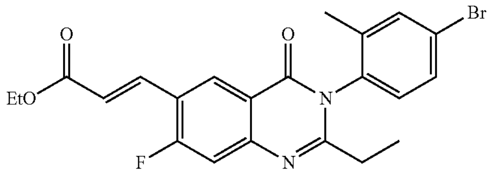

The reaction mixture of 3f (4.1 g, 8.38 mmol), $Pd(OAc)_2$ (0.1 g, 0.42 mmol), $PPh_3$ (0.2 g, 0.84 mmol), NaOAc (1.0 g, 12.56 mmol), ethyl acrylate (1 mL, 12.56 mmol) in DMA (16 mL) was irritated by MW 250 W 25 min. After cooling to rt., the resulting solution was diluted with DCM and filtered. The filtrate was extracted with DCM (75 mL×2) and saturated NaCl (sat. 75 mL). The organic layer was dried over $MgSO_4$, filtered and concentrated in vacuo to give the crude as dark oil. The crude was purified by flash column (¢4.5×8, DCM/Hex=2/1) to give the product as brown solid. (2.0 g, 52%); Rf=0.45 (EA/Hex=1:2);

(E)-ethyl 3-(3-(2,6-diisopropylphenyl)-2-ethyl-7-fluoro-4-oxo-3,4-dihydroquinazolin-6-yl)acrylate (4g)

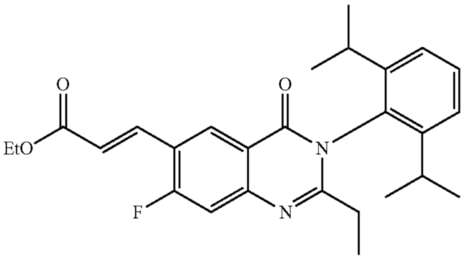 [SMILES: CCOC(=O)/C=C/c1cc2c(=O)n(-c3c(C(C)C)cccc3C(C)C)c(CC)nc2cc1F]

The reaction mixture of 3g (4.3 g, 8.97 mmol), $Pd(OAc)_2$ (0.1 g, 0.45 mmol), $PPh_3$ (0.2 g, 0.90 mmol), NaOAc (1.1 g, 13.46 mmol), ethyl acrylate (1 mL, 9.87 mmol) in DMA (18 mL) was irritated by MW 250 W 25 min. After cooling to rt., the resulting solution was diluted with DCM and filtered. The filtrate was extracted with DCM (75 mL×2), H2O (20 mL) and saturated NaCl (sat. 100 mL). The organic layer was dried over $MgSO_4$, filtered and concentrated in vacuo to give the crude as dar-brown solid. The crude was washed with MeOH (25 mL) and filtered to give the product as orange solid. (2.5 g, 62%); Rf=0.55 (EA/Hex=1:2);

(E)-ethyl 3-(3-(2,6-dimethylphenyl)-2-ethyl-8-fluoro-4-oxo-3,4-dihydroquinazolin-6-yl)acrylate (4m)

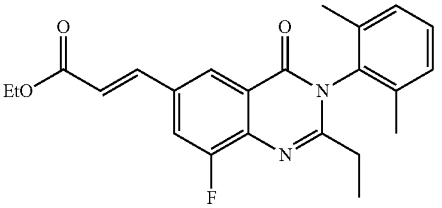 [SMILES: CCOC(=O)/C=C/c1cc(F)c2nc(CC)n(-c3c(C)cccc3C)c(=O)c2c1]

The reaction mixture of 3m (3.7 g, 8.77 mmol), $Pd(OAc)_2$ (0.1 g, 0.43 mmol), $PPh_3$ (0.2 g, 0.88 mmol), NaOAc (1.1 g, 13.15 mmol), ethyl acrylate (1.0 mL, 9.64 mmol) in DMA (17 mL) was irritated by MW 250 W 25 min. After cooling to rt., the resulting solution was diluted with DCM and filtered. The filtrate was extracted with DCM (100 mL×2) and saturated NaCl (sat. 100 mL). The organic layer was dried over $MgSO_4$, filtered and concentrated in vacuo to give the crude as black oil. The crude was purified by flash column (¢4.5×8, EA/HEX=1/7-1/6) to give the product as orange foam. (2.9 g, 84%). Rf=0.4 (EA/Hex=1:2);

(E)-ethyl 3-(3-(4-bromo-2,5-dimethylphenyl)-2-ethyl-7-fluoro-4-oxo-3,4-dihydroquinazolin-6-yl) acrylate (4s)

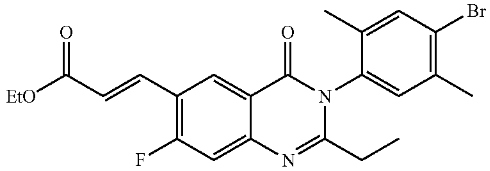 [SMILES: CCOC(=O)/C=C/c1cc2c(=O)n(-c3cc(C)c(Br)cc3C)c(CC)nc2cc1F]

The reaction mixture of 3s (4.0 g, 7.98 mmol), $Pd(OAc)_2$ (0.1 g, 0.40 mmol), $PPh_3$ (0.2 g, 0.80 mmol), NaOAc (1.0 g, 11.97 mmol), ethyl acrylate (0.9 mL, 8.78 mmol) in DMA (16 mL) was irritated by MW 250 W 20 min. After cooling to rt., the resulting solution was filtered and extracted with DCM (75 mL×2) and saturated NaCl (75 mL). The organic layer was dried over $MgSO_4$, filtered and concentrated in vacuo to give the crude as dark oil. The crude was purified by flash column (¢4×8, EA/HEX=1/10-1/9) to give the product as yellow oil. The oil was added Hex (50 mL) and sonicated under rt. for 2 min to precipitate the product as white solid. (1.4 g, 38%). The filtrate was concentrated and washed with MeOH (30 mL) to give the product as yellow solid. (0.4 g, 9%). Total (1.8 g, 47%). Rf=0.55 (EA/Hex=1:2); ESIMS(+) m/z 474 $[M+H]^+$ (E)-ethyl 3-(3-(4-bromo-3-methylphenyl)-2-ethyl-7-fluoro-4-oxo-3,4-dihydroquinazolin-6-yl)acrylate (4t)

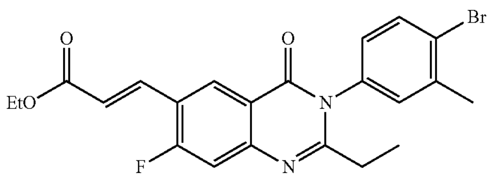 [SMILES: CCOC(=O)/C=C/c1cc2c(=O)n(-c3ccc(Br)c(C)c3)c(CC)nc2cc1F]

The reaction mixture of 3t (4.5 g, 9.24 mmol), $Pd(OAc)_2$ (0.1 g, 0.46 mmol), $PPh_3$ (0.2 g, 0.92 mmol), NaOAc (1.1 g, 13.86 mmol), ethyl acrylate (1 mL, 9.24 mmol) in DMA (19 mL) was irritated by MW 250 W 30 min. After cooling to rt., the resulting solution was filtered and the filtrate was extracted with DCM (75 mL×2) and saturated NaCl (75 mL). The organic layer was dried over $MgSO_4$, filtered and concentrated in vacuo to give the crude as dark oil. The crude was purified by flash column (¢4.5×10, EA/HEX=1/9-1/7) to give the product as yellow solid. The solid was washed with Hex (50 mL) to give the product as yellow solid. (1.8 g, 42%). Rf=0.45 (EA/Hex=1:2);

(E)-ethyl 3-(3-(2,3-dimethylphenyl)-2-ethyl-7-fluoro-4-oxo-3,4-dihydroquinazolin-6-yl)acrylate (4u)

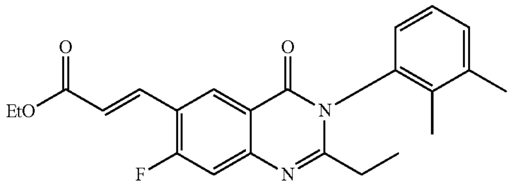 [SMILES: CCOC(=O)/C=C/c1cc2c(=O)n(-c3cccc(C)c3C)c(CC)nc2cc1F]

The reaction mixture of 3u (4.0 g, 9.47 mmol), $Pd(OAc)_2$ (0.1 g, 0.47 mmol), $PPh_3$ (0.3 g, 0.95 mmol), NaOAc (1.2 g, 14.21 mmol), ethyl acrylate (1 mL, 9.47 mmol) in DMA (19 mL) was irritated by MW 250 W 30 min. After cooling to rt., the resulting solution was filtered and the filtrate was extracted with DCM (75 mL×2) and saturated NaCl (75 mL). The organic layer was dried over $MgSO_4$, filtered and concentrated in vacuo to give the crude as dark oil. The crude was purified by flash column (¢4.5×8.5, EA/HEX=1/9-1/7) to give the product as orange oil. The oil was precipitated by Hex (20 mL), ether (5 mL) and sonicated under 0° C. to give the product as beige solid. (1.7 g, 46%). Rf=0.5 (EA/Hex=1:2);

(E)-ethyl 3-(3-(2,5-dimethylphenyl)-2-ethyl-7-fluoro-4-oxo-3,4-dihydroquinazolin-6-yl)acrylate (4w)

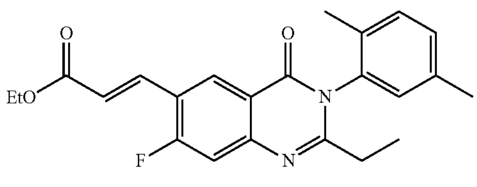 [SMILES: CCOC(=O)/C=C/c1cc2c(=O)n(-c3cc(C)ccc3C)c(CC)nc2cc1F]

The reaction mixture of 3w (3.2 g, 7.53 mmol), $Pd(OAc)_2$ (0.1 g, 0.38 mmol), $PPh_3$ (0.2 g, 0.75 mmol), NaOAc (0.9 g, 11.30 mmol), ethyl acrylate (0.9 mL, 8.28 mmol) in DMA (15 mL) was irritated by MW 250 W 25 min. After cooling to rt., the resulting solution was filtered and extracted with DCM (75 mL×2) and saturated NaCl (75 mL). The organic layer was dried over $MgSO_4$, filtered and concentrated in vacuo to give the crude as black slurry oil. The crude was washed with MeOH (15 mL) to give the product as brown-yellow solid. (1.4 g, 47%). Rf=0.5 (EA/Hex=1:2);

(E)-ethyl 3-(3-(2,4-dimethylphenyl)-2-ethyl-7-fluoro-4-oxo-3,4-dihydroquinazolin-6-yl)acrylate (4y)

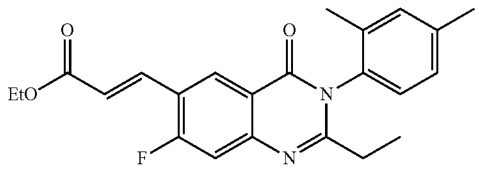 [SMILES: CCOC(=O)/C=C/c1cc2c(=O)n(-c3ccc(C)cc3C)c(CC)nc2cc1F]

The reaction mixture of 3y (3.5 g, 8.29 mmol), $Pd(OAc)_2$ (0.1 g, 0.41 mmol), $PPh_3$ (0.2 g, 0.83 mmol), NaOAc (1.0 g, 12.44 mmol), ethyl acrylate (1.0 mL, 9.12 mmol) in DMA (16 mL) was irritated by MW 250 W 25 min. After cooling to rt., the resulting solution was filtered and extracted with DCM (75 mL×2) and saturated NaCl (75 mL). The organic layer was dried over $MgSO_4$, filtered and concentrated in vacuo to give the crude as brown slurry oil. The crude was washed with MeOH (30 mL) to give the product as brown solid. The filtrate was concentrated and the residue was washed with MeOH (20 mL) to give the products orange-yellow solid. (0.8 g, 24%). Total (2.1 g, 65%). Rf=0.65 (EA/Hex=1:2);

(E)-ethyl 3-(3-(2-bromo-4-chlorophenyl)-2-ethyl-7-fluoro-4-oxo-3,4-dihydroquinazolin-6-yl)acrylate (4z)

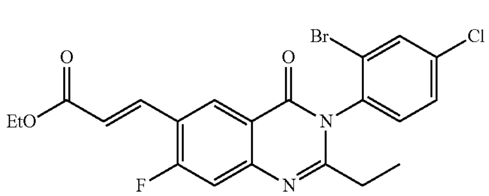 [SMILES: CCOC(=O)/C=C/c1cc2c(=O)n(-c3ccc(Cl)cc3Br)c(CC)nc2cc1F]

The reaction mixture of 3z (3.6 g, 7.09 mmol), $Pd(OAc)_2$ (79 mg, 0.35 mmol), $PPh_3$ (0.2 g, 0.71 mmol), NaOAc (0.9 g, 10.64 mmol), ethyl acrylate (0.8 mL, 7.80 mmol) in DMA (10 mL) was irritated by MW 250 W 25 min. After cooling to rt., the resulting solution was filtered and extracted with DCM (75 mL×2) and saturated NaCl (75 mL). The organic layer was dried over $MgSO_4$, filtered and concentrated in vacuo to give the crude as brown oil. The crude was purified by flash column (¢4.5×8, EA/HEX=1/10-1/8) to give the product as brown solid. (1.3 g, 37%). Rf=0.68 (EA/Hex=1:2);

(E)-ethyl 3-(2-ethyl-7-fluoro-3-(4-fluoro-2-methylphenyl)-4-oxo-3,4-dihydroquinazolin-6-yl)acrylate (4aa)

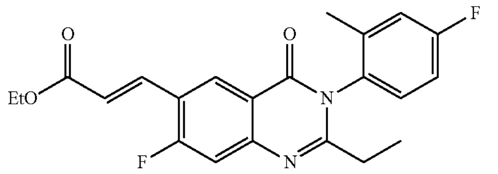 [SMILES: CCOC(=O)/C=C/c1cc2c(=O)n(-c3ccc(F)cc3C)c(CC)nc2cc1F]

The reaction mixture of 3aa (3.5 g, 8.21 mmol), $Pd(OAc)_2$ (0.1 g, 0.41 mmol), $PPh_3$ (0.2 g, 0.82 mmol), NaOAc (1.0 g, 12.32 mmol), ethyl acrylate (1.0 mL, 9.03 mmol) in DMA (16 mL) was irritated by MW 250 W 25 min. After cooling to rt., the resulting solution was filtered and extracted with DCM (75 mL×2) and saturated NaCl (75 mL). The organic layer was dried over $MgSO_4$, filtered and concentrated in vacuo to give the crude as brown oil. The crude was purified by flash column (¢3.5×11, EA/HEX=1/10-1/6-DCM/Hex=1/5-1/3) to give the product as brown solid. (1.5 g, 47%). Rf=0.58 (EA/Hex=1:2);

(E)-ethyl 3-(3-(4-bromo-2-fluorophenyl)-2-ethyl-7-fluoro-4-oxo-3,4-dihydroquinazolin-6-yl)acrylate (4ab)

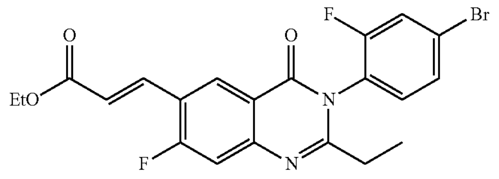

The reaction mixture of 3ab (4.5 g, 9.25 mmol), $Pd(OAc)_2$ (0.1 g, 0.46 mmol), $PPh_3$ (0.2 g, 0.92 mmol), NaOAc (1.1 g, 13.87 mmol), ethyl acrylate (1.1 mL, 10.17 mmol) in DMA (19 mL) was irritated by MW 250 W 25 min. After cooling to rt., the resulting solution was filtered and extracted with DCM (100 mL×2) and saturated NaCl (100 mL), H2O (10 mL). The organic layer was dried over $MgSO_4$, filtered and concentrated in vacuo to give the crude as dark oil. The crude was purified by flash column (¢4.5×10, EA/HEX=1/10-1/8) to give the product as green solid. (1.6 g, 38%). Rf=0.48 (EA/Hex=1:2); ESIMS(+) m/z 464 $[M+H]^+$ (E)-ethyl 3-(2-ethyl-7-fluoro-3-mesityl-4-oxo-3,4-dihydroquinazolin-6-yl)acrylate (4ad)

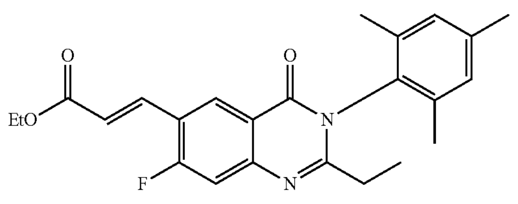 [SMILES: CCOC(=O)/C=C/c1cc2c(=O)n(-c3c(C)cc(C)cc3C)c(CC)nc2cc1F]

The reaction mixture of 3ad (5.4 g, 12.45 mmol), $Pd(OAc)_2$ (0.1 g, 0.62 mmol), $PPh_3$ (0.3 g, 1.25 mmol), NaOAc (1.5 g, 18.68 mmol), ethyl acrylate (1.5 mL, 13.70 mmol) in DMA (24 mL) was irritated by MW 250 W 25 min. After cooling to rt., the resulting solution was diluted with DCM (30 mL) and filtered. The filtrate was extracted with DCM (75 mL×2) and saturated NaCl (sat. 75 mL). The organic layer was dried over $MgSO_4$, filtered and concentrated in vacuo to give the crude as black solid. The crude was dissolved with DCM (7.5 mL) and purified by flash column (¢4.5×10, EA/HEX=1/10-1/8) to give orange solid. The solid was washed with Hex (30 mL) to give the product as orange solid. (2.3 g, 46%). Rf=0.5 (EA/Hex=1:2);

(E)-ethyl 3-(3-(4-bromo-2,6-dimethylphenyl)-2-ethyl-7-fluoro-4-oxo-3,4-dihydroquinazolin-6-yl) acrylate (4ae)

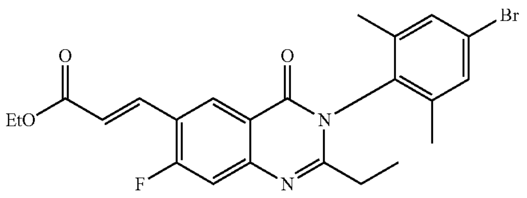 [SMILES: CCOC(=O)/C=C/c1cc2c(=O)n(-c3c(C)cc(Br)cc3C)c(CC)nc2cc1F]

The reaction mixture of 3ae (1.5 g, 3.03 mmol), $Pd(OAc)_2$ (34 mg, 0.15 mmol), $PPh_3$ (79 mg, 0.30 mmol), NaOAc (0.4 g, 4.55 mmol), ethyl acrylate (0.4 mL, 3.34 mmol) in DMA (6 mL) was irritated by MW 250 W 25 min. After cooling to rt., the resulting solution was filtered and the filtrate was extracted with DCM (50 mL×2) and saturated NaCl (sat. 50 mL). The organic layer was dried over $MgSO_4$, filtered and concentrated in vacuo to give the crude as black solid. The crude was washed with MeOH (15 mL) (oil to slurry solution) and the solid was filtered to give the product as brown solid. (0.5 g, 35%). Rf=0.6 (EA/Hex=1:2);

(E)-ethyl 3-(2-ethyl-7-fluoro-4-oxo-3-phenyl-3,4-dihydroquinazolin-6-yl)acrylate (4ag)

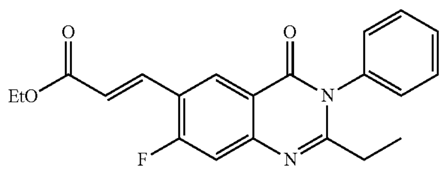 [SMILES: CCOC(=O)/C=C/c1cc2c(=O)n(-c3ccccc3)c(CC)nc2cc1F]

The reaction mixture of 3ag (4.1 g, 10.40 mmol), $Pd(OAc)_2$ (0.1 g, 0.52 mmol), $PPh_3$ (0.3 g, 1.04 mmol), NaOAc (1.3 g, 15.60 mmol), ethyl acrylate (1.2 mL, 11.44 mmol) in DMA (21 mL) was irritated by MW 250 W 30 min. After cooling to rt., the resulting solution was diluted with DCM and filtered. The filtrate was extracted with DCM (100 mL×2) and saturated NaCl (sat. 100 mL). The organic layer was dried over $MgSO_4$, filtered and concentrated in vacuo to give the crude as black oil. The crude was purified by flash column (¢4×11, EA/HEX=1/10-1/7.5) to give the product as clear orange solid. (2.5 g, 65%). Rf=0.38 (EA/Hex=1:2);

(E)-ethyl 3-(2-ethyl-7-fluoro-3-(4-methoxy-2-methylphenyl)-4-oxo-3,4-dihydroquinazolin-6-yl)acrylate (4ah)

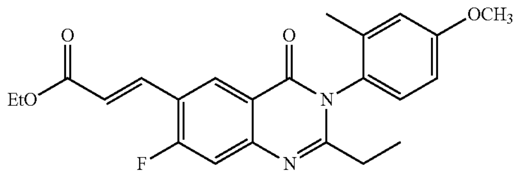 [SMILES: CCOC(=O)/C=C/c1cc2c(=O)n(-c3ccc(OC)cc3C)c(CC)nc2cc1F]

The reaction mixture of 3ah (2.6 g, 6.00 mmol), $Pd(OAc)_2$ (67 mg, 0.30 mmol), $PPh_3$ (0.2 g, 0.60 mmol), NaOAc (0.7 g, 9.00 mmol), ethyl acrylate (0.7 mL, 6.60 mmol) in DMA (12 mL) was irritated by MW 250 W 30 min. After cooling to rt., the resulting solution was diluted with DCM and filtered. The filtrate was extracted with DCM (50 mL×2) and saturated NaCl (sat. 50 mL). The organic layer was dried over $MgSO_4$, filtered and concentrated in vacuo to give the crude as black oil. The crude was purified by flash column (¢4×9, EA/HEX=1/10-1/6) to give the product as brown oil. The oil was added EA (2 mL), Hex (5 mL), ether (1.5 mL) and sonicated to precipitate the product as brown solid. (1.7 g, 69%). Rf=0.35 (EA/Hex=1:2);

(E)-ethyl 3-(2-ethyl-8-fluoro-3-(4-fluoro-2-methylphenyl)-4-oxo-3,4-dihydroquinazolin-6-yl)acrylate (4ai)

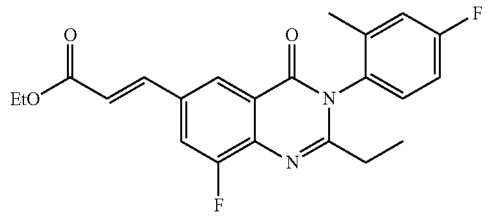 [SMILES: CCOC(=O)/C=C/c1cc(F)c2nc(CC)n(-c3ccc(F)cc3C)c(=O)c2c1]

The reaction mixture of 3ai (5.2 g, 12.57 mmol), $Pd(OAc)_2$ (0.1 g, 0.63 mmol), $PPh_3$ (0.3 g, 1.26 mmol), NaOAc (1.6 g, 18.85 mmol), ethyl acrylate (1.5 mL, 13.82 mmol) in DMA (24 mL) was irritated by MW 250 W 30 min. After cooling to rt., the resulting solution was diluted with DCM and filtered. The filtrate was extracted with DCM (100 mL×2) and saturated NaCl (sat. 100 mL). The organic layer was dried over $MgSO_4$, filtered and concentrated in vacuo to give the crude as black oil. The crude was purified by flash column (¢4.5×10, EA/HEX=1/10-1/8) to give the product as yellow solid. (3.0 g, 60%). Rf=0.43 (EA/Hex=1:2);

(E)-ethyl 3-(3-(2,6-dimethylphenyl)-2-ethyl-4-oxo-3,4-dihydropyrido[2,3-d]pyrimidin-6-yl)acrylate (68)

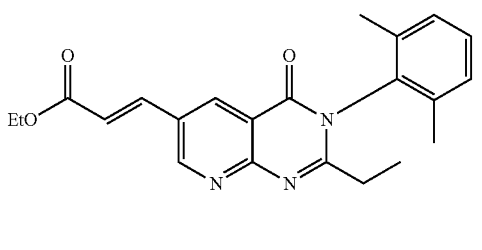 [SMILES: CCOC(=O)/C=C/c1cnc2nc(CC)n(-c3c(C)cccc3C)c(=O)c2c1]

The reaction mixture of 67 (3.5 g, 8.66 mmol), $Pd(OAc)_2$ (0.1 g, 0.43 mmol), $PPh_3$ (0.2 g, 0.87 mmol), NaOAc (1.1 g, 12.99 mmol), ethyl acrylate (1.0 mL, 9.52 mmol) in DMA (17 mL) was irritated by MW 250 W 30 min. After cooling to rt., the resulting solution was diluted with DCM and filtered. The filtrate was extracted with DCM (75 mL×2) and saturated NaCl (sat. 75 mL). The organic layer was dried over $MgSO_4$, filtered and concentrated in vacuo to give the crude as black oil. The crude was purified by flash column (¢4×9, EA/HEX=1/6-1/3) to give the product as clear orange solid. (1.7 g, 52%). Rf=0.43 (EA/Hex=1:1);

3-(3,5-dimethylphenyl)-7-fluoro-2-(1-fluoroethyl)-6-iodoquinazolin-4(3H)-one (4v)

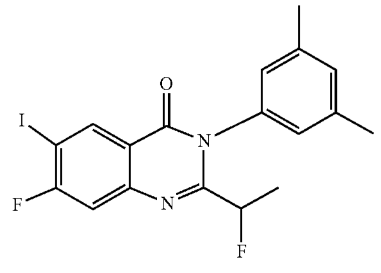 [SMILES: Cc1cc(C)cc(-n2c(C(C)F)nc3cc(F)c(I)cc3c2=O)c1]

The mixture solution of 3v (4.0 g, 9.47 mmol), selecfluro (5.0 g, 14.21 mmol) in DMF (40 mL) was heated at 90° C. for 6 h. The resulting solution was concentrated and added H2O (75 mL). The reaction solution was extracted with DCM (75 mL×2). The organic layer was dried over MgSO4 and concentrated to give the crude. The crude was purified by flash column (¢4.5×9, EA/DCM/Hex=13/130/400-7/70/200) to give the product as yellow solid. (1.71 g, 43%). Rf=0.55 (EA/Hex=1:20);

(E)-ethyl 3-(3-(2,6-diisopropylphenyl)-7-fluoro-2-methyl-4-oxo-3,4-dihydroquinazolin-6-yl)acrylate (4h)

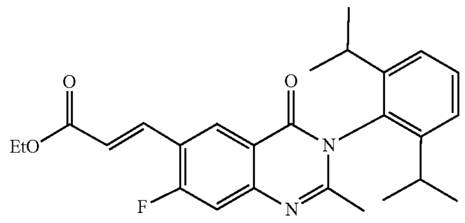 [SMILES: CCOC(=O)/C=C/c1cc2c(=O)n(-c3c(C(C)C)cccc3C(C)C)c(C)nc2cc1F]

The reaction mixture of 3h (2.3 g, 4.96 mmol), $Pd(OAc)_2$ (0.06 g, 0.25 mmol), $PPh_3$ (0.1 g, 0.50 mmol), NaOAc (0.6 g, 7.43 mmol), ethyl acrylate (1 mL, 7.43 mmol) in DMA (8.5 mL) was irritated by MW 250 W 25 min. After cooling to rt., the resulting solution was diluted with DCM and filtered. The filtrate was extracted with DCM (100 mL), EtOAc (100 mL) and saturated NaCl (75 mL). The organic layer was dried over $MgSO_4$, filtered and concentrated in vacuo to give the crude as dark oil. The crude was added MeOH (40 mL) to precipitate out the brown solid and the solid was further washed with H2O to give the product as brown solid. (1.5 g, 69%). The filtrate was concentrated and precipitated again to give the product as brown-red solid. (0.2 g, 11%). Total (1.7 g, 80%); Rf=0.43 (EA/Hex=1:2);

(E)-ethyl 3-(3-(2,6-dichlorophenyl)-7-fluoro-2-methyl-4-oxo-3,4-dihydroquinazolin-6-yl)acrylate (4i)

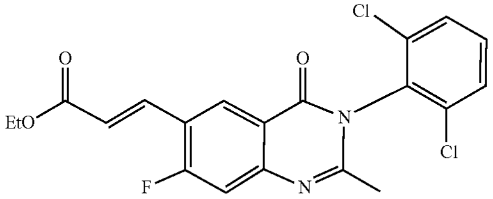 [SMILES: CCOC(=O)/C=C/c1cc2c(=O)n(-c3c(Cl)cccc3Cl)c(C)nc2cc1F]

The reaction mixture of 3i (5.0 g, 11.16 mmol), $Pd(OAc)_2$ (0.13 g, 0.56 mmol), $PPh_3$ (0.3 g, 1.12 mmol), NaOAc (1.4 g, 16.74 mmol), ethyl acrylate (2 mL, 16.74 mmol) in DMA (22 mL) was irritated by MW 250 W 25 min. After cooling to rt., the resulting solution was diluted with DCM and filtered. The filtrate was extracted with DCM (100 mL×2) and saturated NaCl (sat. 100 mL). The organic layer was dried over $MgSO_4$, filtered and concentrated in vacuo to give the crude. The crude was added MeOH (40 mL) to precipitate out the product as brown solid. (3.0 g, 63%); Rf=0.3 (EA/Hex=1:2);

(E)-ethyl 3-(3-(2,6-dimethylphenyl)-7-fluoro-2-methyl-4-oxo-3,4-dihydroquinazolin-6-yl)acrylate (4j)

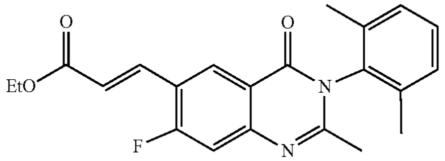 [SMILES: CCOC(=O)/C=C/c1cc2c(=O)n(-c3c(C)cccc3C)c(C)nc2cc1F]

The reaction mixture of 3j (4.7 g, 11.52 mmol), $Pd(OAc)_2$ (0.13 g, 0.58 mmol), $PPh_3$ (0.3 g, 1.15 mmol), NaOAc (1.4 g, 17.28 mmol), ethyl acrylate (1.4 mL, 12.67 mmol) in DMA (23 mL) was irritated by MW 250 W 25 min. After cooling to rt., the resulting solution was diluted with DCM and filtered. The filtrate was extracted with DCM (75 mL×2), H2O (10 mL) and saturated NaCl (sat. 75 mL). The organic layer was dried over $MgSO_4$, filtered and concentrated in vacuo to give the crude as black oil. The crude was added MeOH (40 mL) and EA (5 mL) to precipitate the solid as brown solid. (1.7 g, 39%) The filtrate was further purified by flash column (¢4.5×8, EA/HEX=1/8-1/6) to give the product as yellow solid. (2.0 g, 46%). total (3.7 g, 84%); Rf=0.5 (EA/Hex=1:2); ESIMS(+) m/z 403 $[M+Na]^+$ (E)-ethyl 3-(3-(2,6-dimethylphenyl)-5-fluoro-2-methyl-4-oxo-3,4-dihydroquinazolin-6-yl)acrylate (4k)

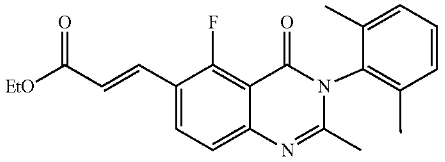 [SMILES: CCOC(=O)/C=C/c1ccc2nc(C)n(-c3c(C)cccc3C)c(=O)c2c1F]

The reaction mixture of 3k (2.5 g, 6.13 mmol), $Pd(OAc)_2$ (0.07 g, 0.31 mmol), $PPh_3$ (0.2 g, 0.61 mmol), NaOAc (0.8 g, 9.20 mmol), ethyl acrylate (1 mL, 9.20 mmol) in DMA (30 mL) was irritated by MW 250 W 25 min. After cooling to rt., the resulting solution was diluted with DCM and filtered. The filtrate was concentrated and extracted with EtOAc (75 mL×2), H2O (50 mL), saturated NaCl (50 mL). The organic layer was dried over $MgSO_4$, filtered and concentrated in vacuo to give the crude as dark oil. The crude was purified by flash column (¢4.5×8, EA/HEX=1/7-1/4) to give the product as yellow foam (1.2 g, 53%); Rf=0.23 (EA/Hex=1:2); ESIMS(+) m/z 403 $[M+Na]^+$ (E)-ethyl 3-(3-(2,6-dimethylphenyl)-8-fluoro-2-methyl-4-oxo-3,4-dihydroquinazolin-6-yl)acrylate (4l)

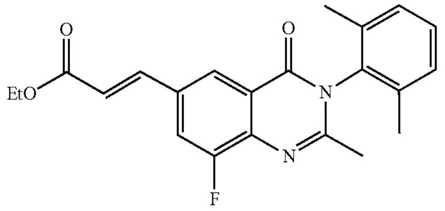 [SMILES: CCOC(=O)/C=C/c1cc(F)c2nc(C)n(-c3c(C)cccc3C)c(=O)c2c1]

The reaction mixture of 3l (4.2 g, 10.29 mmol), $Pd(OAc)_2$ (0.11 g, 0.51 mmol), $PPh_3$ (0.3 g, 1.03 mmol), NaOAc (1.3 g, 15.44 mmol), ethyl acrylate (1.2 mL, 11.32 mmol) in DMA (21 mL) was irritated by MW 250 W 25 min. After cooling to rt., the resulting solution was diluted with DCM (50 mL) and filtered. The filtrate was extracted with DCM (75 mL×2), H2O (20 mL) and saturated NaCl (sat. 75 mL). The organic layer was dried over $MgSO_4$, filtered and concentrated in vacuo to give the crude as black oil. The crude was purified by flash column (¢4.5×8, EA/HEX=1/7-1/5) to give the product as yellow foam. (3.6 g, 83%). Rf=0.3 (EA/Hex=1:2);

(E)-ethyl 3-(3-(2,6-difluorophenyl)-7-fluoro-2-methyl-4-oxo-3,4-dihydroquinazolin-6-yl)acrylate (4n)

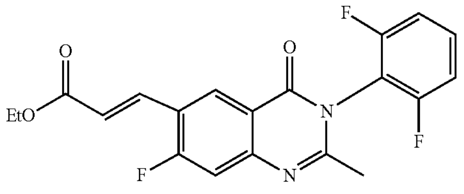 [SMILES: CCOC(=O)/C=C/c1cc2c(=O)n(-c3c(F)cccc3F)c(C)nc2cc1F]

The reaction mixture of 3n (5 g, 12.02 mmol), $Pd(OAc)_2$ (0.13 g, 0.60 mmol), $PPh_3$ (0.3 g, 1.20 mmol), NaOAc (1.5 g, 18.03 mmol), ethyl acrylate (1.4 mL, 13.22 mmol) in DMA (24 mL) was irritated by MW 250 W 25 min. After cooling to rt., the resulting solution was diluted with DCM (30 mL) and filtered. The filtrate was extracted with DCM (75 mL×2), H2O (10 mL) and saturated NaCl (sat. 100 mL). The organic layer was dried over $MgSO_4$, filtered and concentrated in vacuo to give the crude as black solid. The crude was dissolved with DCM (7.5 mL) and purified by flash column (¢4.5×8, DCM/Hex=1/2-EA/HEX=1/7-1/2) to give the product as white solid. (2.7 g, 59%). Rf=0.3 (EA/Hex=1:2);

(E)-3-(3-(2,6-difluorophenyl)-2-ethyl-7-fluoro-4-oxo-3,4-dihydroquinazolin-6-yl)acrylic acid (4o)

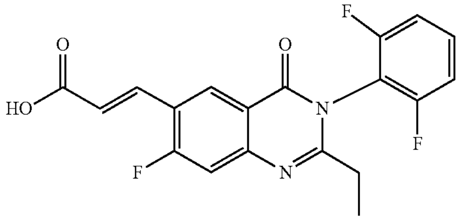 [SMILES: CCc1nc2cc(F)c(/C=C/C(=O)O)cc2c(=O)n1-c1c(F)cccc1F]

The mixture solution of 3o (3.1 g, 7.09 mmol), $Pd(OAc)_2$ (0.1 g, 0.57 mmol), $[(t\text{-}Bu)_3PH]BF_4$ (0.2 g, 0.57 mmol), acrylic acid (1 mL, 14.18 mmol), $Cs_2CO_3$ (3.5 g, 10.64 mmol) in DMF (25 mL) was irritated by MW 250 W 25 min. After cooling to rt., the resulting solution was filtered and the filtrate was extracted with EA (75 mL), $NaHCO_3$ (sat.) (75 mL×3). The water layer was acidified by 3 N HCl (57 mL) in ice-bath until pH=2 (some solid was precipitated). The resulting solution was filtered and the filtered solid was dried in vacuo to give the product as pink solid. (2.3 g, 86%). Rf=0.2 (MeOH/DCM=1/10);

(E)-ethyl 3-(3-(3,5-dimethylphenyl)-7-fluoro-2-methyl-4-oxo-3,4-dihydroquinazolin-6-yl)acrylate (4p)

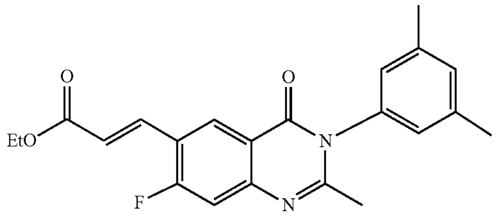 [SMILES: CCOC(=O)/C=C/c1cc2c(=O)n(-c3cc(C)cc(C)c3)c(C)nc2cc1F]

The reaction mixture of 3p (4.1 g, 10.04 mmol), $Pd(OAc)_2$ (0.1 g, 0.50 mmol), $PPh_3$ (0.3 g, 1.04 mmol), NaOAc (1.2 g, 15.07 mmol), ethyl acrylate (1.2 mL, 11.05 mmol) in DMA (20 mL) was irritated by MW 250 W 25 min. After cooling to rt., the resulting solution was diluted with DCM and filtered. The filtrate was extracted with DCM (75 mL×2) and saturated NaCl (sat. 75 mL). The organic layer was dried over $MgSO_4$, filtered and concentrated in vacuo to give the crude as black solid. The solid was washed with MeOH (50 mL) to sieve the product as deep-red solid. (2.3 g, 60%); Rf=0.25 (EA/Hex=1:2);

(E)-ethyl 3-(7-chloro-3-(2,6-dimethylphenyl)-2-methyl-4-oxo-3,4-dihydroquinazolin-6-yl)acrylate (4q)

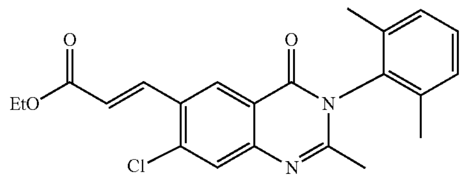 [SMILES: CCOC(=O)/C=C/c1cc2c(=O)n(-c3c(C)cccc3C)c(C)nc2cc1Cl]

The reaction mixture of 3q (5.7 g, 13.47 mmol), $Pd(OAc)_2$ (0.2 g, 0.67 mmol), $PPh_3$ (0.4 g, 1.35 mmol), NaOAc (1.7 g, 20.21 mmol), ethyl acrylate (1.6 mL, 14.82 mmol) in DMA (25 mL) was irritated by MW 250 W 25 min. After cooling to rt., the resulting solution was diluted with DCM and filtered. The filtrate was extracted with DCM (100 mL×2) and saturated NaCl (sat. 100 mL). The organic layer was dried over $MgSO_4$, filtered and concentrated in vacuo to give the crude as dark oil. The crude was purified by flash column (¢4.5×8, DCM/Hex=2/3–EA/Hex=1/4) to give the orange oil. The oil was added Hex (40 mL) and sonicated at rt. for 1 min to precipitated the product as white solid. (0.8 g, 15% for two steps); Rf=0.48 (EA/Hex=1:2);

(E)-ethyl 3-(7-chloro-3-(2,6-dimethylphenyl)-2-ethyl-4-oxo-3,4-dihydroquinazolin-6-yl)acrylate (4r)

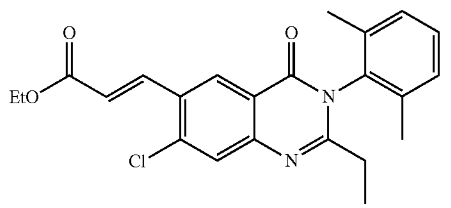 [SMILES: CCOC(=O)/C=C/c1cc2c(=O)n(-c3c(C)cccc3C)c(CC)nc2cc1Cl]

The reaction mixture of 3r (3.0 g, 7.47 mmol), $Pd(OAc)_2$ (0.1 g, 0.37 mmol), $PPh_3$ (0.2 g, 0.75 mmol), NaOAc (1.0 g, 11.21 mmol), ethyl acrylate (1 mL, 8.22 mmol) in DMA (15 mL) was irritated by MW 250 W 25 min. After cooling to rt., the resulting solution was diluted with DCM and filtered. The filtrate was extracted with DCM (75 mL×2) and saturated NaCl (sat. 75 mL). The organic layer was dried over $MgSO_4$, filtered and concentrated in vacuo to give the crude as dark oil. The crude was purified by flash column (¢4.5×8, EA/Hex=1/7) to give orange solid. The solid was further washed with ether (30 mL) to give the product as orange solid. (1.7 g, 55%); Rf=0.48 (EA/Hex=1:2);

Example 14: (E)-3-(2-ethyl-7-fluoro-3-(2-methyl-3-(trifluoromethyl)phenyl)-4-oxo-3,4-dihydroquinazolin-6-yl)-N-hydroxyacrylamide (5c, Compound 4)

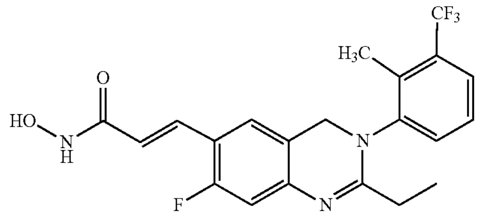 [SMILES: CCC1=Nc2cc(F)c(/C=C/C(=O)NO)cc2CN1c1cccc(C(F)(F)F)c1C]

The slurry solution of NaOH (0.3 g, 7.14 mmol) in $NH_2OH$ (2 M in MeOH, 27 mL) was added 4c (1.7 g, 3.57 mmol) at 0° C. and stirred for 0.5 h. The reaction solution was stirred at rt. for another 1.5 h then stirred at 30° C. for 1 h. The resulting solution was quenched with 2 N HCl until pH=2 and stirred at rt. for 10 min. The slurry solution was extracted with DCM (75 mL×2) and H2O (75 mL). The slurry organic layer was separated and concentrated. The residue purified by flash column (¢3.5×8, MeOH/DCM=1/80-1/50) to give the mixture fraction. The mixture was further purified by washed with MeOH/EA=1/5 mL to give the product as yellowish solid. (0.2 g, 10%). Rf=0.4 (MeOH/DCM=1:10); $^1$H NMR (400 MHz, DMSO-d6): δ 1.13 (t, 3H, J=7.5 Hz), 2.12 (s, 3H), 2.15-2.36 (m, 2H), 6.70 (d, 1H, J=16.0 Hz), 7.58-7.65 (m, 3H), 7.79 (d, 1H, J=7.7 Hz), 7.90 (d, 1H, J=7.8 Hz), 8.37 (d, 1H, J=8.2 Hz), 9.20 (br, 1H), 10.90 (s, 1H); ESIMS(+) m/z [M−H]$^-$; HPLC 97%.

Example 15: (E)-3-(3-(2,6-dimethylphenyl)-2-ethyl-7-fluoro-4-oxo-3,4-dihydroquinazolin-6-yl)-N-hydroxyacrylamide (5d, Compound 2)

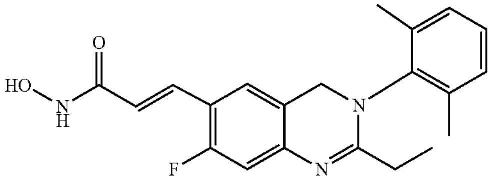 [SMILES: CCC1=Nc2cc(F)c(/C=C/C(=O)NO)cc2CN1c1c(C)cccc1C]

The slurry solution of NaOH (0.8 g, 20.28 mmol) in $NH_2OH$ (76 mL) was added 4d (4.0 g, 10.14 mmol) at rt. and stirred for 1.5 h. The resulting solution was quenched with 2 N HCl (25 mL) until pH=2 and extracted with CHCl3 (100 mL×2), H2O (100 mL). The organic layer was concentrated in vacuo to give the crude. The crude was purified by flash column (¢5.5×9, MeOH/CHCl3=1/40-1/20) to give the product as orange solid. The solid was dissolved with MeOH (5 mL), CHCl3 (5 mL), DCM (20 mL) and concentrated until the solvent remained 5 mL. The residue was added EA (3 mL) and sonicated to precipitate the product (clear to slurry). The slurry solution was added Hex (20 mL) during sonication to precipitate the product as beige solid (1.98 g, 51%). Rf=0.3 (MeOH/DCM=1:10); $^1$H NMR (400 MHz, DMSO-d6) δ 1.15 (t, 3H, J=7.26), 2.22 (q, 2H, J=7.27 Hz), 6.71 (d, 1H, J=16.0 Hz), 7.29-7.37 (m, 3H), 7.58 (s, 1H), 7.61 (s, 1H), 8.39 (d, 1H, J=8.2 Hz), 9.20 (br, 1H), 10.91 (s, 1H); ESIMS(+) m/z 380 [M−H]$^-$; HPLC 96%.

Example 16: (E)-3-(3-(3,5-dimethylphenyl)-2-ethyl-7-fluoro-4-oxo-3,4-dihydroquinazolin-6-yl)-N-hydroxyacrylamide (5e, Compound 7)

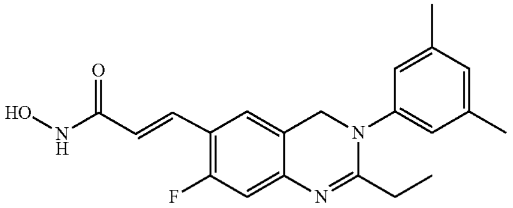 [SMILES: CCC1=Nc2cc(F)c(/C=C/C(=O)NO)cc2CN1c1cc(C)cc(C)c1]

The slurry solution of NaOH (0.5 g, 12.18 mmol) in $NH_2OH$ (45 mL) was added 4e (2.4 g, 6.08 mmol) at 0° C. and stirred for 1.5 h. The resulting solution was warmed to rt. and stirred for another 2.5 h. The reaction solution was extracted with DCM (100 mL), H2O (100 mL), DCM (100 mL+2N HCl 18 mL). The organic layer was dried over $MgSO_4$, filtered and concentrated in vacuo to give the crude as yellow oil. The crude was purified by flash column (¢4.5×6, MeOH/DCM=1/30-1/20) to give the product as orange solid. The solid was further washed with EA (25 mL) to give the product as clear orange solid. (0.7 g, 30%). Rf=0.08 (MeOH/DCM=1:10); $^1$H NMR (400 MHz, DMSO-d6) δ 1.11 (t, 3H, J=7.3 Hz), 2.33 (s, 6H), 2.36 (q, 2H, J=7.3 Hz), 6.70 (d, 1H, J=15.9 Hz), 7.03 (s, 2H), 7.15 (s, 1H), 7.53 (d, 1H, J=11.8 Hz), 7.58 (d, 1H, J=15.9 Hz), 8.32 (d, 1H, J=8.2 Hz), 9.20 (br, 1H), 10.89 (s, 1H); ESIMS(+) m/z 404 [M+Na]$^-$; HPLC 96%.

Example 17: (E)-3-(3-(4-bromo-2-methylphenyl)-2-ethyl-7-fluoro-4-oxo-3,4-dihydroquinazolin-6-yl)-N-hydroxyacrylamide (5f, Compound 6)

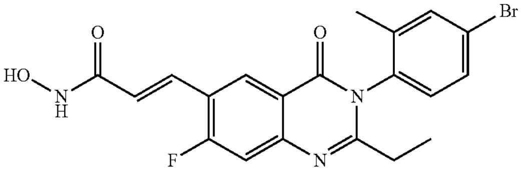 [SMILES: CCc1nc2cc(F)c(/C=C/C(=O)NO)cc2c(=O)n1-c1ccc(Br)cc1C]

The slurry solution of NaOH (0.3 g, 7.25 mmol) in $NH_2OH$ (27 mL) was added 4f (1.7 g, 3.62 mmol) at 0° C. and stirred for 10 min. The resulting solution was warmed to rt. and stirred for another 1.5 h. The reaction solution was extracted with DCM (100 mL), H2O (100 mL), DCM (100 mL+2N HCl 9 mL). The organic layer was dried over $MgSO_4$, filtered and concentrated in vacuo to give the crude as yellow oil. The crude was purified by flash column (¢3.5×8, MeOH/$CHCl_3$=1/30-1/25) to give the product as orange-red oil. The oil was precipitated by EA/ether (4/3 mL) to give the product as orange solid. (0.3 g, 16%). Rf=0.05 (EA/Hex=1:2); $^1$H NMR (400 MHz, DMSO-d6) δ 1.13 (t, 3H, J=7.3 Hz), 2.02 (s, 3H), 2.16-2.41 (m, 2H), 6.70 (d, 1H, J=15.9 Hz), 7.39 (d, 1H, J=8.4 Hz), 7.56-7.61 (m, 3H), 7.72 (d, 1H, J=1.9 Hz), 8.36 (d, 1H, J=8.2 Hz), 9.20 (br, 1H), 10.88 (s, 1H); ESIMS(+) m/z 444 [M−H]$^-$; HPLC 100%.

Example 18: (E)-3-(3-(2,6-diisopropylphenyl)-2-ethyl-7-fluoro-4-oxo-3,4-dihydroquinazolin-6-yl)-N-hydroxyacrylamide (5g, Compound 8)

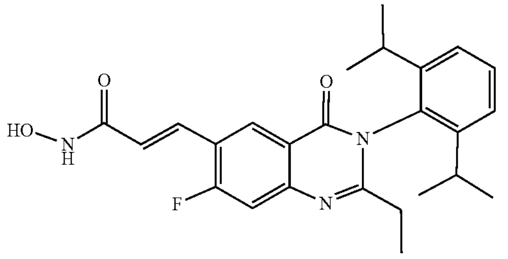 [SMILES: CCc1nc2cc(F)c(/C=C/C(=O)NO)cc2c(=O)n1-c1c(C(C)C)cccc1C(C)C]

The slurry solution of NaOH (0.5 g, 11.24 mmol) in $NH_2OH$ (42 mL) was added 4g (2.5 g, 5.62 mmol) and stirred at rt. for another 1.5 h. The reaction solution was added the solution of NaOH (0.1 g, 2.81 mmol) in $NH_2OH$ (10 mL) and stirred at rt. for 0.5 h. The resulting solution was extracted with DCM (100 mL), NaCl (sat. 100 mL), $CHCl_3$ (100 mL+2N HCl 12 mL). The organic layer was dried over $MgSO_4$, filtered and concentrated in vacuo to give the crude as yellow oil. The crude was purified by flash column (¢4.5×8, MeOH/$CHCl_3$=1/50) to give the mixture product and the mixture was purified again by flash column (¢3.5×7, EA/Hex=1/1-2/1) to give the product as white-yellowish foam. The foam was washed with ether/Hex (1.5/1 mL) to give the product as white solid. (0.2 g, 9%). Rf=0.3 (MeOH/$CHCl_3$=1:10); $^1$H NMR (400 MHz, DMSO-d6) δ 1.01 (s, 3H), 1.02 (s, 3H), 1.14 (s, 3H), 1.16 (s, 3H), 1.17 (t, 3H, J=7.2 Hz), 2.20 (q, 2H, J=7.2 Hz), 2.43 (p, 2H, J=6.8 Hz), 6.74 (d, 1H, J=16.0 Hz), 7.40 (s, 1H) 7.41 (s, 1H), 7.50-7.63 (m, 3H), 8.41 (d, 1H, J=8.2 Hz), 9.21 (br, 1H), 10.82 (s, 1H); ESIMS(+) m/z 438 [M+H]+; HPLC 90%

Example 19: (E)-3-(3-(2,6-dimethylphenyl)-2-ethyl-8-fluoro-4-oxo-3,4-dihydroquinazolin-6-yl)-N-hydroxyacrylamide (5m, Compound 11)

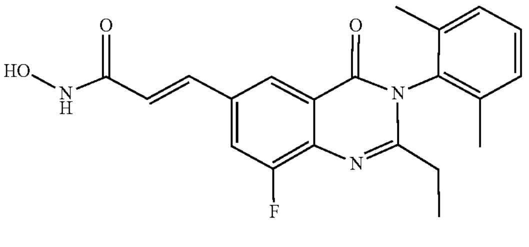 [SMILES: CCc1nc2c(F)cc(/C=C/C(=O)NO)cc2c(=O)n1-c1c(C)cccc1C]

The slurry solution of NaOH (0.6 g, 14.71 mmol) in $NH_2OH$ (55 mL) was added 4m (2.9 g, 7.36 mmol) at 0° C. for 0.5 h then stirred at rt for 1 h. The resulting solution was quenched with 2 N HCl (20 mL) and extracted with $CHCl_3$ (100 mL×2), H2O (100 mL) and NaCl (sat. 50 mL). The organic layer was concentrated in vacuo to give the crude as yellow oil. The crude was diluted with EA (20 mL) and sonicated at rt. for 2 mins to precipitate the product as beige solid. The solid was further washed with EA (20 mL) to give the product as beige solid (2.0 g, 70%). Rf=0.25 (MeOH/$CHCl_3$=1:10); $^1$H NMR (400 MHz, DMSO-d6) δ 1.16 (t, 3H, J=7.2 Hz), 2.10 (s, 6H), 2.24 (q, 2H, J=7.3 Hz), 6.62 (d, 1H, J=15.8 Hz), 7.29-7.38 (m, 3H), 7.57 (d, 1H, J=15.8 Hz), 8.00 (d, 1H, J=11.3 Hz), 8.12 (s, 1H), 9.15 (br, 1H), 10.82 (s, 1H); ESIMS(+) m/z 404 $[M+Na]^+$; HPLC 99%.

Example 20: (E)-3-(3-(4-bromo-2,5-dimethylphenyl)-2-ethyl-7-fluoro-4-oxo-3,4-dihydroquinazolin-6-yl)-N-hydroxyacrylamide (5s, Compound 20)

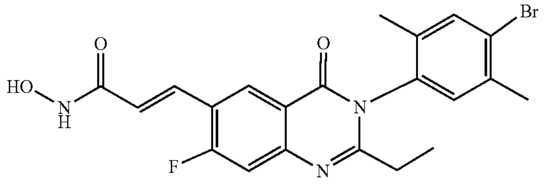 [SMILES: CCc1nc2cc(F)c(/C=C/C(=O)NO)cc2c(=O)n1-c1cc(C)c(Br)cc1C]

The slurry solution of NaOH (0.2 g, 6.00 mmol) in $NH_2OH$ (23 mL) was added 4s (1.4 g, 3.00 mmol) at 0° C. and stirred for 3 h. The resulting solution (slurry to clear) was quenched with 2 N HCl (5.5 mL) until pH=7 and extracted with DCM (60 mL×2), H2O (60 mL). The emulsificant solution was filtered and the filtrate was concentrated to give the crude as yellow oil. The crude was combined with filtered solid and dissolved with MeOH (30 mL), DCM (10 mL). The crude was purified by flash column (¢4×8, MeOH/DCM=1/50-1/30) to give the product as clear orange oil. The oil was diluted with DCM (1 mL), EA (3 mL) and precipitated by Hex (20 mL) dropwise under sonicator to precipitate the product as clear orange solid. (0.6 g, 45%). Rf=0.05 (MeOH/DCM=1:30); $^1$H NMR (400 MHz, DMSO-d6) δ 1.14 (t, 3H, J=7.2 Hz), 1.98 (s, 3H), 2.16-2.44 (m, 2H), 2.35 (s, 3H), 6.70 (d, 1H, J=16.0 Hz), 7.42 (s, 1H), 7.57 (s, 1H), 7.60 (d, 1H, J=5.5 Hz), 7.72 (s, 1H), 8.35 (d, 1H, J=8.2 Hz), 9.18 (s, 1H), 10.86 (s, 1H); ESIMS(+) m/z 460 [M+H]+; HPLC 96%.

Example 21: (E)-3-(3-(4-bromo-3-methylphenyl)-2-ethyl-7-fluoro-4-oxo-3,4-dihydroquinazolin-6-yl)-N-hydroxyacrylamide (5t, Compound 21)

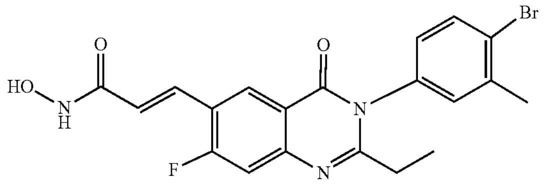 [SMILES: CCc1nc2cc(F)c(/C=C/C(=O)NO)cc2c(=O)n1-c1ccc(Br)c(C)c1]

The slurry solution of NaOH (0.3 g, 6.53 mmol) in $NH_2OH$ (25 mL) was added 4t (1.5 g, 3.27 mmol) at 0° C. and stirred at 30° C. for 5 h. The resulting solution was quenched with 2 N HCl (17 mL) until pH=7 and extracted with DCM (75 mL), H2O (75 mL). The emulsificant solution was filtered and the filtrate organic layer was collected. The water layer was further extracted with DCM (75 mL). To combine the organic layer which was concentrated to give the crude as yellow solid. The crude was purified by flash column (¢4×9, MeOH/DCM=1/60-1/30) to give the product as orange oil. The oil was diluted with MeOH (1 drop), DCM (2 mL), EA (2 mL) and precipitated by Hex (30 mL) dropwise under sonicator to precipitate the product as white solid. (0.2 g, 10%). Rf=0.23 (MeOH/DCM=1:10); $^1$H NMR (400 MHz, DMSO-d6) δ 1.19 (t, 3H, J=7.3 Hz), 2.35

(q, 2H, J=7.1 Hz), 2.39 (s, 3H), 6.68 (d, 1H, J=16.0 Hz), 7.25 (dd, 1H, J=8.4 Hz, 2.3 Hz), 7.47 (d, 1H, J=2.2 Hz), 7.54 (d, 1H, J=11.5 Hz), 7.58 (d, 1H, J=15.6 Hz), 7.78 (d, 1H, J=8.4 Hz), 8.34 (d, 1H, J=8.2 Hz), 9.21 (s, 1H), 10.90 (s, 1H); ESIMS(+) m/z 447 [M+H]+; HPLC 94%.

Example 22: (E)-3-(3-(2,3-dimethylphenyl)-2-ethyl-7-fluoro-4-oxo-3,4-dihydroquinazolin-6-yl)-N-hydroxyacrylamide (5u, Compound 22)

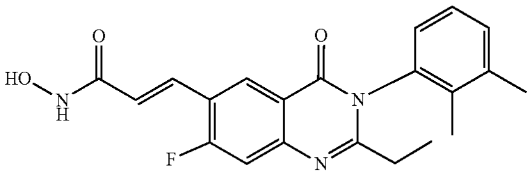 [SMILES: CCc1nc2cc(F)c(/C=C/C(=O)NO)cc2c(=O)n1-c1cccc(C)c1C]

The slurry solution of NaOH (0.3 g, 7.61 mmol) in $NH_2OH$ (29 mL) was added 4u (1.5 g, 3.80 mmol) at 0° C. and stirred at rt. for 1 h. The resulting solution was quenched with 2 N HCl (9.5 mL) until pH=7 and extracted with DCM (75 mL×2), H2O (30 mL) and NaCl (sat. 20 mL). The organic layer was dried over $MgSO_4$, filtered and concentrated in vacuo to give the crude as clear orange oil. The crude was purified by flash column (¢4×9, MeOH/DCM=1/50-1/35) to give the product as clear orange oil. The oil was diluted with MeOH (3 mL), DCM (5 mL) and precipitated by Hex (50 mL) dropwise under sonicator to give the product as white solid. (0.8 g, 57%). Rf=0.25 (MeOH/DCM=1:10); $^1$H NMR (400 MHz, DMSO-d6) δ 1.11 (t, 3H, J=14.6 Hz), 1.89 (s, 3H), 2.15-2.38 (m, 2H), 2.33 (s, 3H), 6.69 (d, 1H, J=16.0 Hz), 7.19-7.34 (m, 3H), 7.56 (d, 1H, J=7.6 Hz), 7.60 (d, 1H, J=11.8 Hz), 8.35 (d, 1H, J=8.2 Hz), 9.20 (s, 1H), 10.89 (s, 1H); ESIMS(+) m/z 382 $[M+H]^+$; HPLC 97%.

Example 23: (E)-3-(3-(2,5-dimethylphenyl)-2-ethyl-7-fluoro-4-oxo-3,4-dihydroquinazolin-6-yl)-N-hydroxyacrylamide (Compound 23, 5w)

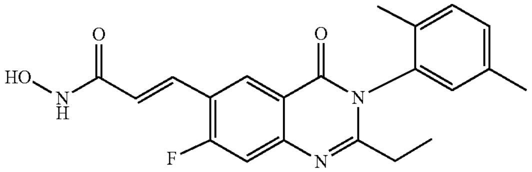 [SMILES: CCc1nc2cc(F)c(/C=C/C(=O)NO)cc2c(=O)n1-c1cc(C)ccc1C]

The slurry solution of NaOH (0.3 g, 7.10 mmol) in $NH_2OH$ (27 mL) was added 4w (1.4 g, 3.55 mmol) at 0° C. and stirred at 30° C. for 2 h. The resulting solution was quenched with 2 N HCl (14 mL) until pH=7 and extracted with DCM (75 mL×2), H2O (75 mL). The organic layer was dried over $MgSO_4$, filtered and concentrated in vacuo to give the crude as brown-orange oil. The crude was purified by flash column (¢4.5×8, MeOH/DCM=1/50-1/25) to give the product as orange oil. The oil was diluted with MeOH (1 mL) and added EA (3 mL) under sonicator for 2 mins to precipitate the product as clear orange solid. (0.3 g, 22%). Rf=0.1 (MeOH/DCM=1:20); $^1$H NMR (400 MHz, DMSO-d6) δ 1.12 (t, 3H, J=7.3 Hz), 1.95 (s, 3H), 2.14-2.41 (m, 2H), 2.32 (s, 3H), 6.69 (d, 1H, J=16.0 Hz), 7.18 (s, 1H), 7.24 (d, 1H, J=7.8 Hz), 7.33 (d, 1H, J=7.8 Hz), 7.55 (d, 1H, J=9.3 Hz), 7.58 (d, 1H, J=13.4 Hz), 8.35 (d, 1H, J=8.2 Hz), 9.21 (s, 1H), 10.91 (s, 1H); ESIMS(+) m/z 382 $[M+H]^+$; HPLC 97%.

Example 24: (E)-3-(3-(2,4-dimethylphenyl)-2-ethyl-7-fluoro-4-oxo-3,4-dihydroquinazolin-6-yl)-N-hydroxyacrylamide (Compound 27, 5y)

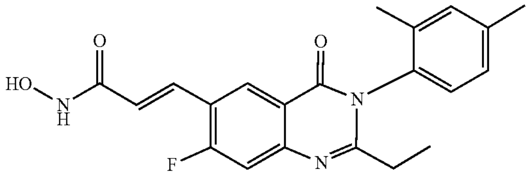 [SMILES: CCc1nc2cc(F)c(/C=C/C(=O)NO)cc2c(=O)n1-c1ccc(C)cc1C]

The slurry solution of NaOH (0.4 g, 10.65 mmol) in $NH_2OH$ (40 mL) was added 4y (2.1 g, 5.32 mmol) at 0° C. and stirred at rt. for 1.5 h. The resulting solution was quenched with 2 N HCl (15 mL) until pH=7 and extracted with DCM (70 mL×3), H2O (75 mL). The organic layer was dried over MgSO4 and concentrated to give the crude as brown-green oil. The crude was purified by flash column (¢4×11, MeOH/DCM=1/50-1/30) to give the product as orange oil. The oil was diluted with MeOH (1 mL), DCM (3 mL), ether (5 mL). The solution was concentrated until solid on the wall appeared. The slurry solution was sonicated and added Hex (5 mL) to precipitate the product as clear orange solid. (1.2 g, 57%). Rf=0.08 (MeOH/DCM=1:20); $^1$H NMR (400 MHz, DMSO-d6) δ 1.12 (t, 3H, J=7.3 Hz), 2.25-2.40 (m, 2H), 2.36 (s, 1H), 6.70 (d, 1H, J=15.9 Hz), 7.19 (d, 1H, J=8.0 Hz), 7.25 (d, 1H. J=8.3 Hz), 7.26 (s, 1H), 7.56 (d, 1H. J=6.4 Hz), 7.59 (d, 1H. J=10.5 Hz), 8.36 (d, 1H, J=8.2 Hz), 9.19 (s, 1H), 10.87 (s, 1H); ESIMS(+) m/z 382 $[M+H]^+$; HPLC 99%.

Example 25: (E)-3-(3-(2-bromo-4-chlorophenyl)-2-ethyl-7-fluoro-4-oxo-3,4-dihydroquinazolin-6-yl)-N-hydroxyacrylamide (Compound 29, 5z)

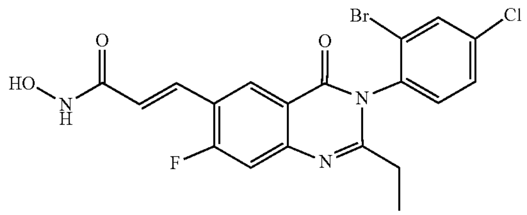 [SMILES: CCc1nc2cc(F)c(/C=C/C(=O)NO)cc2c(=O)n1-c1ccc(Cl)cc1Br]

The slurry solution of NaOH (0.3 g, 7.21 mmol) in $NH_2OH$ (27 mL) was added 4z (1.7 g, 3.61 mmol) at 0° C. and stirred at rt. for 1.5 h. The resulting orange-red solution was quenched with 2 N HCl (11 mL) until pH=7 (orange-red to yellow) and extracted with DCM (100 mL×2), H2O (100 mL). The organic layer was dried over MgSO4 and concentrated to give the crude as orange oil. The crude was purified by flash column (03.5×11, MeOH/DCM=1/50-1/33) to give the product as orange oil. The oil was diluted with EA (2 mL), DCM (1 mL) and sonicated until product precipitated. The precipitated solid was dissolved with MeOH (1 mL), DCM (3 mL) then concentrated. The residue was diluted with EA (3 mL), Hex (1 mL) and sonicated to precipitate the product as white solid. (0.1 g, 8%). Rf=0.3 (MeOH/DCM=1:10); $^1$H NMR (400 MHz, DMSO-d6) δ 1.12 (t, 3H, J=7.3 Hz), 2.25-2.40 (m, 2H), 2.36 (s, 1H), 6.70 (d, 1H, J=15.9 Hz), 7.19 (d, 1H, J=8.0 Hz), 7.25 (d, 1H. J=8.3 Hz), 7.26 (s, 1H), 7.56 (d, 1H. J=6.4 Hz), 7.59 (d, 1H. J=10.5 Hz), 8.36 (d, 1H, J=8.2 Hz), 9.19 (s, 1H), 10.87 (s, 1H); ESIMS(+) m/z 366 $[M+H]^+$; HPLC 96%.

Example 26: (E)-ethyl 3-(3-(4-chloro-2-methylphenyl)-2-ethyl-7-fluoro-4-oxo-3,4-dihydroquinazolin-6-yl)acrylate (5ac)

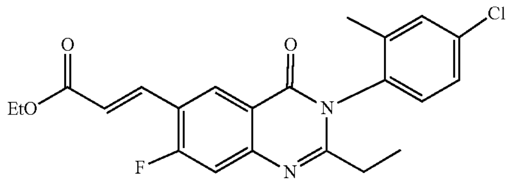 [SMILES: CCOC(=O)/C=C/c1cc2c(=O)n(-c3ccc(Cl)cc3C)c(CC)nc2cc1F]

The reaction mixture of 4z (0.9 g, 1.88 mmol), Pd2(dba)$_3$ (37 mg, 0.04 mmol), [(t-Bu)3PH]BF4 (43 mg, 0.15 mmol) in THF (4 mL) was added Me2Zn (3.5 mL, 1.2 M in toluene) was irritated by MW [Mode: standard, 200W, run time: 30 min, hold time: 55 min]. The resulting solution was filtered and the filtrate was extracted with DCM (70 mL×2), H2O (70 mL). The organic layer was dried over MgSO4 and concentrated to give the crude. The crude was purified by flash column (¢3.5×15, EA/HEX=1/10-1/8) to give the product as yellow solid. (0.5 g, 59%). Rf=0.43 (EA/Hex=1:5); ESIMS(+) m/z 415 $[M+H]^+$ Example 27: (E)-3-(3-(4-chloro-2-methylphenyl)-2-ethyl-7-fluoro-4-oxo-3,4-dihydroquinazolin-6-yl)-N-hydroxyacrylamide (Compound 25, 6ac)

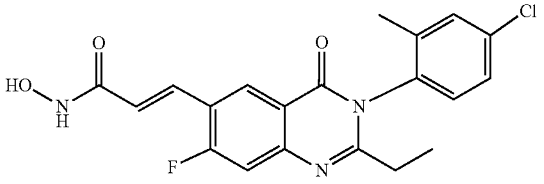 [SMILES: CCc1nc2cc(F)c(/C=C/C(=O)NO)cc2c(=O)n1-c1ccc(Cl)cc1C]

The slurry solution of NaOH (0.1 g, 2.36 mmol) in $NH_2OH$ (9 mL) was added 5ac (0.5 g, 1.18 mmol) at 0° C. and stirred at rt. for 7 h (stating material still remain). The resulting solution was quenched with 1 N HCl (10 mL) until pH=7 and extracted with DCM (40 mL×3), H2O (40 mL). The organic layer was dried over MgSO4 and concentrated to give the crude as yellow oil. The crude was purified by flash column (¢3.5×11, MeOH/DCM=1/50-1/30) to give the product as orange oil. The oil was diluted with MeOH (1 drop), DCM (3 mL), EA (3 mL), Hex (10 mL) to give the product as beige solid. The solid was dissolved with MeOH (0.5 mL), DCM (1 mL) and put at rt. overnight to give the product as white crystal (28 mg, COMPOUND 25-1). The filtrate was found some crystal after filtration (50 mg, COMPOUND 25-2). Total (78 mg, 16%). Rf=0.23 (MeOH/DCM=1:20); $^1$H NMR (400 MHz, DMSO-d6) δ 1.13 (t, 3H, J=7.3 Hz), 2.02 (s, 3H), 2.16-2.41 (m, 2H), 6.70 (d, 1H, J=16.0 Hz), 7.47 (s, 1H), 7.48 (s, 1H), 7.57-7.61 (m, 3H), 8.36 (d, 1H, J=8.2 Hz), 9.19 (s, 1H), 10.87 (s, 1H); ESIMS (+) m/z 402 [M+H]+; HPLC 95%.

Example 28: (E)-3-(2-ethyl-7-fluoro-3-(4-fluoro-2-methylphenyl)-4-oxo-3,4-dihydroquinazolin-6-yl)-N-hydroxyacrylamide (Compound 26, 5aa)

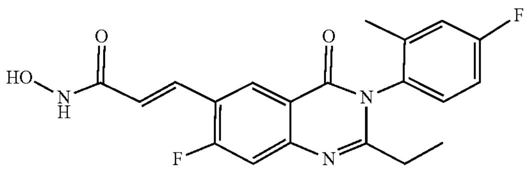 [SMILES: CCc1nc2cc(F)c(/C=C/C(=O)NO)cc2c(=O)n1-c1ccc(F)cc1C]

The slurry solution of NaOH (0.3 g, 7.53 mmol) in $NH_2OH$ (26 mL) was added 4aa (1.5 g, 3.77 mmol) at 0° C. and stirred at rt. for 2.5 h. The resulting yellow solution was quenched with 2 N HCl (14 mL) until pH=7 and extracted with DCM (80 mL×3), H2O (75 mL). The organic layer was dried over MgSO4 and concentrated to give the crude as orange oil. (The water layer had some white suspension solid.). The crude was purified by flash column (¢3.5×12, MeOH/DCM=1/30-1/25) to give the product as orange oil. The oil was diluted with DCM (1 mL), EA (2 mL) and precipitated by Hex (20 mL) to give the product as clear orange solid. (0.8 g, 53%). Rf=0.25 (MeOH/DCM=1:10); $^1$H NMR (400 MHz, DMSO-d6) δ 1.13 (t, 3H, J=7.3 Hz), 2.21-2.40 (m, 2H), 6.70 (d, 1H, J=16.0 Hz), 7.24 (td, 1H, J=8.5 Hz, 2.9 Hz), 7.35 (dd, 1H. J=9.6 Hz, 2.8 Hz), 7.48 (dd, 1H. J=8.7 Hz, 5.5 Hz), 7.57 (d, 1H. J=1.3 Hz), 7.60 (d, 1H. J=5.8 Hz), 8.36 (d, 1H, J=8.2 Hz), 9.19 (s, 1H), 10.88 (s, 1H); ESIMS(+) m/z 386 [M+H]+; HPLC 98%.

Example 29: (E)-3-(3-(4-bromo-2-fluorophenyl)-2-ethyl-7-fluoro-4-oxo-3,4-dihydroquinazolin-6-yl)-N-hydroxyacrylamide (Compound 28, 5ab)

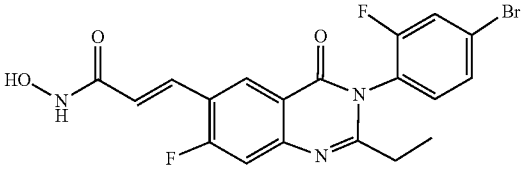 [SMILES: CCc1nc2cc(F)c(/C=C/C(=O)NO)cc2c(=O)n1-c1ccc(Br)cc1F]

The slurry solution of NaOH (0.3 g, 6.91 mmol) in $NH_2OH$ (26 mL) was added 4ab (1.6 g, 3.45 mmol) and stirred at 0° C. for 2.5 h. The resulting yellow slurry solution was quenched with 2 N HCl (12 mL) until pH=7 and extracted with DCM (75 mL×2), H2O (75 mL). The organic layer was dried over MgSO4 and c concentrated to give the crude as orange-yellow oil. (The water layer had some white suspension solid.). The crude was purified by flash column (¢3.5×8.5, MeOH/DCM=1/50-1/30) to give the product as beige solid. (46 mg, 9%). The starting material was recovered (recovery: 1.1 g, 69%). Rf=0.25 (MeOH/DCM=1:10); $^1$H NMR (400 MHz, DMSO-d6) δ 1.13 (t, 3H, J=7.3 Hz), 2.28-2.52 (m, 2H), 6.71 (d, 1H, J=16.0 Hz), 7.57-7.70 (m, 4H), 7.92 (d, 1H. J=9.0 Hz), 8.37 (d, 1H, J=8.1 Hz), 9.20 (s, 1H), 10.88 (s, 1H); ESIMS(+) m/z 451 $[M+H]^+$; HPLC 99%.

Example 30: (E)-3-(2-ethyl-7-fluoro-3-mesityl-4-oxo-3,4-dihydroquinazolin-6-yl)-N-hydroxyacrylamide (Compound 30, 5ad)

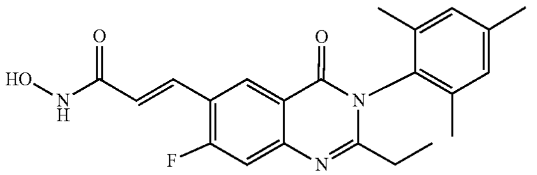 [SMILES: CCc1nc2cc(F)c(/C=C/C(=O)NO)cc2c(=O)n1-c1c(C)cc(C)cc1C]

The slurry solution of NaOH (0.5 g, 11.46 mmol) in $NH_2OH$ (43 mL) was added 4ad (2.3 g, 5.73 mmol) at 0° C. and stirred at rt. for 1 h. The resulting solution was quenched with 2 N HCl (21 mL) until pH=7 and extracted with DCM (75 mL×2), NaCl (sat. 75 mL). The organic layer was dried over MgSO4 and concentrated to give the crude as orange oil. The crude was purified by flash column (¢4×9, MeOH/DCM=1/60-1/30) to give the product as clear orange solid. The solid was dissolved with MeOH (2 mL), DCM (10 mL) and concentrated until the solvent remained 1 mL. The residue was added EA (3 mL), Hex (5 mL) and sonicated until the product precipitate. The slurry solution was added Hex (10 mL) to give the product as clear orange solid. (1.5 g, 66%). Rf=0.4 (MeOH/DCM=1:10); $^1$H NMR (400 MHz, DMSO-d6) δ 1.14 (t, 3H, J=7.3 Hz), 1.94 (s, 6H), 2.23 (q, 2H, 7.3 Hz), 6.71 (d, 1H, J=16.0 Hz), 7.10 (s, 2H), 7.57 (s, 1H), 7.61 (d, 1H, 2.9 Hz), 8.38 (d, 1H, J=8.2 Hz), 9.19 (s, 1H), 10.87 (s, 1H); ESIMS(+) m/z 394 $[M-H]^-$; HPLC 99%.

Example 31: (E)-3-(3-(4-bromo-2,6-dimethylphenyl)-2-ethyl-7-fluoro-4-oxo-3,4-dihydroquinazolin-6-yl)-N-hydroxyacrylamide (Compound 31, 5ae)

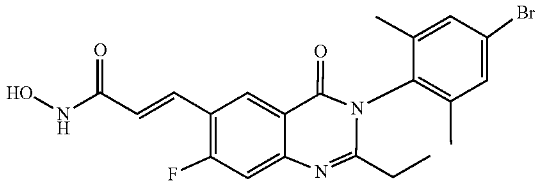 [SMILES: CCc1nc2cc(F)c(/C=C/C(=O)NO)cc2c(=O)n1-c1c(C)cc(Br)cc1C]

The slurry solution of NaOH (0.1 g, 2.96 mmol) in $NH_2OH$ (11 mL) was added 4ae (0.7 g, 1.48 mmol) at 0° C. and stirred at rt. for 2 h. The resulting solution was quenched with 1 N HCl until pH=7 and extracted with DCM (50 mL×2), NaCl (sat. 50 mL). The organic layer was dried over MgSO4 and concentrated to give the crude as orange oil. The crude was purified by flash column (¢3.5×9, MeOH/DCM=1/50-1/35) to give the product as orange oil. The oil was added MeOH (2 mL), DCM (10 mL) and concentrated until the solvent remained 1 mL. The residue was added EA (1.5 mL), Hex (5 mL) and sonicated for 5 min. The solution was put at rt. for 10 min to precipitate the product. The slurry solution was sonicated and added Hex (10 mL) to give the product as clear orange solid. (0.2 g, 35%). Rf=0.4 (MeOH/DCM=1:10); $^1$H NMR (400 MHz, DMSO-d6) δ 1.16 (t, 3H, J=7.2 Hz), 1.98 (s, 6H), 2.24 (q, 2H, 7.2 Hz), 6.71 (d, 1H, J=15.9 Hz), 7.56-7.62 (m, 4H), 8.39 (d, 1H, J=8.2 Hz), 9.19 (s, 1H), 10.87 (s, 1H); ESIMS(+) m/z 458 $[M-H]^-$; HPLC 96%.

Example 32: (E)-3-(2-ethyl-7-fluoro-4-oxo-3-phenyl-3,4-dihydroquinazolin-6-yl)-N-hydroxyacrylamide (5ag, Compound 33)

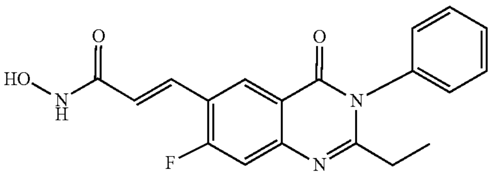 [SMILES: CCc1nc2cc(F)c(/C=C/C(=O)NO)cc2c(=O)n1-c1ccccc1]

The slurry solution of NaOH (0.3 g, 6.55 mmol) in $NH_2OH$ (25 mL) was added 4ah (1.2 g, 3.28 mmol) at 0° C. and stirred at the same condition for 40 mins. The reaction solution was warmed to rt and stirred for 1 h. The resulting solution was quenched with 1 N HCl (12 mL) until pH=7 and extracted with the solution of DCM (100 mL×2) mix MeOH (10 mL×2), NaCl (sat. 75 mL). The organic layer was dried over MgSO4 and concentrated to give the crude as orange oil. The crude was purified by flash column (¢4.5×8, MeOH/DCM=1/50-1/20) to give the product as clear orange oil. The oil was diluted with MeOH (1 mL), DCM (5 mL) and concentrated until the solvent remained 1 mL. The residue was added EA (3 mL) and sonicated to precipitate the product (clear to slurry). The slurry solution was added Hex (10 mL) and sonicated for 2 min to give the product as clear orange solid. (0.4 g, 35%). Rf=0.28 (MeOH/DCM=1:10); $^1$H NMR (400 MHz, DMSO-d6) δ 1.11 (t, 3H, J=7.3 Hz), 2.33 (q, 2H, J=7.3 Hz), 6.69 (d, 1H, J=15.9 Hz), 7.44 (s, 1H,), 7.46 (d, 1H, J=1.4 Hz), 7.53-7.61 (m, 5H), 8.34 (d, 1H, J=8.2 Hz), 9.19 (s, 1H), 10.88 (s, 1H); ESIMS(+) m/z 354 $[M+H]^+$; HPLC 99%.

Example 33: (E)-3-(2-ethyl-7-fluoro-3-(4-methoxy-2-methylphenyl)-4-oxo-3,4-dihydroquinazolin-6-yl)-N-hydroxyacrylamide (5ah, Compound 34)

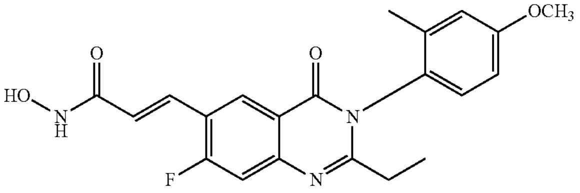 [SMILES: CCc1nc2cc(F)c(/C=C/C(=O)NO)cc2c(=O)n1Cc1ccc(OC)cc1C]

The slurry solution of NaOH (0.3 g, 8.28 mmol) in $NH_2OH$ (31 mL) was added 4ah (1.7 g, 4.14 mmol) at 0° C. and stirred at rt. for 1 h. The resulting solution was quenched with 2 N HCl (12 mL) until pH=7 and extracted with DCM (100 mL×2), NaCl (sat. 100 mL). The organic layer was dried over MgSO4 and concentrated to give the crude as orange oil. The crude was purified by flash column (¢4.5×9, MeOH/DCM=1/50-1/25) to give the product as orange oil. The oil was diluted with MeOH (1 mL), DCM (5 mL) and concentrated until the solvent remained 1 mL. The residue was added EA (3 mL) and sonicated at 0° C. to precipitate the product (clear to slurry). The slurry solution was added Hex (10 mL) and filtered to give the product as orange solid. (1.2 g, 70%). Rf=0.4 (MeOH/DCM=1:10); $^1$H NMR (400 MHz, DMSO-d6) δ 1.11 (t, 3H, J=7.3 Hz), 1.97 (s, 3H), 2.15-2.40 (m, 2H), 3.80 (s, 3H), 6.68 (d, 1H, J=15.9 Hz), 6.92 (dd, 1H, J=8.7 Hz, 2.8 Hz), 7.01 (d, 1H, J=2.8 Hz), 7.27 (d, 1H, J=8.6 Hz), 7.55 (d, 1H, J=11.8 Hz), 7.57 (d, 1H, J=15.8 Hz), 8.34 (d, 1H, J=8.2 Hz), 9.18 (s, 1H), 10.86 (s, 1H); ESIMS(+) m/z 398 [M+H]+; HPLC 97%.

Example 34: (E)-3-(2-ethyl-8-fluoro-3-(4-fluoro-2-methylphenyl)-4-oxo-3,4-dihydroquinazolin-6-yl)-N-hydroxyacrylamide (5ai, Compound 35)

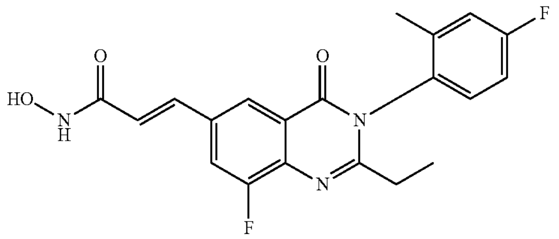 [SMILES: CCc1nc2c(F)cc(/C=C/C(=O)NO)cc2c(=O)n1Cc1ccc(F)cc1C]

The slurry solution of NaOH (0.6 g, 15.06 mmol) in $NH_2OH$ (56 mL) was added 4ai (3.0 g, 7.53 mmol) at 0° C. and stirred at rt. for 2.5 h. The resulting solution was quenched with 2 N HCl (24 mL) until pH=7 and extracted with DCM (100 mL), CHCl3 (200 mL), NaCl (sat. 100 mL). The organic layer was dried over MgSO4 and concentrated to give the crude as orange oil. The crude was purified by flash column (¢4.5×10, MeOH/DCM=1/40-1/20) to give the product as orange oil. The oil was diluted with EA (5 mL), DCM (3 mL), MeOH (1 mL) and sonicated for 2 mins. The resulting solution was put at rt. for 1 min (clear to slurry) and sonicated for 2 mins to precipitate the product as clear white solid. (1.5 g, 51%). Rf=0.25 (MeOH/DCM=1:10); $^1$H NMR (400 MHz, DMSO-d6) δ 1.14 (t, 3H, J=7.3 Hz), 2.03 (s, 3H), 2.17-2.42 (m, 2H), 6.61 (d, 1H, J=15.8 Hz), 7.25 (td, 1H, J=8.5 Hz, 2.9 Hz), 7.35 (dd, 1H, J=9.6 Hz, 2.8 Hz), 7.48 (dd, 1H, J=8.7 Hz, 5.5 Hz), 7.56 (d, 1H, J=15.8 Hz), 7.98 (dd, 1H, J=10.0 Hz, 1.3 Hz), 9.15 (s, 1H), 9.20 (s, 1H), 10.82 (s, 1H); ESIMS(+) m/z 386 $[M+H]^+$; HPLC 99%.

Example 35: (E)-3-(3-(3,5-dimethylphenyl)-7-fluoro-2-(1-fluoroethyl)-4-oxo-3,4-dihydroquinazolin-6-yl)acrylic acid (5v)

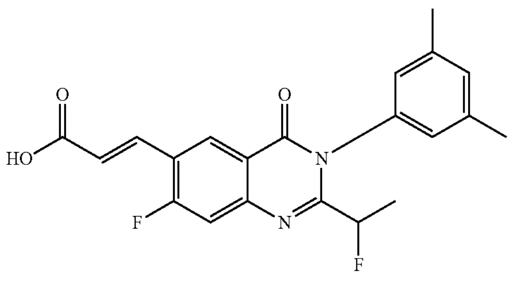 [SMILES: Cc1cc(C)cc(Cn2c(C(C)F)nc3cc(F)c(/C=C/C(=O)O)cc3c2=O)c1]

The mixture solution of 4v (1.7 g, 3.88 mmol), $Pd(OAc)_2$ (70 mg, 0.31 mmol), $[(t-Bu)_3PH]BF_4$ (90 mg, 0.31 mmol), acrylic acid (0.5 mL, 7.77 mmol), $Cs_2CO_3$ (1.9 g, 5.83 mmol) in DMF (14 mL) was irritated by MW 200 W 25 min. After cooling to rt., the resulting solution was filtered and the filtrate was extracted with DCM (50 mL), $NaHCO_3$ (sat.) (75 mL). However it showed serious emulsification. The mixture solution was concentrated under 60° C. and separated. The organic layer was collected and further extracted with $NaHCO_3$ (50 mL). The water layer was combined and acidified by 3 N HCl in ice-bath until pH=2 (some solid was precipitated). The resulting solution was filtered and the filtered solid was dried in vacuo to give the product as yellow solid. (1.0 g, 67%). Rf=0.04 (EA/HEX=1/2);

(E)-3-(3-(3,5-dimethylphenyl)-7-fluoro-2-(1-fluoroethyl)-4-oxo-3,4-dihydroquinazolin-6-yl)-N-((tetrahydro-2H-pyran-2-yl)oxy)acrylamide (6v)

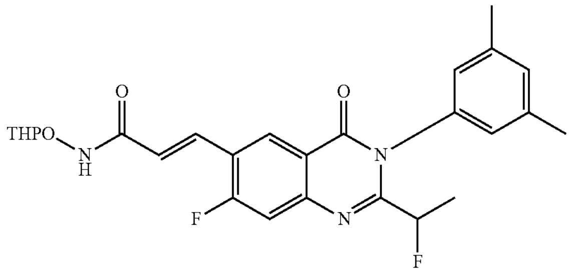

The mixture solution of 5v (1.0 g 2.60 mmol), EDCI HCl (1.0 g, 5.20 mmol), HOBt (0.5 g, 3.90 mmol) in DMF (5 mL) was added TEA (0.7 mL, 5.20 mmol) and stirred at rt. for 1.5 h. the reaction solution was added another EDCI (0.5 g, 2.60 mmol) and stirred for additional 1 h. The resulting solution was added $NH_2OTHP$ (0.3 g, 2.86 mmol) and stirred at rt. for 16. The resulting mixture was added $Et_3N$ (0.02 mL, 0.17 mmol) and stirred at rt. for 16 h. The resulting solution was concentrated and extracted with DCM (75 mL×2) and $H_2O$ (75 mL). The organic layer was dried over MgSO4 and concentrated to give the crude product as brown oil. The crude was purified by flash column (¢4.5×9.5, EA/Hex=2/5-3/2) to give the product as yellow foam. (1.1 g, 88%). Rf=0.78 (MeOH/DCM=1/10);

Example 36: (E)-3-(3-(3,5-dimethylphenyl)-7-fluoro-2-(1-fluoroethyl)-4-oxo-3,4-dihydroquinazolin-6-yl)-N-hydroxyacrylamide (7v, Compound 19)

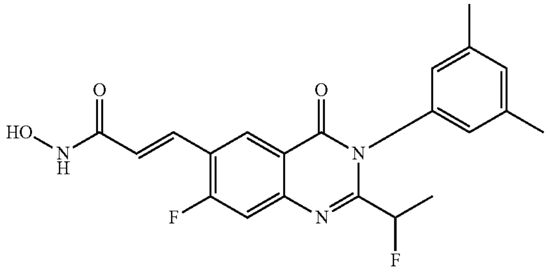 [SMILES: Cc1cc(C)cc(Cn2c(C(C)F)nc3cc(F)c(/C=C/C(=O)NO)cc3c2=O)c1]

The mixture solution of 6v (1.1 g, 2.28 mmol) in MeOH (38 mL) was added TFA (0.5 mL, 6.83 mmol) and stirred at 70° C. for 2.5 h. The resulting solution was extracted with DCM (50 mL×2) and H2O (50 mL). The organic layer was dried over MgSO4 and concentrated to give the crude. The crude was purified by flash column (¢4×8, MeOH/DCM=1/60-1/30) to give the product as orange solid. The solid was washed with Hex (50 mL) to give the product as clear orange solid. (0.7 g, 73%). Rf=0.45 (MeOH/DCM=1:10); $^1$H NMR (400 MHz, DMSO-d6) δ 1.55 (dd, 3H, J=24.5 Hz, 6.3 Hz), 2.34 (s, 6H), 5.22 (dq, 1H, J=46.4 Hz, 8.1 Hz), 6.72 (d, 1H, J=16.0 Hz), 7.05 (s, 1H), 7.11 (s, 1H), 7.18 (s, 1H), 7.61 (d, 1H, J=15.9 Hz), 7.69 (d, 1H, J=11.6 Hz), 8.37 (d, 1H, J=8.1 Hz), 9.20 (br, 1H), 10.90 (s, 1H); ESIMS(+) m/z 400 $[M+H]^+$; HPLC 99%.

Example 37: (E)-3-(3-(2,6-diisopropylphenyl)-7-fluoro-2-methyl-4-oxo-3,4-dihydroquinazolin-6-yl)-N-hydroxyacrylamide (5h, Compound 9)

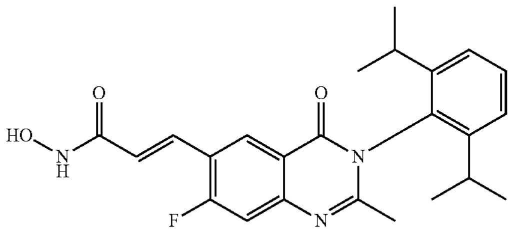 [SMILES: Cc1nc2cc(F)c(/C=C/C(=O)NO)cc2c(=O)n1Cc1c(C(C)C)cccc1C(C)C]

The slurry solution of NaOH (0.3 g, 7.91 mmol) in $NH_2OH$ (2 M in MeOH, 30 mL) was added 4h (1.7 g, 3.96 mmol) at 0° C. and stirred for 0.5 h (no reaction). The slurry solution was warmed to rt. and stirred for 0.5 h (reaction slow). The reaction solution was warm to 30° C. and stirred for 1 h (starting not finished but by-product getting more) then quenched with 2 N HCl until pH=2. The mixture solution was concentrated and extracted with DCM (100 mL×2), H2O (100 mL) and NaCl (sat. 30 mL). The organic layer was dried over MgSO4 and concentrated to give the crude as dark oil. The crude was purified by flash column (¢4.5×8.5, MeOH/DCM=1/80-1/40) to give the product as clear orange solid. (0.9 g, 53%). Rf=0.18 (MeOH/DCM=1: 20); $^1H$ NMR (400 MHz, DMSO-d6): δ 1.01 (s, 3H), 1.03 (s, 3H), 1.16 (s, 3H), 1.18 (s, 3H), 2.06 (s, 3H), 2.45 (p, 2H, J=6.8 Hz), 6.74 (d, 1H, J=15.9 Hz), 7.39 (s, 1H), 7.42 (s, 1H), 7.51-7.61 (m, 3H), 8.40 (d, 1H, J=8.1 Hz), 9.21 (br, 1H), 10.83 (s, 1H); ESIMS(+) m/z 424 [M+H]+; HPLC 99%.

Example 38: (E)-3-(3-(2,6-dichlorophenyl)-7-fluoro-2-methyl-4-oxo-3,4-dihydroquinazolin-6-yl)-N-hydroxyacrylamide (5i, Compound 5)

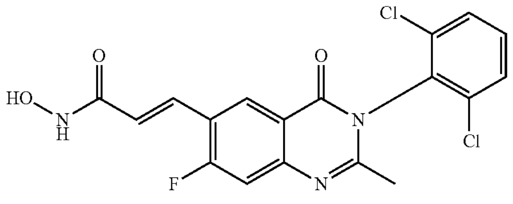 [SMILES: Cc1nc2cc(F)c(/C=C/C(=O)NO)cc2c(=O)n1Cc1c(Cl)cccc1Cl]

The slurry solution of NaOH (0.6 g, 14.10 mmol) in $NH_2OH$ (53 mL) was added 4i (3.0 g, 7.05 mmol) at rt. and stirred for 0.5 h. The resulting solution was quenched with 2 N HCl (33 mL) until pH=2 and extracted with DCM (75 mL×2). The organic layer was dried over $MgSO_4$, filtered and concentrated in vacuo to give the crude as dark oil. The crude was purified by flash column (¢4.5×8.5, MeOH/DCM=1/70-1/30) to give the product as orange solid. The solid was further washed with MeOH/EA=8.5/1.5 mL to give the product as orange solid. (0.9 g, 31%). Rf=0.2 (MeOH/DCM=1:10); $^1H$ NMR (400 MHz, DMSO-d6) δ 2.16 (s, 3H), 6.72 (d, 1H, J=15.9 Hz), 7.57-7.69 (m, 3H), 7.81 (s, 1H), 7.83 (s, 1H), 8.40 (d, 1H, J=8.1 Hz), 9.21 (s, 1H), 10.91 (s, 1H); ESIMS(+) m/z 406 $[M-H]^-$; HPLC 96%.

Example 39: (E)-3-(3-(2,6-dimethylphenyl)-7-fluoro-2-methyl-4-oxo-3,4-dihydroquinazolin-6-yl)-N-hydroxyacrylamide (5j, Compound 1)

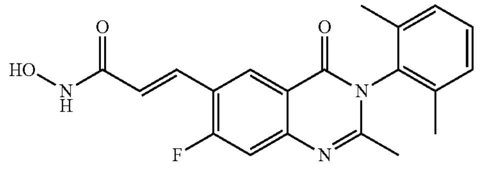 [SMILES: Cc1cccc(C)c1-n1c(C)nc2cc(F)c(/C=C/C(=O)NO)cc2c1=O]

The slurry solution of NaOH (0.4 g, 9.04 mmol) in $NH_2OH$ (2 M in MeOH, 34 mL) was added 4j (1.7 g, 4.52 mmol) at 0° C. and stirred for 1 h. The reaction solution was warmed to rt. for another 30 min. The resulting solution was quenched with 3 N HCl (19.5 mL) until pH=2 and stirred at rt. for 10 min. The mixture solution was concentrated and added H2O (50 mL) and DCM (50 mL) under sonication 1 min. the organic layer was separated and concentrated (slurry) to give the crude. The crude was washed with EA (5 mL) to give the product as clear orange solid. (0.5 g, 28%). The water layer was extracted with DCM (30 mL) and it showed some slurry solid. The solid was filtered and the solid was further washed with the solution of EA (20 mL) and MeOH (1 mL) to give the product as clear orange solid. (0.8 g, 46%). Total (1.2 g, 74%) Rf=0.01 (MeOH/DCM=1: 10); $^1H$ NMR (400 MHz, DMSO-d6): δ 2.00 (s, 6H), 2.07 (s, 3H), 6.17 (d, 1H, J=16.0 Hz), 7.29-7.36 (m, 3H), 7.56 (d, 1H, J=3.2 Hz), 7.60 (d, 1H, J=7.5 Hz), 8.38 (d, 1H, J=8.1 Hz), 9.22 (br, 1H), 10.92 (s, 1H); ESIMS(+) m/z 368 [M+H]+; HPLC 93%.

Example 40: (E)-3-(3-(2,6-dimethylphenyl)-5-fluoro-2-methyl-4-oxo-3,4-dihydroquinazolin-6-yl)-N-hydroxyacrylamide (5k, Compound 3)

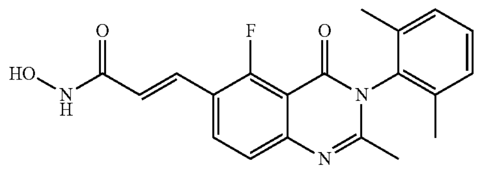 [SMILES: Cc1cccc(C)c1-n1c(C)nc2ccc(/C=C/C(=O)NO)c(F)c2c1=O]

The slurry solution of NaOH (0.2 g, 6.10 mmol) in $NH_2OH$ (2 M in MeOH, 23 mL) was added 4k (1.2 g, 3.05 mmol) at rt. and stirred for 0.5 h. The resulting solution was quenched with 2N HCl (17 mL) until pH=2 and extracted with DCM (75 mL) and H2O (50 mL), NaCl (sat. 20 mL). The slurry solution was filtered and the filtered solid was washed with ether to give the product as yellow solid. The crude was further washed with EA/MeOH=5/1 mL to give the product as yellowish solid. (0.3, 24%). Rf=0.01 (MeOH/DCM=1:10); $^1H$ NMR (400 MHz, DMSO-d6): δ 2.02 (s, 6H), 2.06 (s, 3H), 6.66 (d, 1H, J=15.9 Hz), 7.29-7.35 (m, 3H), 7.53-7.61 (m, 2H), 8.09 (t, 1H, J=8.0 Hz), 9.17 (br, 1H), 10.96 (s, 1H); ESIMS(+) m/z 368 $[M+H]^+$; HPLC 99%.

Example 41: (E)-3-(3-(2,6-dimethylphenyl)-8-fluoro-2-methyl-4-oxo-3,4-dihydroquinazolin-6-yl)-N-hydroxyacrylamide (5l, Compound 10)

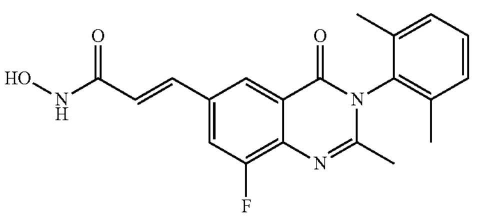 [SMILES: Cc1cccc(C)c1-n1c(C)nc2c(F)cc(/C=C/C(=O)NO)cc2c1=O]

The slurry solution of NaOH (0.7 g, 16.84 mmol) in $NH_2OH$ (63 mL) was added 4l (3.2 g, 8.41 mmol) at 0° C. for 0.5 h The resulting yellow solution was extracted with $CHCl_3$ (250 mL×2), NaCl (sat. 200 mL), 2 N HCl (26 mL) (yellow to colorless). The organic layer was concentrated in vacuo to give the crude as yellow oil. The crude was purified by flash column (¢4.5×8, MeOH/$CHCl_3$=1/70-1/5) and the pure fraction was collected and concentrated to give the colorless oil. The oil was diluted with EA (5 mL) and precipitated by Hex (50 mL) to give the product as white solid. (1.2 g, 39%). The mixture fraction was collected and concentrated to give the red-orange oil. The oil was diluted with EA (10 mL) and sonicated at rt. for 4 mins to give the product as beige solid. (0.8 g, 24%). Total (1.9 g, 63%) Rf=0.2 (MeOH/DCM=1:10); $^1$H NMR (400 MHz, DMSO-d6) δ 2.01 (s, 6H), 2.10 (s, 3H), 6.62 (d, 1H, J=15.8 Hz), 7.29-7.37 (m, 3H), 7.57 (d, 1H, J=15.8 Hz), 7.99 (d, 1H, J=11.4 Hz), 8.11 (s, 1H), 9.17 (br, 1H), 10.85 (s, 1H); ESIMS(+) m/z 390 $[M+Na]^+$; HPLC 99%.

Example 42: (E)-3-(3-(2,6-difluorophenyl)-7-fluoro-2-methyl-4-oxo-3,4-dihydroquinazolin-6-yl)-N-hydroxyacrylamide (5n, Compound 12)

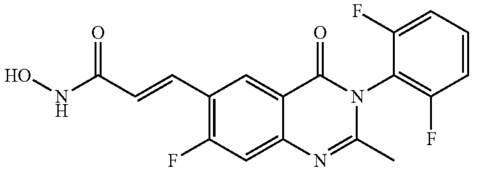 [SMILES: Cc1nc2cc(F)c(/C=C/C(=O)NO)cc2c(=O)n1-c1c(F)cccc1F]

The slurry solution of NaOH (0.4 g, 8.96 mmol) in $NH_2OH$ (34 mL) was added 4n (1.7 g, 4.48 mmol) at 0° C. for 0.5 h then stirred at rt for 1 h. The resulting yellow solution was quenched with 2 N HCl (10 mL) and extracted with DCM (100 mL), H2O (100 mL) and NaCl (sat. 50 mL), however, it showed serious emulsification. To combined the organic layer and the emulsified layer, the solution was concentrated until ti remained 20 mL. The residue was added ether (10 mL) and Hex (10 mL) and sonicated for 1 min. The jelly solution was filtered and the filtrate was purified by flash column (¢3.5×7, MeOH/DCM=1/15) to give the product as red-orange oil. The oil was precipitated by Hex (30 mL) to give the product as red-orange solid. (49 mg, 3%). Rf=0.25 (MeOH/DCM=1:10); $^1$H NMR (400 MHz, DMSO-d6) δ 2.27 (s, 3H), 6.72 (d, 1H, J=16.0 Hz), 7.47 (t, 2H, J=8.3 Hz), 7.60 (d, 1H, J=24.8 Hz), 7.61 (d, 1H, J=2.8 Hz), 7.71-7.78 (m, 1H), 8.39 (d, 1H, J=8.1 Hz), 9.21 (br, 1H), 10.91 (s, 1H); ESIMS(+) m/z 398 $[M+Na]^+$; HPLC 98%.

Example 43: (E)-3-(3-(2,6-difluorophenyl)-2-ethyl-7-fluoro-4-oxo-3,4-dihydroquinazolin-6-yl)-N-((tetrahydro-2H-pyran-2-yl)oxy)acrylamide (5o)

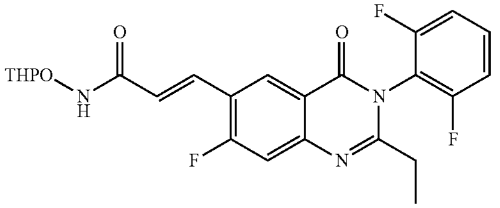

The mixture solution of 4o (2.9 g, 6.09 mmol), EDCI HCl (1.8 g, 9.14 mmol), HOBt (1.1 g, 7.92 mmol), $Et_3N$ (2.5 mL, 18.28 mmol) in DMF (12 mL) was stirred at rt. for 1 h. The resulting solution was added $NH_2OTHP$ (0.8 g, 6.70 mmol) and stirred at rt. for another 4.5 h. The resulting solution was extracted with DCM (100 mL×2) and $H_2O$ (100 mL). The organic layer was dried over MgSO4 and concentrated to give the crude product as yellow oil. The crude was purified by flash column (¢4.5×8, EA/Hex=1/5-1/4.5) to give the product as yellowish oil. The oil was precipitated by EA (5 mL) and Hex (10 mL) to give the product as white solid. (1.9 g, 66%). Rf=0.53 (MeOH/DCM=1/10);

Example 44: (E)-3-(3-(3,5-dimethylphenyl)-7-fluoro-2-methyl-4-oxo-3,4-dihydroquinazolin-6-yl)-N-hydroxyacrylamide (5p, Compound 18)

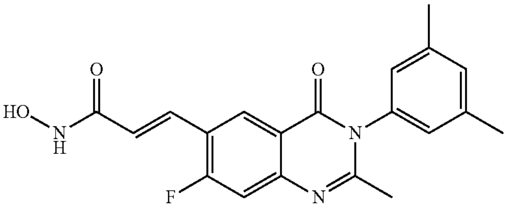 [SMILES: Cc1cc(C)cc(-n2c(C)nc3cc(F)c(/C=C/C(=O)NO)cc3c2=O)c1]

The slurry solution of NaOH (0.5 g, 12.09 mmol) in $NH_2OH$ (46 mL) was added 4p (2.3 g, 6.05 mmol) at 0° C. and stirred for 3.5 h. The resulting solution was quenched with 2 N HCl (15 mL) until pH=7 and extracted with DCM (75 mL×2). The organic layer was dried over $MgSO_4$, filtered and concentrated in vacuo to give the crude as brown oil. The crude was purified by flash column (¢4.5×8, MeOH/DCM=1/70-1/25) to give the product as orange-red solid. The solid was added EA (5 mL) and precipitated by Hex (20 mL) to give the product as orange-red solid (0.9 g, 41%). Rf=0.18 (MeOH/DCM=1:10); $^1$H NMR (400 MHz, DMSO-d6) δ 2.14 (s, 3H), 2.33 (s, 6H), 6.68 (d, 1H, J=15.9 Hz), 7.04 (s, 2H), 7.15 (s, 1H), 7.51 (d, 1H, J=11.8 Hz), 7.58 (d, 1H, J=15.9 Hz), 8.31 (d, 1H, J=8.2 Hz), 9.21 (br, 1H), 10.90 (s, 1H); ESIMS(+) m/z 368 [M+H]+; HPLC 96%.

Example 45: (E)-ethyl 3-(3-(2,6-dimethylphenyl)-2,7-dimethyl-4-oxo-3,4-dihydroquinazolin-6-yl)acrylate (5q)

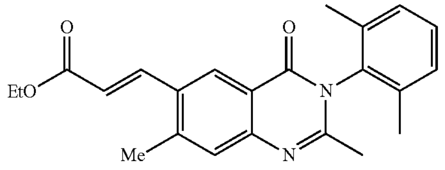 [SMILES: CCOC(=O)/C=C/c1cc2c(=O)n(-c3c(C)cccc3C)c(C)nc2cc1C]

The mixture solution of 4q (0.8 g, 1.91 mmol), pd(dba)3 (35 mg, 0.04 mmol), [(t-Bu)3PH]BF4 (44 mg, 0.15 mmol) in THF (4 mL) was added Me2Zn (3.2 mL, 3.82 mmol, 1.2 M in toluene) and irritated by MW 250 W 30 min.[mode: standard, temperature=120, run time=30 min, hold time=30 min, open vessel] after cooling to rt., the resulting solution was filtered and the filtrate was added H2O (75 mL) and extracted with DCM (75 mL×2). The organic layer was dried over $MgSO_4$, filtered and concentrated in vacuo to give the crude as orange oil. The crude was purified by flash column (¢3.5×7) to give product as yellow solid. (0.3 g, 35%). Rf=0.25 (EA/Hex=1:2); ESIMS(+) m/z 377 $[M+H]^+$ (E)-ethyl 3-(3-(2,6-dimethylphenyl)-2-ethyl-7-methyl-4-oxo-3,4-dihydroquinazolin-6-yl)acrylate (5r)

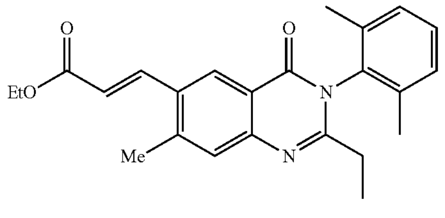

The mixture solution of 4r (1.5 g, 3.65 mmol), pd(dba)3 (64 mg, 0.07 mmol), [(t-Bu)3PH]BF4 (84 mg, 0.29 mmol) in THF (9 mL) was added Me2Zn (6.1 mL, 7.30 mmol, 1.2 M in toluene) and irritated by MW 250 W 30 min.[mode: standard, temperature=120, run time=30 min, hold time=30 min, open vessel] after cooling to rt., the resulting solution was filtered and the filtrate was added H2O (75 mL) and extracted with DCM (75 mL×2). The organic layer was dried over $MgSO_4$, filtered and concentrated in vacuo to give the crude as yellow oil. The crude was purified by flash column (¢4.5×7.5, EA/Hex=1/10-1/7) to give product as white solid. (0.7 g, 50%). Rf=0.43 (EA/Hex=1:2); ESIMS(+) m/z 391 $[M+H]^+$ Example 46: (E)-3-(3-(2,6-difluorophenyl)-2-ethyl-7-fluoro-4-oxo-3,4-dihydroquinazolin-6-yl)-N-hydroxyacrylamide (60, Compound 13)

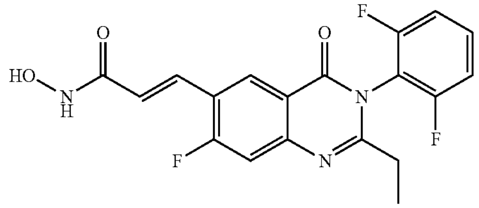 [SMILES: CCc1nc2cc(F)c(/C=C/C(=O)NO)cc2c(=O)n1-c1c(F)cccc1F]

The mixture solution of 5o (1.9 g, 4.01 mmol) in MeOH (66 mL) was added TFA (0.9 mL, 12.04 mmol) and stirred at 70° C. for 2 h. The resulting solution was extracted with DCM (150 mL×2) and H2O (100 mL). The organic layer was dried over MgSO4 and concentrated to give the crude. The crude was purified by flash column (¢4.5×6, MeOH/DCM=1/50/-1/40) to give the product as white solid. (1.4 g, 86%). Rf=0.25 (MeOH/DCM=1:10); $^1H$ NMR (400 MHz, DMSO-d6) δ 1.15 (t, 3H, J=7.3 Hz), 2.46 (q, 2H, J=7.3 Hz), 6.72 (d, 1H, J=15.9 Hz), 7.47 (t, 2H, J=8.3 Hz), 7.61 (t, 2H, J=16.5 Hz), 7.71-7.78 (m, 1H), 8.39 (d, 1H, J=8.1 Hz), 9.21 (br, 1H), 10.91 (s, 1H); ESIMS(+) m/z 388 $[M-H]^-$; 4HPLC 98%.

Example 47: (E)-3-(3-(2,6-dimethylphenyl)-2,7-dimethyl-4-oxo-3,4-dihydroquinazolin-6-yl)-N-hydroxyacrylamide (6q, Compound 16)

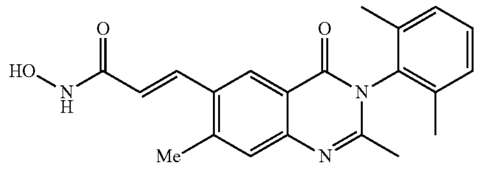 [SMILES: Cc1cc2nc(C)n(-c3c(C)cccc3C)c(=O)c2cc1/C=C/C(=O)NO]

The slurry solution of NaOH (53 mg, 1.33 mmol) in $NH_2OH$ (5 mL) was added 5q (0.3 g, 0.66 mmol) at 0° C. and stirred for 2 h. The resulting solution was quenched with 1 N HCl (10 mL) until pH=7 and extracted with DCM (75 mL×2), MeOH (5 mL). The organic layer was dried over $MgSO_4$, filtered and concentrated in vacuo to give the crude as orange oil. The crude was purified by flash column (¢3.5×8, MeOH/DCM=1/60-1/25) to give the product as orange solid (0.2 g, 69%). Rf=0.25 (MeOH/DCM=1:10); $^1H$ NMR (400 MHz, DMSO-d6) δ 1.99 (s, 6H), 2.05 (s, 3H), 2.54 (s, 3H), 6.53 (d, 1H, J=15.6 Hz), 7.29-7.36 (m, 3H), 7.58 (s, 1H), 7.72 (d, 1H, J=15.6 Hz), 8.24 (s, 1H), 9.15 (br, 1H), 10.82 (s, 1H); ESIMS(+) m/z 364 $[M+H]^+$; HPLC 99%.

Example 48: 3-(2,6-dibromo-4-fluorophenyl)-2-ethyl-7-fluoro-6-iodoquinazolin-4(3H)-one (3x)

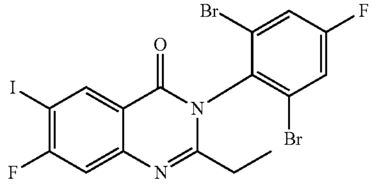 [SMILES: CCc1nc2cc(F)c(I)cc2c(=O)n1-c1c(Br)cc(F)cc1Br]

The solution of 2a (5.0 g, 17.79 mmol) in pyridine (24 mL) was added propionic anhydride (3.4 mL, 26.69 mmol) dropwise at 0° C. then stirred at rt. for 10 min. The resulting solution was added $P(OPh)_3$ (6 mL, 23.13 mmol) nd irritated by MW 250 W 20 min. The reaction mixture was added 2,6-dibromo-4-fluoroaniline (6.2 g, 23.13 mmol) and irritated by MW 250 W 20 min. After cooling to rt., the resulting solution was quenched with 3 N HCl (72 mL) until pH=2 and extracted with DCM (75 mL×2). The organic layer was dried over $MgSO_4$ and concentrated to give the crude as yellow oil. The crude was purified by flash column (¢4.5×9, EA/Hex=1/10) to give the product as yellow oil. The oil was diluted with Hex (70 mL) and sonicated in ice-bath to precipitate the product as white solid. (3.8 g, 38%). Rf=0.58 (EA/Hex=1:2);

(E)-ethyl 3-(3-(2,6-dibromo-4-fluorophenyl)-2-ethyl-7-fluoro-4-oxo-3,4-dihydroquinazolin-6-yl) acrylate (4x)

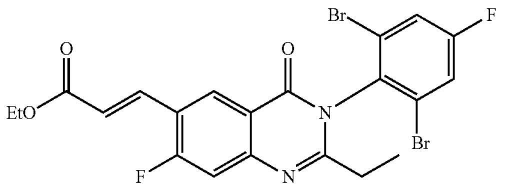 [SMILES: CCOC(=O)/C=C/c1cc2c(=O)n(-c3c(Br)cc(F)cc3Br)c(CC)nc2cc1F]

The reaction mixture of 3x (3.8 g, 6.67 mmol), $Pd(OAc)_2$ (74 mg, 0.33 mmol), $PPh_3$ (0.2 g, 0.67 mmol), NaOAc (0.8 g, 10.00 mmol), ethyl acrylate (0.8 mL, 7.33 mmol) in DMA (9 mL) was irritated by MW 250 W 20 min. After cooling to rt., the resulting solution was filtered and extracted with DCM (75 mL×2) and saturated NaCl (75 mL). The organic layer was dried over $MgSO_4$, filtered and concentrated in vacuo to give the crude as dark oil. The crude was purified by flash column (¢4.5×9, EA/HEX=1/9.5) to give the product as yellow solid. The solid was washed with Hex (10 mL) to give the product as yellow solid. (0.6 g, 17%). Rf=0.58 (EA/Hex=1:2); ESIMS(+) m/z 543 $[M+H]^+$ (E)-ethyl 3-(2-ethyl-7-fluoro-3-(4-fluoro-2,6-dimethylphenyl)-4-oxo-3,4-dihydroquinazolin-6-yl)acrylate (5x)

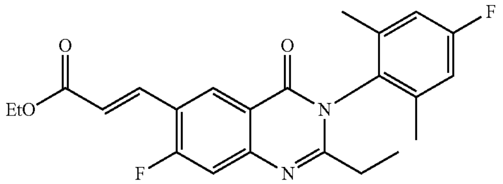 [SMILES: CCOC(=O)/C=C/c1cc2c(=O)n(-c3c(C)cc(F)cc3C)c(CC)nc2cc1F]

The mixture solution of 4x (0.8 g, 1.37 mmol), Pd2(dba)3 (27 mg, 0.03 mmol), [(t-Bu)3PH]BF4 (32 mg, 0.11 mmol) in THF (3 mL) was added Me2Zn (4.6 mL, 1.2 M in toluene) was irritated by MW [Mode: standard, 200W, run time: 30 min, hold time: 55 min]. The resulting solution was filtered and the filtrate was extracted with DCM (50 mL×2), H2O (50 mL). The organic layer was dried over MgSO4 and concentrated to give the crude as orange oil. The crude was purified by flash column (¢3.5×12, EA/HEX=1/10-1/7.5) to give the product as yellow solid. (0.4 g, 73%). Rf=0.35 (EA/Hex=1:5); ESIMS(+) m/z 413 $[M+H]^+$ Example 49: (E)-3-(2-ethyl-7-fluoro-3-(4-fluoro-2,6-dimethylphenyl)-4-oxo-3,4-dihydroquinazolin-6-yl)-N-hydroxyacrylamide (Compound 24, 6x)

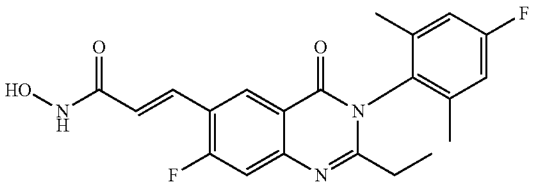 [SMILES: CCc1nc2cc(F)c(/C=C/C(=O)NO)cc2c(=O)n1-c1c(C)cc(F)cc1C]

The slurry solution of NaOH (0.1 g, 2.09 mmol) in $NH_2OH$ (8 mL) was added 5x (0.4 g, 1.04 mmol) at 0° C. and stirred at rt. for 2.5 h. The resulting solution was quenched with 1 N HCl (8 mL) until pH=7 and extracted with DCM (50 mL×3), H2O (50 mL). The organic layer was dried over $MgSO_4$, filtered and concentrated in vacuo to give the crude as orange oil. The crude was purified by flash column (¢2.5×8, MeOH/DCM=1/50-1/35) to give the product as clear orange solid. The oil was diluted with DCM (3 mL), MeOH (1 drop) and added Hex (20 mL) under sonicator for 2 mins to precipitate the product as white solid. The solid was dissolved with MeOH (3 mL), DCM (1 mL) and do the recrystallized to give the product (80 mg, 19%). Rf=0.35 (MeOH/DCM=1:10); $^1H$ NMR (400 MHz, DMSO-d6) δ 1.16 (t, 3H, J=7.2 Hz), 2.0 (s, 6H), 2.24 (q, 2H, J=7.2 Hz), 6.71 (d, 1H, J=15.9 Hz), 7.18 (s, 1H), 7.20 (s, 1H), 7.57-7.62 (m, 2H), 8.38 (d, 1H, J=8.2 Hz), 9.19 (s, 1H), 10.88 (s, 1H); ESIMS(+) m/z 400 $[M+H]^+$; HPLC 93%.

Example 50: (E)-3-(3-(2,6-dimethylphenyl)-2-ethyl-7-methyl-4-oxo-3,4-dihydroquinazolin-6-yl)-N-hydroxyacrylamide (6r, Compound 17)

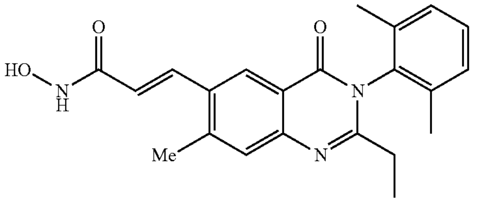 [SMILES: CCc1nc2cc(C)c(/C=C/C(=O)NO)cc2c(=O)n1-c1c(C)cccc1C]

The slurry solution of NaOH (0.2 g, 3.64 mmol) in $NH_2OH$ (13 mL) was added 5r (0.7 g, 1.82 mmol) at 0° C. and stirred for 3.5 h. The resulting solution was quenched with 1 N HCl (9 mL) until pH=7 (yellow to colorless slurry). The slurry solution was added H2O (30 mL) and filtered. The filtered solid was dissolved with MeOH (50 mL) and the filtrate was and extracted with DCM (50 mL×2), MeOH (10 mL). The organic layer was dried over $MgSO_4$, filtered and concentrated in vacuo to give the crude as yellow oil. The crude was purified by flash column (¢3.5×7, MeOH/DCM=1/100-1/30) to give the product as orange solid (0.5 g, 78%). Rf=0.4 (MeOH/DCM=1:10); $^1$H NMR (400 MHz, DMSO-d6) δ 1.14 (t, 3H, J=7.3 Hz), 1.97 (s, 6H), 2.19 (q, 2H), 2.54 (s, 3H), 6.53 (d, 1H, J=15.6 Hz), 7.28-7.36 (m, 3H), 7.63 (s, 1H), 7.72 (d, 1H, J=15.6 Hz), 8.25 (s, 1H), 9.15 (br, 1H), 10.82 (s, 1H); ESIMS(+) m/z 376 $[M-H]^-$; HPLC 99%.

Example 51: (E)-methyl 3-(3-(2,6-dimethylphenyl)-2-ethyl-7-fluoro-4-oxo-3,4-dihydroquinazolin-6-yl) acrylate (3af)

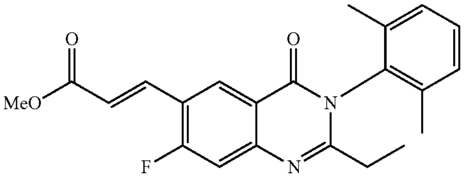 [SMILES: CCc1nc2cc(F)c(/C=C/C(=O)OC)cc2c(=O)n1-c1c(C)cccc1C]

The reaction mixture of 3d (2.5 g, 5.92 mmol), $Pd(OAc)_2$ (67 mg, 0.30 mmol), $PPh_3$ (0.2 g, 0.59 mmol), NaOAc (0.7 g, 8.89 mmol), ethyl acrylate (0.6 mL, 6.52 mmol) in DMA (12 mL) was irritated by MW 250 W 25 min. After cooling to rt., the resulting solution was filtered and the filtrate was extracted with DCM (75 mL×2) and saturated NaCl (sat. 75 mL). The organic layer was dried over $MgSO_4$, filtered and concentrated in vacuo to give the crude as black oil. The oil was added EA (5 mL) to precipitate the product as brown solid. (0.7 g, 32%) The filtrate was purified by flash column (¢3.5×10, EA/Hex=1/10-1/6) to give the beige solid. The solid was washed with Hex (10 mL) to give the product as beige solid. (70 mg, 3%). Total (0.8 g, 35%); Rf=0.6 (EA/Hex=1:2);

(E)-methyl 3-(3-(2,6-dimethylphenyl)-2-ethyl-7-methoxy-4-oxo-3,4-dihydroquinazolin-6-yl)acrylate (4af)

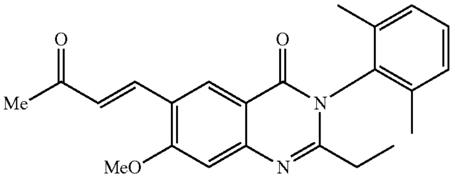 [SMILES: CCc1nc2cc(OC)c(/C=C/C(C)=O)cc2c(=O)n1-c1c(C)cccc1C]

The mixture solution of 3af (0.8 g, 2.08 mmol), NaOMe (0.3 g, 6.23 mmol) in MeOH (2 mL), DMF (0.7 mL) was heated at 80° C. for 5 h. the resulting solution was quenched with H2O and extracted with DCM (50 mL×2). The organic layer was dried over $MgSO_4$, filtered and concentrated in vacuo to give the crude as yellow oil. The oil was purified by flash column (¢3.5×10, EA/Hex=1/6-1/3.5) to give the beige solid. (0.3 g, 31%). Rf=0.25 (EA/Hex=1:2);

Example 52: (E)-3-(3-(2,6-dimethylphenyl)-2-ethyl-7-methoxy-4-oxo-3,4-dihydroquinazolin-6-yl)-N-hydroxyacrylamide (Compound 32, 5af)

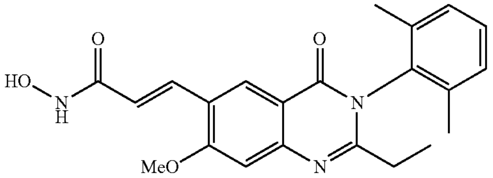 [SMILES: CCc1nc2cc(OC)c(/C=C/C(=O)NO)cc2c(=O)n1-c1c(C)cccc1C]

The slurry solution of NaOH (0.5 g, 12.18 mmol) in $NH_2OH$ (45 mL) was added 4af (0.23 g, 0.64 mmol) at 0° C. and stirred for 10 min. The reaction solution was warmed to rt. and stirred for additional 1.5 h. The resulting solution was added another $NH_2OH$ (2.5 mL) and stirred for another 2.5 h. The reaction solution was quenched with 1 N HCl (6.5 mL) until pH=7 (yellow to colorless) and extracted with DCM (25 mL×2), H2O (25 mL). The organic layer was dried over $MgSO_4$, filtered and concentrated in vacuo to give the crude as yellow oil. The crude was purified by flash column (¢2.5×8, MeOH/DCM=1/50-1/30) to give the product as white solid. The solid was dissolved with DCM (5 mL), MeOH (1 mL) then concentrated until the solvent remained 1.5 mL. The residue was added EA (1 mL) and sonicated until the solution became slurry. The slurry solution was added Hex (15 mL) and put at 0° C. to give the product as white solid. (0.1 g, 37%). Rf=0.38 (MeOH/DCM=1:10); $^1$H NMR (400 MHz, DMSO-d6) δ 1.16 (t, 3H, J=7.3 Hz), 1.98 (s, 6H), 2.20 (q, 2H, J=7.3 Hz), 4.04 (s, 3H), 6.63 (d, 1H, J=15.9 Hz), 7.24 (s, 1H), 7.28-7.36 (m, 3H), 7.74 (d, 1H, J=15.9 Hz), 8.24 (s, 1H), 9.10 (br, 1H), 10.77 (s, 1H); ESIMS(+) m/z 394 $[M+H]^+$; HPLC 98%.

Example 53: (E)-ethyl 3-(3-(2,6-dimethylphenyl)-7-fluoro-2-methyl-4-oxo-1,2,3,4-tetrahydroquinazolin-6-yl)acrylate (61)

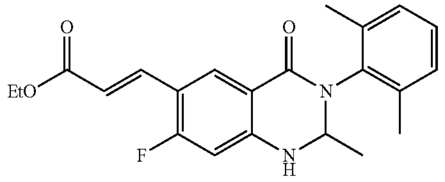 [SMILES: CCOC(=O)/C=C/c1cc2c(cc1F)NC(C)N(c1c(C)cccc1C)C2=O]

The mixture of 4j (1.2 g, 3.05 mmol), NaBH4 (0.2 g, 6.10 mmol) was added THF (10 mL) and MeOH (2.5 mL) (baby blue to deep yellow, bubble) and stirred at rt. for 4 h. The resulting brown-green solution was added H2O (50 mL) and extracted with DCM (50 mL×3). The organic layer was dried over MgSO4 and concentrated to give the crude as yellow oil. The crude was purified by flash column (¢4.5×8, EA/DCM/Hex=10/9/1-2/1/1) to give the product as beige solid. (0.5 g, 40%); Rf=0.2 (EA/Hex=1:2); ESIMS(+) m/z 381 $[M-H]^-$;

Example 54: (E)-3-(3-(2,6-dimethylphenyl)-7-fluoro-2-methyl-4-oxo-1,2,3,4-tetrahydroquinazolin-6-yl)-N-hydroxyacrylamide (62, Compound 14)

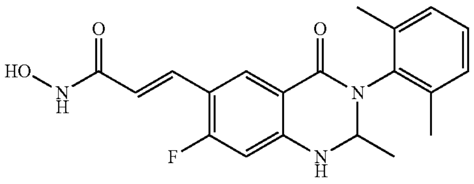 [SMILES: Cc1cccc(C)c1N1C(=O)c2cc(/C=C/C(=O)NO)c(F)cc2NC1C]

The slurry solution of NaOH (0.1 g, 2.46 mmol) in $NH_2OH$ (10 mL) was added 61 (0.5 g, 1.23 mmol) at rt for 3 h. (starting didn't finish) The resulting solution was added $NH_2OH$ (2 mL) and stirred for another 0.5 h. The reaction solution was quenched with 2 N HCl (10 mL) and extracted with DCM (70 mL×2), H2O (70 mL) and NaCl (sat. 10 mL). The organic layer was concentrated in vacuo to give the crude as yellow oil. The crude was purified by flash column (¢3.5×7, MeOH/DCM=1/50-1/40) to give the product as yellow solid. (0.1 g, 29%). Rf=0.18 ($MeOH/CHCl_3$=1:10); $^1H$ NMR (400 MHz, DMSO-d6) δ 1.16 (d, 3H, J=6.0 Hz), 2.15 (s, 3H), 2.20 (s, 3H), 5.20 (q, 1H, J=5.9 Hz), 6.40 (d, 1H, J=15.9 Hz), 6.64 (d, 1H, J=12.3 Hz), 7.14-7.18 (m, 3H), 7.42 (d, 1H, J=15.8 Hz), 7.65 (s, 1H), 7.96 (d, 1H, J=8.4 Hz), 9.04 (br, 1H), 10.68 (s, 1H); ESIMS(+) m/z 368 $[M-H]^-$; HPLC 97%.

Example 55: ethyl 3-(3-(2,6-dimethylphenyl)-7-fluoro-2-methyl-4-oxo-3,4-dihydroquinazolin-6-yl) propanoate (63)

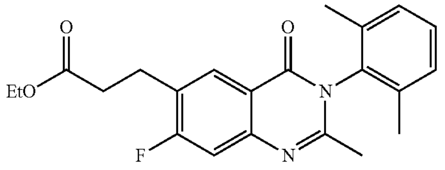 [SMILES: CCOC(=O)CCc1cc2c(=O)n(-c3c(C)cccc3C)c(C)nc2cc1F]

The mixture of 4j (1.2 g, 3.05 mmol), nickel acetate tetrahydrate (0.2 g, 0.89 mmol) was added DCM (12 mL), MeOH (15 mL) and stirred at 0° C. for 5 min. The resulting solution was added NaBH4 (0.2 g, 5.32 mmol) at 0° C. and stirred at same condition for 2 h. (starting didn't finished) The reaction solution was added another $NaBH_4$ (0.1 g, 1.85 mmol) and stirred for 0.5 h. The resulting solution was quenched with H2O (60 mL) and filtered. The filtrate was extracted with DCM (75 mL×2). The organic layer was dried over MgSO4 and concentrated to give the crude as brown oil. The crude was purified by flash column (¢3.5×10, EA/Hex=1/5) to give the product as yellow oil. The oil was added Hex (10 mL) to precipitated the product and put under −20° C. for 4 h to give the product as orange solid. (0.6 g, 42%); Rf=0.25 (EA/Hex=1:2); ESIMS(+) m/z 383 $[M+H]^+$;

Example 56: 3-(3-(2,6-dimethylphenyl)-7-fluoro-2-methyl-4-oxo-3,4-dihydroquinazolin-6-yl)-N-hydroxypropanamide (64, Compound 15)

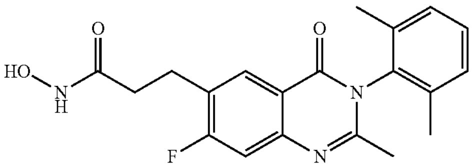 [SMILES: Cc1cccc(C)c1-n1c(C)nc2cc(F)c(CCC(=O)NO)cc2c1=O]

The slurry solution of NaOH (0.1 g, 2.98 mmol) in $NH_2OH$ (11 mL) was added 63 (0.6 g, 1.49 mmol) at 0° C. for 1 h. The resulting solution was quenched with 1 N HCl (11 mL) and extracted with DCM (35 mL×2), H2O (10 mL). The organic layer was concentrated in vacuo to give the crude as yellow oil. The crude was purified by flash column (¢3.5×7, MeOH/DCM=1/30) to give the product as white sticky solid. The solid was dissolved by EA (5 mL) and precipitated by Hex (20 mL) to give the white solid. (0.5 g, 91%). Rf=0.33 ($MeOH/CHCl_3$=1:10); $^1H$ NMR (400 MHz, DMSO-d6) δ 1.99 (s, 6H), 2.15 (s, 3H), 2.05 (s, 3H), 2.35 (t, 1H, J=7.5 Hz), 2.97 (t, 1H, J=7.4 Hz), 7.28-7.36 (m, 3H), 7.46 (d, 1H, J=10.9 Hz), 8.04 (d, 1H, J=8.3 Hz), 8.76 (d, 1H, J=1.0 Hz), 9.12 (br, 1H), 10.43 (s, 1H); ESIMS(+) m/z 392 $[M+Na]^+$; HPLC 100%.

Example 57: 2-ethyl-3-(2-ethylphenyl)-7-fluoro-6-iodoquinazolin-4(3H)-one (3an)

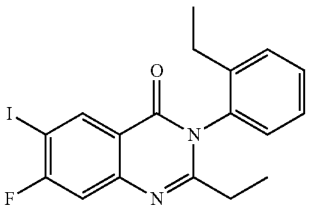 [SMILES: CCc1ccccc1-n1c(CC)nc2cc(F)c(I)cc2c1=O]

The solution of 2a (5.0 g, 17.79 mmol) in pyridine (22 mL) was added propionic anhydride (3.4 mL, 26.69 mmol), $P(OPh)_3$ (6.0 mL, 23.13 mmol) and stirred at rt. for 10 min. The resulting solution was irritated by MW 250 W 20 min. The reaction mixture was added 2-ethylaniline (3 mL, 23.13 mmol) and irritated by MW 250 W 20 min. The resulting solution was quenched with 3 N HCl (68 mL) until pH=2 and extracted with DCM (75 mL×2). The organic layer was dried over $MgSO_4$ and concentrated to give the crude as yellow oil. The crude was purified by flash column (¢4.5×9, EA/HEX=1/9) to give the product as beige solid. The solid was washed with EA (2 mL), Hex (20 mL) to give the product as white solid. (2.6 g, 34%). Rf=0.55 (EA/Hex=1:2);

(E)-ethyl 3-(2-ethyl-3-(2-ethylphenyl)-7-fluoro-4-oxo-3,4-dihydroquinazolin-6-yl)acrylate (4an)

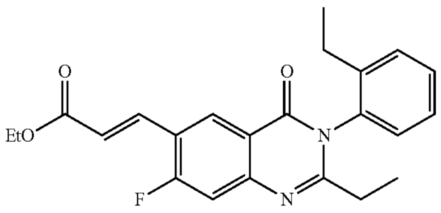 [SMILES: CCOC(=O)/C=C/c1cc2c(=O)n(-c3ccccc3CC)c(CC)nc2cc1F]

The reaction mixture of 3an (2.6 g, 6.11 mmol), $Pd(OAc)_2$ (70 mg, 0.31 mmol), $PPh_3$ (0.2 g, 0.61 mmol), NaOAc (0.8 g, 9.17 mmol), ethyl acrylate (0.7 mL, 6.72 mmol) in DMA (12 mL) was irritated by MW 250 W 25 min. After cooling to rt., the resulting solution was diluted with DCM (30 mL) and filtered. The filtrate was extracted with DCM (50 mL×2) and saturated NaCl (sat. 50 mL). The organic layer was dried over $MgSO_4$, filtered and concentrated in vacuo to give the crude as black oil. The crude was purified by flash column (¢3.5×8, EA/HEX=1/9-1/8) to give the product as brown oil. The oil was added Hex (30 mL) and sonicated for 30 sec to precipitate the product as brown solid. (1.4 g, 59%). Rf=0.55 (EA/Hex=1:2);

Example 58: (E)-3-(2-ethyl-3-(2-ethylphenyl)-7-fluoro-4-oxo-3,4-dihydroquinazolin-6-yl)-N-hydroxyacrylamide (5an, Compound 36)

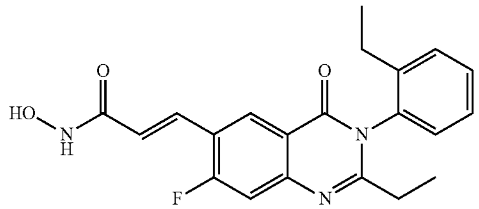 [SMILES: CCc1ccccc1-n1c(CC)nc2cc(F)c(/C=C/C(=O)NO)cc2c1=O]

The slurry solution of NaOH (0.3 g, 7.25 mmol) in $NH_2OH$ (27 mL) was added 4an (1.4 g, 3.63 mmol) at 0° C. and stirred at rt. for 1.5 h. The resulting solution was quenched with 1 N HCl (20 mL) until pH=7 and extracted with DCM (75 mL×2), H2O (50 mL). The organic layer was dried over MgSO4 and concentrated to give the crude. The crude was purified by flash column (¢3.5×8, MeOH/DCM=1/50-1/40) to give the product as orange oil. The oil was dissolved with EA (3 mL) and added Hex (10 mL) during sonication to precipitate the product as clear orang solid. (0.7 g, 51%). Rf=0.3 (MeOH/DCM=1:10); $^1$H NMR (400 MHz, DMSO-d6) 1.06 (t, 3H, J=7.6 Hz), 1.12 (t, 3H, J=7.3 Hz), 2.13-2.40 (m, 4H), 6.70 (d, 1H, J=15.9 Hz), 7.37-7.49 (m, 2H), 7.50 (d, 2H, J=2.7 Hz), 7.57 (s, 1H), 7.61 (d, 1H, J=5.1 Hz), 8.37 (d, 1H, J=8.2 Hz), 9.20 (s, 1H), 10.87 (s, 1H); ESIMS(+) m/z 382 $[M+H]^+$; HPLC 98%

Example 59: 2-ethyl-7-fluoro-3-(4-fluorophenyl)-6-iodoquinazolin-4(3H)-one (3ak)

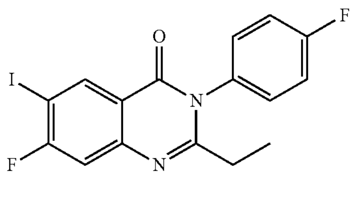 [SMILES: CCc1nc2cc(F)c(I)cc2c(=O)n1-c1ccc(F)cc1]

The solution of 2a (5.0 g, 17.79 mmol) in pyridine (23 mL) was added propionic anhydride (3.4 mL, 26.69 mmol), $P(OPh)_3$ (6.0 mL, 23.13 mmol) and stirred at rt. for 10 min. The resulting solution was irritated by MW 250 W 20 min. The reaction mixture was added 4-fluoroaniline (2.2 mL, 23.13 mmol) and irritated by MW 250 W 20 min. The resulting solution was quenched with 3 N HCl (65 mL) until pH=2 and extracted with DCM (75 mL×2). The organic layer was dried over $MgSO_4$ and concentrated to give the crude as brown oil. The crude was purified by flash column (¢4.5×9, EA/HEX=1/9) to give the slurry solution. The residue was washed with Hex (10 mL) to give the product as clear orange solid. (3.8 g, 52%). Rf=0.63 (EA/Hex=1:2);

2-ethyl-7-fluoro-6-iodo-3-(p-tolyl)quinazolin-4(3H)-one (3al)

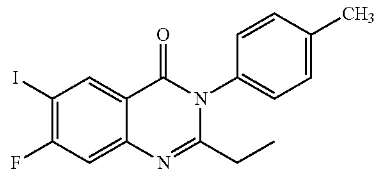 [SMILES: CCc1nc2cc(F)c(I)cc2c(=O)n1-c1ccc(C)cc1]

The solution of 2a (5.0 g, 17.79 mmol) in pyridine (23 mL) was added propionic anhydride (3.4 mL, 26.69 mmol), $P(OPh)_3$ (6.0 mL, 23.13 mmol) and stirred at rt. for 10 min. The resulting solution was irritated by MW 250 W 20 min. The reaction mixture was added 4-methylaniline hydrochloride (3.3 g, 23.13 mmol) and irritated by MW 250 W 20 min. The resulting solution was quenched with 3 N HCl (68 mL) until pH=2 and extracted with DCM (75 mL×2). The organic layer was dried over $MgSO_4$ and concentrated to give the crude as orange oil. The crude was purified by flash column (¢4.5×9, EA/HEX=1/9-1/8-EA/DCM/Hex=1/7/7) to give the slurry solution. The slurry solution was filtered to give the product as white solid. (2.8 g, 39%). Rf=0.55 (EA/Hex=1:2);

2-ethyl-7-fluoro-6-iodo-3-(4-methoxyphenyl)quinazolin-4(3H)-one (3am)

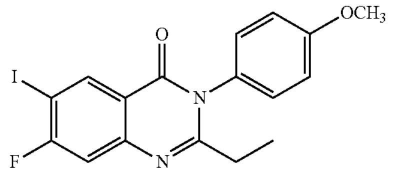 [SMILES: CCc1nc2cc(F)c(I)cc2c(=O)n1-c1ccc(OC)cc1]

The solution of 2a (5.0 g, 17.79 mmol) in pyridine (22 mL) was added propionic anhydride (3.4 mL, 26.69 mmol), $P(OPh)_3$ (6.0 mL, 23.13 mmol) and stirred at rt. for 10 min. The resulting solution was irritated by MW 250 W 20 min. The reaction mixture was added 4-methoxyaniline (2.9 g, 23.13 mmol) and irritated by MW 250 W 20 min. The resulting solution was quenched with 3 N HCl (65 mL) until pH=2 and extracted with DCM (75 mL×2). The organic layer was dried over $MgSO_4$ and concentrated to give the crude as black oil. The crude was purified by flash column (¢4.5×9, EA/HEX=1/9-DCM/Hex=1/1) to give the product as yellow solid. The solid was washed with Hex (50 mL) to give the product as white solid. (3.3 g, 43%). Rf=0.38 (EA/Hex=1:2);

2-ethyl-7-fluoro-3-(2-fluoro-6-methylphenyl)-6-iodoquinazolin-4(3H)-one (3an)

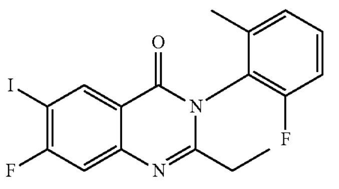 [SMILES: CCc1nc2cc(F)c(I)cc2c(=O)n1-c1c(C)cccc1F]

The solution of 2a (5.0 g, 17.79 mmol) in pyridine (22 mL) was added propionic anhydride (3.4 mL, 26.69 mmol), $P(OPh)_3$ (6.0 mL, 23.13 mmol) and stirred at rt. for 10 min. The resulting solution was irritated by MW 250 W 20 min. The reaction mixture was added 2-fluoro-6-methyl (2.9 g, 23.13 mmol) and irritated by MW 250 W 20 min. The resulting solution was quenched with 3 N HCl (68 mL) until pH=2 and extracted with DCM (75 mL×2). The organic layer was dried over $MgSO_4$ and concentrated to give the crude as brown oil. The crude was purified by flash column (¢4.5×9, EA/HEX=1/9-1/8) to give the product as yellow oil. The oil was put overnight to provide the beige crystal. The mixture solution was added Hex (15 mL) and put at 0° C. for 2 h to precipitate the product as white solid. (3.0 g, 40%). Rf=0.55 (EA/Hex=1:2);

2-ethyl-3-(4-ethylphenyl)-7-fluoro-6-iodoquinazolin-4(3H)-one (3ao)

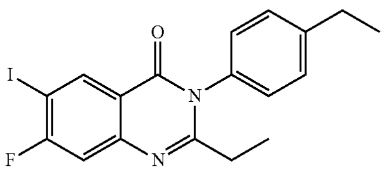 [SMILES: CCc1ccc(-n2c(CC)nc3cc(F)c(I)cc3c2=O)cc1]

The solution of 2a (5.0 g, 17.79 mmol) in pyridine (23 mL) was added propionic anhydride (3.4 mL, 26.69 mmol), $P(OPh)_3$ (6.0 mL, 23.13 mmol) and stirred at rt. for 10 min. The resulting solution was irritated by MW 250 W 20 min. The reaction mixture was added 4-ethylaniline (2.9 mL, 23.13 mmol) and irritated by MW 250 W 20 min. The resulting solution was quenched with 3 N HCl (68 mL) until pH=2 and extracted with DCM (75 mL×2). The organic layer was dried over $MgSO_4$ and concentrated to give the crude as brown slurry solution. The resulting residue was added EA (1 mL), Hex (3 mL), ether (5 mL) to precipitate the product as beige solid. (3.5 g, 47%). Rf=0.68 (EA/Hex=1:2);

3-(4-chlorophenyl)-2-ethyl-7-fluoro-6-iodoquinazolin-4(3H)-one (3ap)

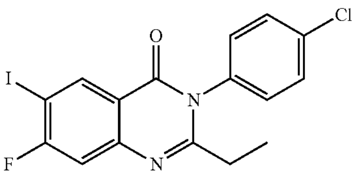 [SMILES: CCc1nc2cc(F)c(I)cc2c(=O)n1-c1ccc(Cl)cc1]

The solution of 2a (5.0 g, 17.79 mmol) in pyridine (23 mL) was added propionic anhydride (3.4 mL, 26.69 mmol), $P(OPh)_3$ (6.0 mL, 23.13 mmol) and stirred at rt. for 10 min. The resulting solution was irritated by MW 250 W 20 min. The reaction mixture was added 2-ethylaniline (3 mL, 23.13 mmol) and irritated by MW 250 W 20 min. The resulting solution was quenched with 3 N HCl (68 mL) until pH=2 and extracted with DCM (75 mL×2). The organic layer was dried over $MgSO_4$ and concentrated to give the crude as yellow oil. The crude was purified by flash column (¢4.5×9, EA/HEX=1/9-1/8) to give the product as yellow oil. The oil was added Hex (5 mL) and sonicated to give the product as white solid. (3.2 g, 42%). Rf=0.55 (EA/Hex=1:2);

(E)-ethyl 3-(2-ethyl-7-fluoro-3-(4-fluorophenyl)-4-oxo-3,4-dihydroquinazolin-6-yl)acrylate (4ak)

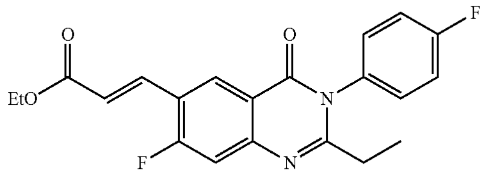 [SMILES: CCOC(=O)/C=C/c1cc2c(=O)n(-c3ccc(F)cc3)c(CC)nc2cc1F]

The reaction mixture of 3ak (3.8 g, 9.22 mmol), $Pd(OAc)_2$ (0.1 g, 0.46 mmol), $PPh_3$ (0.2 g, 0.92 mmol), NaOAc (1.1 g, 13.83 mmol), ethyl acrylate (1.1 mL, 10.14 mmol) in DMA (18 mL) was irritated by MW 250 W 25 min. The resulting solution was filtered and the filtrate was extracted with DCM (75 mL×2) and saturated NaCl (sat. 75 mL). The organic layer was dried over $MgSO_4$, filtered and concentrated in vacuo to give the crude as black oil. The crude was purified by flash column (¢4×8, EA/HEX=1/8-1/7) to give the brown liquid. The residue was added Hex (15 mL) and sonicated to precipitated the product as beige solid. (2.0 g, 56%). Rf=0.4 (EA/Hex=1:2);

(E)-ethyl 3-(2-ethyl-7-fluoro-4-oxo-3-(p-tolyl)-3,4-dihydroquinazolin-6-yl)acrylate (4al)

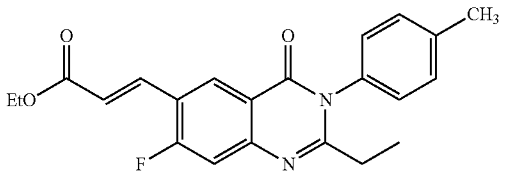 [SMILES: CCOC(=O)/C=C/c1cc2c(=O)n(-c3ccc(C)cc3)c(CC)nc2cc1F]

The reaction mixture of 3al (2.8 g, 6.86 mmol), $Pd(OAc)_2$ (76 mg, 0.34 mmol), $PPh_3$ (0.2 g, 0.69 mmol), NaOAc (0.8 g, 10.29 mmol), ethyl acrylate (0.8 mL, 7.55 mmol) in DMA (12 mL) was irritated by MW 250 W 25 min. The resulting solution was filtered and the filtrate was extracted with DCM (75 mL×2) and saturated NaCl (sat. 75 mL). The organic layer was dried over $MgSO_4$, filtered and concentrated in vacuo to give the crude as black oil. The crude was purified by flash column (¢4×9, EA/HEX=1/9-1/7) to give the product as white-gray solid. (1.6 g, 61%). Rf=0.48 (EA/Hex=1:2);

(E)-ethyl 3-(2-ethyl-7-fluoro-3-(4-methoxyphenyl)-4-oxo-3,4-dihydroquinazolin-6-yl)acrylate (4am)

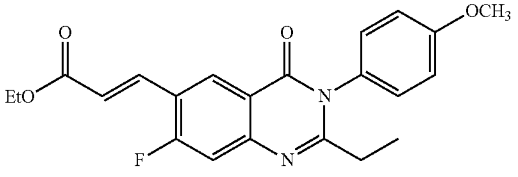 [SMILES: CCOC(=O)/C=C/c1cc2c(=O)n(-c3ccc(OC)cc3)c(CC)nc2cc1F]

The reaction mixture of 3am (3.2 g, 7.54 mmol), $Pd(OAc)_2$ (85 mg, 0.38 mmol), $PPh_3$ (0.2 g, 0.75 mmol), NaOAc (0.9 g, 11.32 mmol), ethyl acrylate (0.9 mL, 8.30 mmol) in DMA (15 mL) was irritated by MW 250 W 25 min. The resulting solution was filtered and the filtrate was extracted with DCM (75 mL×2) and saturated NaCl (sat. 75 mL). The organic layer was dried over $MgSO_4$, filtered and concentrated in vacuo to give the crude as black oil. The crude was purified by flash column (¢3.5×9, EA/HEX=1/10-DCM/Hex=2/1) to give the product as yellow solid. The solid was washed with ether (5 mL) to give the product as yellow solid. (1.4 g, 47%). Rf=0.33 (EA/Hex=1:2);

(E)-ethyl 3-(2-ethyl-7-fluoro-3-(2-fluoro-6-methylphenyl)-4-oxo-3,4-dihydroquinazolin-6-yl)acrylate (4an)

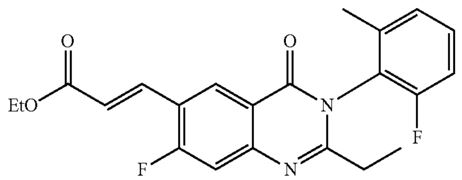

The reaction mixture of 3an (3.0 g, 7.04 mmol), $Pd(OAc)_2$ (79 mg, 0.35 mmol), $PPh_3$ (0.2 g, 0.70 mmol), NaOAc (0.9 g, 10.56 mmol), ethyl acrylate (0.8 mL, 7.74 mmol) in DMA (14 mL) was irritated by MW 250 W 25 min. After cooling to rt., the resulting solution was diluted with DCM (30 mL) and filtered. The filtrate was extracted with DCM (70 mL×2) and saturated NaCl (sat. 70 mL). The organic layer was dried over $MgSO_4$, filtered and concentrated in vacuo to give the crude as black oil. The crude was purified by flash column (¢3.5×8, EA/HEX=1/8-1/7) to give the product as brown oil. The oil was added Hex (3 mL) and sonicated for 30 sec to precipitate the product as orange solid. (1.4 g, 50%). Rf=0.5 (EA/Hex=1:2);

(E)-ethyl 3-(2-ethyl-3-(4-ethylphenyl)-7-fluoro-4-oxo-3,4-dihydroquinazolin-6-yl)acrylate (4ao)

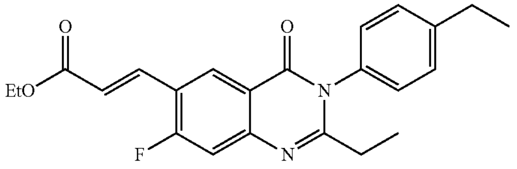 [SMILES: CCOC(=O)/C=C/c1cc2c(=O)n(-c3ccc(CC)cc3)c(CC)nc2cc1F]

The reaction mixture of 3ao (3.1 g, 7.34 mmol), $Pd(OAc)_2$ (83 mg, 0.37 mmol), $PPh_3$ (0.2 g, 0.73 mmol), NaOAc (0.9 g, 11.01 mmol), ethyl acrylate (0.9 mL, 8.08 mmol) in DMA (15 mL) was irritated by MW 250 W 25 min. After cooling to rt., the resulting solution was filtered and the filtrate was extracted with DCM (75 mL×2) and saturated NaCl (sat. 75 mL). The organic layer was dried over $MgSO_4$, filtered and concentrated in vacuo to give the crude as black oil. The crude was purified by flash column (¢4×8, EA/HEX=1/8-1/7.5) to give the product as yellow slurry solution. The solution was added Hex (20 mL) to precipitate the product as yellow solid. (1.3 g, 45%). Rf=0.65 (EA/Hex=1:2);

(E)-ethyl 3-(3-(4-chlorophenyl)-2-ethyl-7-fluoro-4-oxo-3,4-dihydroquinazolin-6-yl)acrylate (4ap)

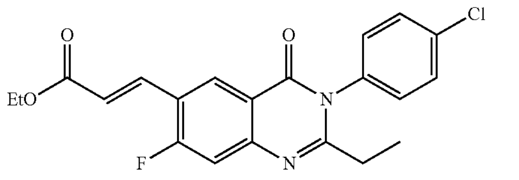

The reaction mixture of 3ap (3.2 g, 6.11 mmol), $Pd(OAc)_2$ (83 mg, 0.37 mmol), $PPh_3$ (0.2 g, 0.75 mmol), NaOAc (0.9 g, 11.21 mmol), ethyl acrylate (0.9 mL, 8.22 mmol) in DMA (15 mL) was irritated by MW 250 W 25 min. After cooling to rt., the resulting solution was filtered. The filtrate was extracted with DCM (75 mL×2) and saturated NaCl (sat. 75 mL). The organic layer was dried over $MgSO_4$, filtered and concentrated in vacuo to give the crude as black oil. The crude was purified by precipitation (EA/Hex=3/2 mL) to give the product as orange solid. (1.8 g, 59%). Rf=0.4 (EA/Hex=1:2);

Example 60: (E)-3-(2-ethyl-7-fluoro-3-(4-fluorophenyl)-4-oxo-3,4-dihydroquinazolin-6-yl)-N-hydroxyacrylamide (5ak, Compound 40)

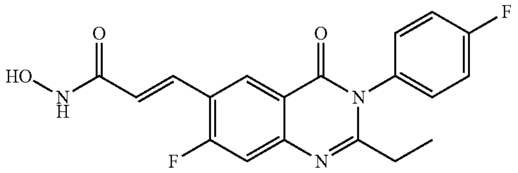 [SMILES: CCc1nc2cc(F)c(/C=C/C(=O)NO)cc2c(=O)n1-c1ccc(F)cc1]

The slurry solution of NaOH (0.4 g, 10.40 mmol) in $NH_2OH$ (39 mL) was added 4ak (2.0 g, 5.20 mmol) at 0° C. and stirred at rt. for 1.5 h. The resulting solution was quenched with 1 N HCl (27 mL) until pH=7 and extracted with CHCl3 (75 mL), NaCl (sat. 75 mL). The slurry solution was filtered and the organic layer was separated. The water layer was extracted with CHCl3 (75 mL). The organic layer was dried over MgSO4 and concentrated to give the crude. The crude was purified by flash column (¢4×10, MeOH/DCM=1/40-1/30) to give the product as white solid. The solid was dissolved with MeOH (1 mL), DCM (5 mL) and concentrated until the solvent remained 1.5 mL. The residue was added EA (1 mL) and sonicated to precipitate the product (clear to slurry). The slurry solution was added Hex (10 mL) and filtered to give the product as white solid. (0.5 g, 23%). Rf=0.33 (MeOH/DCM=1:10); $^1$H NMR (400 MHz, DMSO-d6) δ 1.12 (t, 3H, J=7.3 Hz), 2.34 (q, 2H, J=7.3 Hz), 6.69 (d, 1H, J=16.0 Hz), 7.42 (t, 2H, J=8.8 Hz), 7.52-7.61 (m, 4H), 8.34 (d, 1H, J=8.2 Hz), 9.18 (s, 1H), 10.87 (s, 1H); ESIMS(+) m/z 372 [M+H]+; HPLC 99%.

Example 61: (E)-3-(2-ethyl-7-fluoro-4-oxo-3-(p-tolyl)-3,4-dihydroquinazolin-6-yl)-N-hydroxyacrylamide (5al, Compound 39)

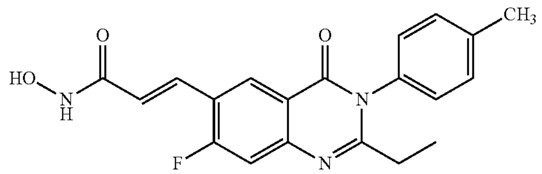 [SMILES: CCc1nc2cc(F)c(/C=C/C(=O)NO)cc2c(=O)n1-c1ccc(C)cc1]

The slurry solution of NaOH (0.3 g, 8.30 mmol) in $NH_2OH$ (31 mL) was added 4al (1.6 g, 4.15 mmol) at 0° C. and stirred at rt. for 1 h. The resulting solution was quenched with 1 N HCl (20 mL) until pH=7 and extracted with DCM (75 mL), NaCl (sat. 75 mL). The slurry solution was filtered and the organic layer was separated. The water layer was extracted with DCM (75 mL). The organic layer was dried over MgSO4 and concentrated to give the crude as yellow oil. The crude was purified by flash column (¢3.5×9, MeOH/DCM=1/40-1/30) to give the product as clear orange oil. The oil was diluted with MeOH (1 mL), DCM (2 mL) and added EA (2 mL) during sonication to precipitate the product (clear to slurry). The slurry solution was added Hex (5 mL) to precipitate the product as clear orange-white solid. (0.5 g, 31%). Rf=0.25 (MeOH/DCM=1:10); $^1$H NMR (400 MHz, DMSO-d6) δ 1.11 (t, 3H, J=7.3 Hz), 2.34 (q, 2H, J=7.3 Hz), 2.40 (s, 3H), 6.69 (d, 1H, J=15.9 Hz), 7.30-7.38 (m, 4H), 7.54 (d, 1H, J=11.9 Hz), 7.58 (d, 1H, J=16.0 Hz), 8.33 (d, 1H, J=8.2 Hz), 9.18 (s, 1H), 10.86 (s, 1H); ESIMS(+) m/z 368 [M+H]+; HPLC 98%.

Example 61: (E)-3-(2-ethyl-7-fluoro-3-(4-methoxyphenyl)-4-oxo-3,4-dihydroquinazolin-6-yl)-N-hydroxyacrylamide (5am, Compound 38)

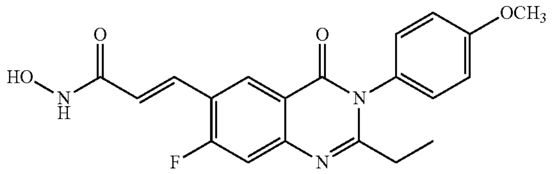 [SMILES: CCc1nc2cc(F)c(/C=C/C(=O)NO)cc2c(=O)n1-c1ccc(OC)cc1]

The slurry solution of NaOH (0.3 g, 7.06 mmol) in $NH_2OH$ (26 mL) was added 4am (1.4 g, 3.53 mmol) at 0° C. and stirred at rt. for 1 h. The resulting solution was quenched with 1 N HCl (20 mL) until pH=7 and extracted with CHCl3 (75 mL), NaCl (sat. 75 mL). The slurry solution was filtered and the organic layer was separated. The water layer was extracted with CHCl3 (75 mL). The organic layer was dried over MgSO4 and concentrated to give the crude. The crude was purified by flash column (¢4×8, MeOH/DCM=1/40-1/35) to give the product as clear orange oil. The oil was diluted with MeOH (1 mL), DCM (5 mL) and concentrated until the solvent remained 1 mL. The residue was added EA (2 mL) during sonication to precipitate the product (clear to slurry). The slurry solution was added Hex (10 mL) to precipitate the product as clear orang solid. (0.5 g, 38%). Rf=0.3 (MeOH/DCM=1:10); $^1$H NMR (400 MHz, DMSO-d6) δ 1.10 (t, 3H, J=7.3 Hz), 2.35 (q, 2H, J=7.3 Hz), 3.82 (s, 3H), 6.68 (d, 1H, J=15.9 Hz), 7.09 (d, 2H, J=8.9 Hz), 7.34 (d, 2H, J=8.8 Hz), 7.53 (d, 1H, J=11.8 Hz), 7.58 (d, 1H, J=15.9 Hz), 8.33 (d, 1H, J=8.2 Hz), 9.22 (s, 1H), 10.90 (s, 1H); ESIMS(+) m/z 384 [M+H]+; HPLC 98%.

Example 62: (E)-3-(2-ethyl-7-fluoro-3-(2-fluoro-6-methylphenyl)-4-oxo-3,4-dihydroquinazolin-6-yl)-N-hydroxyacrylamide (5an, Compound 37)

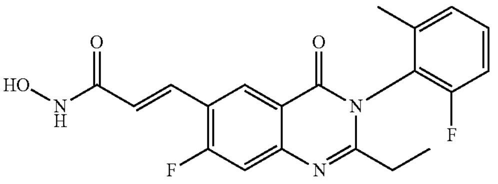 [SMILES: CCc1nc2cc(F)c(/C=C/C(=O)NO)cc2c(=O)n1-c1c(C)cccc1F]

The slurry solution of NaOH (0.3 g, 7.03 mmol) in $NH_2OH$ (26 mL) was added 4an (1.4 g, 3.51 mmol) at 0° C. and stirred at rt. for 30 mins. The resulting solution was quenched with 1 N HCl (18 mL) until pH=7 and extracted with CHCl3 (75 mL), DCM (75 mL), NaCl (sat. 75 mL). The organic layer was dried over MgSO4 and concentrated to give the crude as orange oil. The crude was purified by flash column (¢3.5×9, MeOH/DCM=1/40-1/35) to give the product as clear orange-white solid. The solid was dissolved with MeOH (1 mL), DCM (3 mL) and concentrated until the solvent remained 1 mL. The residue was added EA (1 mL) during sonication to precipitate the product (clear to slurry). The slurry solution was added Hex (20 mL) to precipitate the product as clear orang-white solid. (1.0 g, 76%). Rf=0.33 (MeOH/DCM=1:10); $^1$H NMR (400 MHz, DMSO-d6) δ 1.14 (t, 3H, J=7.3 Hz), 2.08 (s, 3H), 2.26-2.38 (m, 2 H), 6.70 (d, 1H, J=16.0 Hz), 7.32-7.36 (m, 2H), 7.50-7.62 (m, 3H), 8.38 (d, 1H, J=8.1 Hz), 9.23 (s, 1H), 10.93 (s, 1H); ESIMS (+) m/z 386 $[M+H]^+$; HPLC 99%.

Example 63: (E)-3-(2-ethyl-3-(4-ethylphenyl)-7-fluoro-4-oxo-3,4-dihydroquinazolin-6-yl)-N-hydroxyacrylamide (5ao, Compound 42)

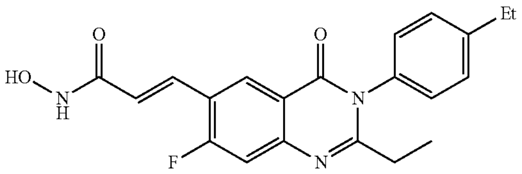 [SMILES: CCc1nc2cc(F)c(/C=C/C(=O)NO)cc2c(=O)n1-c1ccc(Cl)cc1]

The slurry solution of NaOH (0.3 g, 6.59 mmol) in $NH_2OH$ (25 mL) was added 4ao (1.3 g, 3.30 mmol) at 0° C. and stirred at rt. for 2.5 h. The resulting solution was quenched with 1 N HCl (20 mL) until pH=7 and extracted with DCM (75 mL), H2O (50 mL). The slurry solution was filtered and the water layer was extracted with DCM (75 mL). The organic layer was dried over MgSO4 and concentrated to give the crude as orange oil. The crude was purified by flash column (¢4×8, MeOH/DCM=1/50-1/30) to give the product as orange solid. The solid was dissolved with MeOH (1 mL), DCM (5 mL) and concentrated until the solvent remained 1 mL. The residue was added EA (2 mL) and sonicated. The slurry solution was added Hex (10 mL) to precipitate the product as beige solid. (0.4 g, 30%). Rf=0.3 (MeOH/DCM=1:10); $^1$H NMR (400 MHz, DMSO-d6) δ 1.11 (t, 3H, J=7.3 Hz), 1.25 (t, 3H, J=7.6 Hz), 2.33 (q, 2H, J=7.3 Hz), 2.70 (q, 2H, J=7.6 Hz), 6.69 (d, 1H, J=16.0 Hz), 7.40 (dd, 4H, J=18.5 Hz, 8.32 Hz), 7.55 (d, 1H, J=12.3 Hz), 7.58 (d, 1H, J=16.6 Hz), 8.33 (d, 1H, J=8.2 Hz), 9.19 (s, 1H), 10.87 (s, 1H); ESIMS(+) m/z 382 $[M+H]^+$; HPLC 98%.

Example 64: (E)-3-(3-(4-chlorophenyl)-2-ethyl-7-fluoro-4-oxo-3,4-dihydroquinazolin-6-yl)-N-hydroxyacrylamide (5ap, Compound 41)

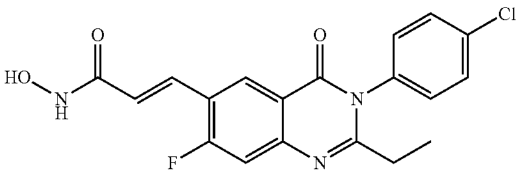

The slurry solution of NaOH (0.4 g, 8.88 mmol) in $NH_2OH$ (33 mL) was added 4ap (1.8 g, 4.44 mmol) at 0° C. and stirred at rt. for 3.5 h. The resulting solution was quenched with 1 N HCl (20 mL) until pH=7 and extracted with CHCl3 (75 mL), NaCl (sat. 75 mL). The slurry solution was filtered and the organic layer was separated. The water layer was extracted with CHCl3 (75 mL). The organic layer was dried over MgSO4 and concentrated to give the crude as orange oil. The crude was purified by flash column (¢4×9, MeOH/DCM=1/40-1/35) to give the product as clear orange oil. The oil was diluted with DCM (5 mL) and concentrated until the solvent remained 2 mL. The residue was added EA (1 mL) during sonication to precipitate the product (clear to slurry). The slurry solution was added Hex (10 mL) to precipitate the product as clear orang solid. (0.2 g, 9%). Rf=0.35 (MeOH/DCM=1:10); $^1$H NMR (400 MHz, DMSO-d6) δ 1.12 (t, 3H, J=7.3 Hz), 2.34 (q, 2H, J=7.3 Hz), 6.69 (d, 1H, J=15.9 Hz), 7.51-7.66 (m, 6H), 8.34 (d, 1H, J=8.2 Hz), 9.18 (s, 1H), 10.86 (s, 1H); ESIMS(+) m/z 386 $[M+H]^+$; HPLC 92%.

Example 65: 3-(4-(dimethylamino)phenyl)-2-ethyl-7-fluoro-6-iodoquinazolin-4(3H)-one (3aq)

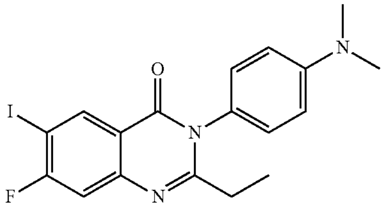 [SMILES: CCc1nc2cc(F)c(I)cc2c(=O)n1-c1ccc(N(C)C)cc1]

The solution of 2a (5.0 g, 17.79 mmol) in pyridine (23 mL) was added propionic anhydride (3.4 mL, 26.69 mmol), $P(OPh)_3$ (6.0 mL, 23.13 mmol) and stirred at rt. for 10 min. The resulting solution was irritated by MW 250 W 20 min. The reaction mixture was added 4-n,n-dimethylaminoaniline (2.9 mL, 23.13 mmol) and irritated by MW 250 W 20 min. The resulting solution was quenched with 3 N HCl (68 mL) until pH=2 and extracted with DCM (75 mL×2). The organic layer was dried over $MgSO_4$ and concentrated to give the crude as deep blue slurry solution. The resulting residue was added EA (1 mL), Hex (3 mL), ether (5 mL) to precipitate the product as deep blue solid. (4.0 g, 51%). Rf=0.38 (EA/Hex=1:2);

(E)-ethyl 3-(3-(4-(dimethylamino)phenyl)-2-ethyl-7-fluoro-4-oxo-3,4-dihydroquinazolin-6-yl)acrylate (4aq)

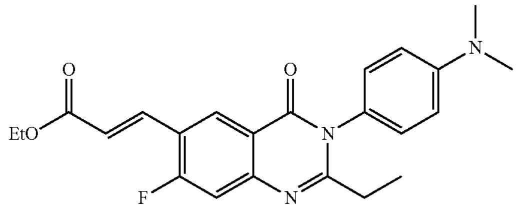 [SMILES: CCOC(=O)/C=C/c1cc2c(=O)n(-c3ccc(N(C)C)cc3)c(CC)nc2cc1F]

The reaction mixture of 3aq (4.0 g, 9.15 mmol), $Pd(OAc)_2$ (0.1 g, 0.46 mmol), $PPh_3$ (0.2 g, 0.91 mmol), NaOAc (1.1 g, 13.72 mmol), ethyl acrylate (1.0 mL, 10.06 mmol) in DMA (18 mL) was irritated by MW 250 W 25 min. After cooling to rt., the resulting solution was filtered and the filtrate was extracted with DCM (75 mL×2) and saturated NaCl (sat. 75 mL). The organic layer was dried over $MgSO_4$, filtered and concentrated in vacuo to give the crude as black solid. The solid was washed with MeOH (30 mL) to give the product as brown green solid. (2.5 g, 66%). Rf=0.35 (EA/Hex=1:2);

Example 66: (E)-3-(3-(4-(dimethylamino)phenyl)-2-ethyl-7-fluoro-4-oxo-3,4-dihydroquinazolin-6-yl)-N-hydroxyacrylamide (5aq, Compound 43)

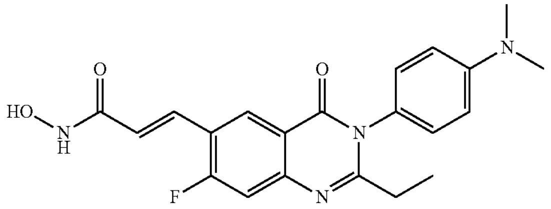 [SMILES: CCc1nc2cc(F)c(/C=C/C(=O)NO)cc2c(=O)n1-c1ccc(N(C)C)cc1]

The slurry solution of NaOH (0.5 g, 12.21 mmol) in $NH_2OH$ (46 mL) was added 4aq (2.5 g, 6.11 mmol) at 0° C. and stirred at rt. for 5 h. The resulting solution was quenched with 2 N HCl (25 mL) until pH=7 and extracted with [M (75 mL+MeOH 5 mL)×2), H2O (75 mL). The slurry solution was filtered and the water layer was extracted with DCM (75 mL). The organic layer was dried over MgSO4 and concentrated to give the crude as orange oil. The crude was purified by flash column (¢4×8, MeOH/DCM=1/50-1/30) to give the product as orange solid. The solid was dissolved with MeOH (1 mL), DCM (5 mL) and concentrated until the solvent remained 1 mL. The residue was added EA (2 mL) and sonicated. The slurry solution was added Hex (10 mL) to precipitate the product as beige solid. (0.4 g, 30%). Rf=0.3 (MeOH/DCM=1:10); $^1H$ NMR (400 MHz, DMSO-d6) δ 1.09 (t, 3H, J=7.3 Hz), 2.38 (q, 2H, J=7.3 Hz), 2.97 (s, 6H), 6.69 (d, 1H, J=15.9 Hz), 6.82 (d, 2H, J=9.0 Hz), 7.17 (d, 2H, J=8.9 Hz), 7.52 (d, 1H, J=11.8 Hz), 7.58 (d, 1H, J=15.9 Hz), 8.33 (d, 1H, J=8.2 Hz), 9.19 (s, 1H), 10.86 (s, 1H); ESIMS (+) m/z 397 $[M+H]^+$; HPLC 98%.

Example 67: 7-Fluoro-6-iodo-2-methyl-3-(o-tolyl)quinazolin-4(3H)-one (42e)

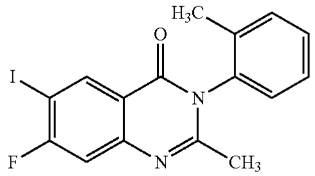 [SMILES: Cc1ccccc1-n1c(C)nc2cc(F)c(I)cc2c1=O]

To a mixture of 2-amino-4-fluoro-5-iodobenzoic acid (3.00 g, 10.7 mmol) in pyridine (10 mL) was added triphenyl phosphite (3.5 mL, 12.8 mmol) and acetyl chloride (1.2 mL, 16.0 mmol) and the mixture was stirred at room temperature for 15 min. To the mixture was then added 2-methylaniline hydrochloride (2.35 g, 16.0 mmol) and the mixture was irradiated by microwave (200 W) with refluxing for 10 min. The mixture was partitioned between EtOAc (140 mL) and water (100 mL). The water layer was extracted with EtOAc (100 mL×2) and the combined organic layer was dried over $MgSO_4$, and evaporated to precipitate out. The precipitate was collected and dried in vacuo to give 42e (3.17 g, 75%) as an off-white solid. Rf=0.46 (EtOAc/Hexane=1/2); ESIMS (−) m/z 393.4.

Example 68: (E)-3-(7-Fluoro-2-methyl-4-oxo-3-(o-tolyl)-3,4-dihydroquinazolin-6-yl)acrylic acid

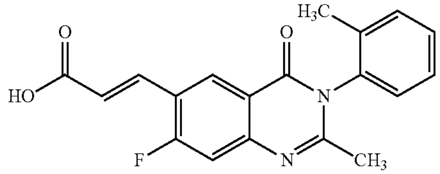 [SMILES: Cc1ccccc1-n1c(C)nc2cc(F)c(/C=C/C(=O)O)cc2c1=O]

To a mixture of 42e (1.60 g, 4.06 mmol), $Pd(OAc)_2$ (36 mg, 0.162 mmol), $[(t-Bu)_3PH]BF_4$ (94 mg, 0.325 mmol), and $Cs_2CO_3$ (1.32 g, 4.04 mmol) in DMF (20 mL) was added acrylic acid (0.28 mL, 4.06 mmol). The reaction mixture was followed general procedure A to give (E)-3-(7-Fluoro-2-methyl-4-oxo-3-(o-tolyl)-3,4-dihydroquinazolin-6-yl)acrylic acid crude (928 mg, 67%) as a red solid. ESIMS(−) m/z 337.2 $[M-H]^-$.

Example 69: (E)-3-(7-Fluoro-2-methyl-4-oxo-3-(o-tolyl)-3,4-dihydroquinazolin-6-yl)-N-hydroxyacrylamide (Compound 44, 43e)

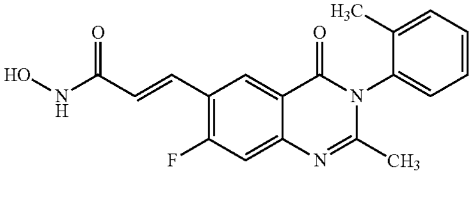 [SMILES: Cc1ccccc1-n1c(C)nc2cc(F)c(/C=C/C(=O)NO)cc2c1=O]

To a mixture of (E)-3-(7-Fluoro-2-methyl-4-oxo-3-(o-tolyl)-3,4-dihydroquinazolin-6-yl)acrylic acid (650 mg, 1.92 mmol), EDCI (552 mg, 2.88 mmol), and HOBt (259 mg, 1.92 mmol) in DMF (10 mL) was stirred at room temperature for 30 min. To the mixture was then added $NH_2OTHP$ (252 mg, 2.11 mmol) and the mixture was stirred at room temperature for additional 1.5 h. The mixture was poured into water (60 mL) to precipitate out. The precipitate was collected by filtration and purified by column chromatography (silica gel: #2.0×11 cm; eluted by gradient MeOH/$CH_2Cl_2$=0/100 to 1/99). The desired fraction was collected, evaporated, and dried in vacuo to give O-THP compound (542 mg, 65%) as a red solid. To a solution of O-THP compound (542 mg, 1.24 mmol) in MeOH (10 mL) was added TFA (10 mL, 129 mmol). The reaction mixture was stirred at 55° C. for 18 h. The solvent was evaporated and the residue was partitioned between EtOAc (30 mL) and water (30 mL). The water layer was extracted with EtOAc (30 mL×3). The combined organic layer was dried over $MgSO_4$, evaporated, and purified by column chromatography (silica gel: ϕ2.0×11 cm; eluted by gradient MeOH/$CH_2Cl_2$=1/99 to 3/97). The desired fraction was collected, evaporated, and dried in vacuo to give COMPOUND 44 (192 mg, 44%) as a pale yellow solid. $R_f$=0.33 (MeOH/$CH_2Cl_2$=1/9); $^1$H NMR (400 MHz, DMSO-$d_6$) δ 10.88 (s, 1H), 9.20 (s, 1H), 8.35 (d, J=8.2 Hz, 1H), 7.60-7.53 (m, 2H), 7.46-7.39 (m, 4H), 6.69 (d, J=16.0 Hz, 1H), 2.08 (s, 3H), 2.03 (s, 3H); $^{13}$C NMR (50 MHz, DMSO-$d_6$) δ; ESIMS(+) m/z 354.2 [M+H]+. HPLC 99.8%.

Example 70: HDAC6 Selective Inhibitors Showed Neuron Protection Effect in Paclitaxel-Induced Neuropathy Through Promoting Neurite Outgrowth To investigate the effect of HDAC6 inhibitors in neuron protection and neuron regeneration, the recovery of dorsal root ganglion (DRG) cells post-paclitaxel injury was tested. Dorsal root ganglion was extracted from 7 week-old female C57BL/6J mice and incubated with HDAC6 inhibitors (compounds COMPOUND 33, COMPOUND 34, or COMPOUND 2) at the concentrations of 0.1 M and 1 μM, or 100 ng/ml of BDNF, a neuronal growth factor (positive control), for 24 hours prior to a 24-hour incubation of 0.1 M paclitaxel. While paclitaxel-treated DRG neurons showed a 55% decrease in neurite outgrowth, pretreatment of HDAC6 inhibitors significantly rescued the neurite outgrowth due to paclitaxel-induced damage (FIG. 1). Moreover, the neuron-protective effect of HDAC6 inhibitors coincided with tubulin hyperacetylation (FIG. 2).

FIG. 1 shows that HDAC6 inhibitors exhibited significant neuroprotective effect against paclitaxel-induced damage in DRG neurite outgrowth model. The neurite was stained by βIII-tubulin.

Figure 2:
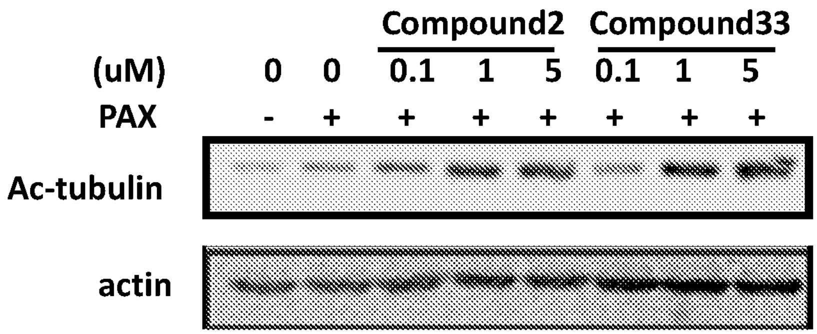
FIG. 2 shows a western blot of acetylated α-tubulin (Ac-α-tub) and actin protein in primary DRG cells after 48 hours of treatment of HDAC6 inhibitors.

FIG. 2 shows a western blot of acetylated α-tubulin (Ac-α-tub) and actin protein in primary DRG cells after 48 hours of treatment of HDAC6 inhibitors.

Example 71 the HDAC6 Selective Inhibitors Showed Protective Effect Against Cisplatin-Induced Neurite Degeneration Rat DRG cells were used to investigate the protective effect of HDAC6 inhibitors. DRG cells were treated with 0.5 mM of cisplatin with or without 0.3 M of COMPOUND 2 or ACY1215 for 48 hours. The neurite area and the number of blebs (cell apoptosis) per image were calculated and their ratio values among the tested groups were compared and shown in FIG. 3. The HDAC6 inhibitors treated DRG cells showed a significantly lesser degree of neurite degeneration ($p<0.05$).

Figure 3:
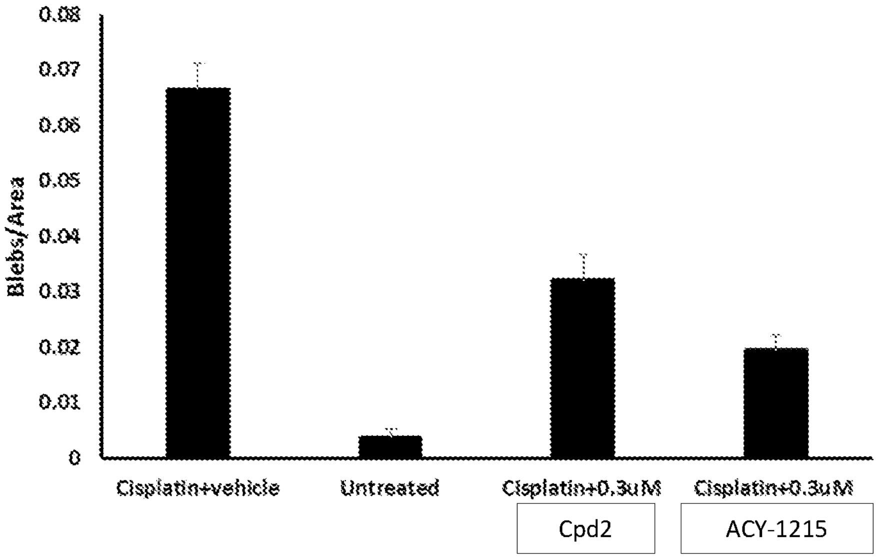
FIG. 3 shows the protective effect of HDAC6 inhibitors in ameliorating cisplatin induced neurite degeneration.

FIG. 3 shows the protective effect of HDAC6 inhibitors in ameliorating cisplatin induced neurite degeneration.

Example 72: Compound 2, not ACY1215, Reverses Cisplatin-Induced Neuropathy

To understand whether COMPOUND 2 exerts neuron protective activities in cisplatin-induced neuropathy, a paw-withdrawal murine model is deployed. The 50% paw withdrawal threshold (PWT) to a static mechanical stimulus was assessed using von Frey filament and up-and-down method following the procedure described by Chaplan (1994). Mechanical allodynia, a painful sensation caused by innocuous stimuli like light touch, was assessed by the manual von Frey test once per week (on day 7, 14, 21, 28, 36, and 42). The animals indicated sensation by pulling back its paw. The minimum force leading to withdrawal of the paw was regarded as the reflex threshold.

Balb/c mice weighing about 25±2 gram were given cisplatin intraperitoneally at the dose of 1.5 mg/kg for 5 consecutive days (cumulative dose of 7.5 mg/kg), followed by 5 days of recovery. The cisplatin administration cycle was repeated once more to reach a cumulative dose of 15 mg/kg to induce neuropathy. Test compounds, COMPOUND 2 and ACY1215, were orally administered once daily for 2 weeks (except for the weekends) from Day 16 to 29. Pregabalin, a drug known to provide transient pain relief, was administered at a dose of 15 mg/kg prior to each von Frey stimulus test to serve as the positive control.

Cisplatin-treated (Control) animals showed a significant decrease in the mean withdrawal force threshold on day 14 when comparing to the sham control animals ($p<0.001$). Pregabaline administered one hour prior to von Frey stimulus test increased withdrawal threshold compared to the cisplatin control animals which received no pregabalin pretreatment. COMPOUND 2 treatment significantly increased the mean withdrawal threshold when compared to the cisplatin control animals, indicating that COMPOUND 2 reversed the cisplatin-induced neuropathy condition in the animals. Additionally, COMPOUND 2 exerts distinct and superior activities than ACY-1215; indicating COMPOUND 2, as a highly selective HDAC6 inhibitor promotes the recovery of neuropathy more effectively than a less selective HDAC6 inhibitor.

Figure 4:
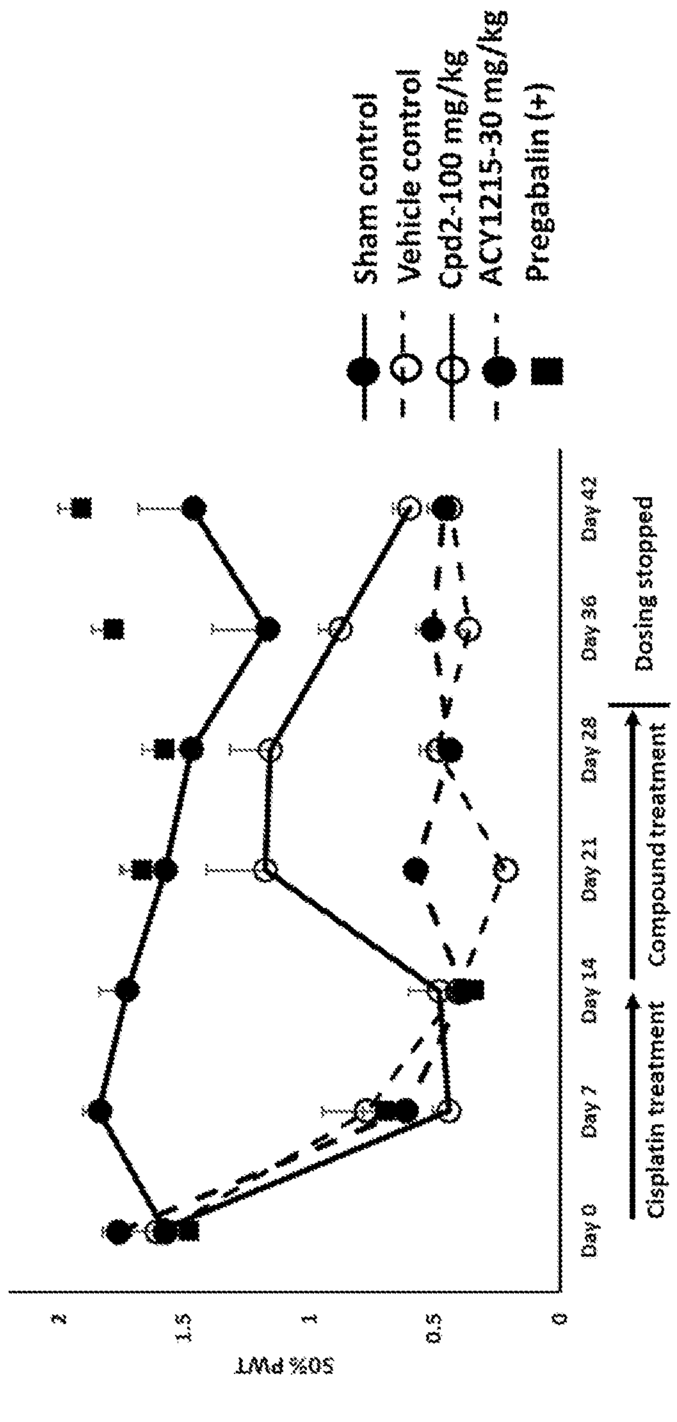
FIG. 4 shows the 50% paw withdrawal threshold (PWT) of the following groups: the Sham control (no cisplatin treatment, no testing drug treatment), the Vehicle control group (treated with cisplatin and drug vehicle only), COMPOUND 2 treatment group, ACY-1215 treatment group, and the pregabalin treatment group.

FIG. 4 shows the 50% paw withdrawal threshold (PWT) of the following groups: the Sham control (no cisplatin treatment, no testing drug treatment), the Vehicle control group (treated with cisplatin and drug vehicle only), COMPOUND 2 treatment group, ACY-1215 treatment group, and the pregabalin treatment group.

Example 73: Prevention and Treatment of Pulmonary Fibrosis

The activities of compounds COMPOUND 2 and COMPOUND 33 in preventing and/or treating pulmonary fibrosis were examined using a bleomycin-induced pulmonary fibrosis model, a model that involves deactivated bleomycin hydrolase, elevated oxidative stress, and increased inflammatory cytokines. In the prevention model, mice were administered bleomycin intratracheally an hour in prior to the first oral administration of 30 mg/kg testing compounds. The treatment continued for 21 consecutive days, and mice were sacrificed to examine histological changes of lung tissues were analyzed by H&E staining to evaluate the degree of lung fibrosis.

Figure 5:
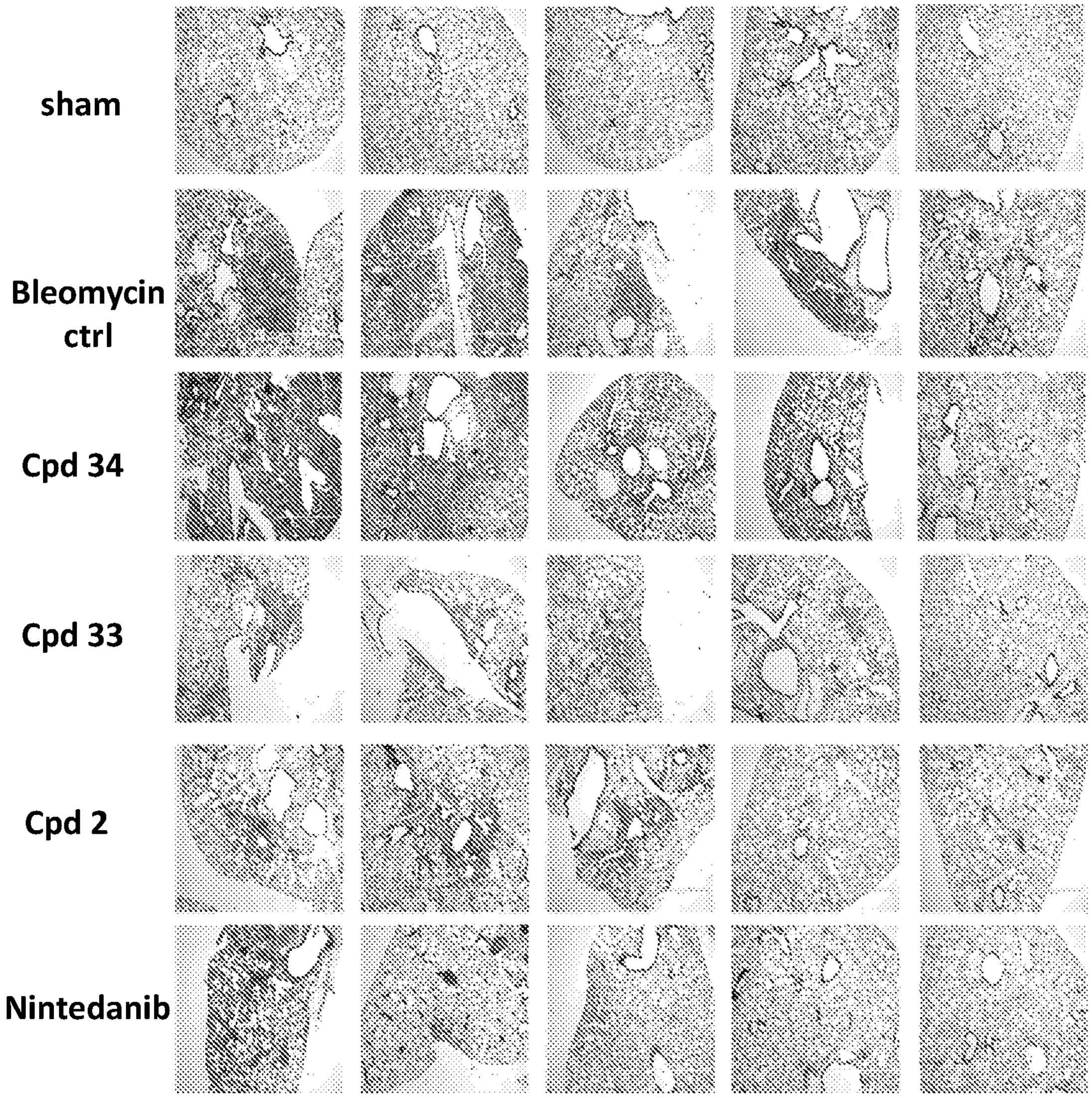
FIG. 5 depicts lung histology images for Compounds 34, 33, 2, and Nintedanib and the control.
Figure 6:
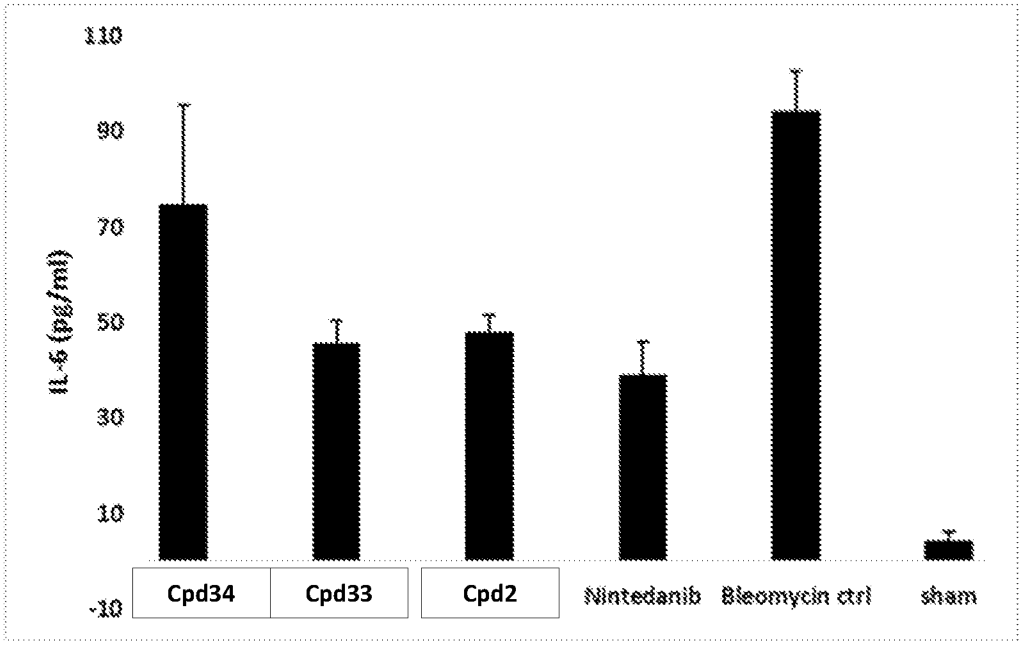
FIG. 6 depicts the IL-6 concentration for HDAC6 inhibitors.

COMPOUND 2 and COMPOUND 33 treatment markedly decreased the development of lung fibrosis in the animals (FIG. 5), as well as the presence of IL-6, a pro-inflammatory cytokines associated with pulmonary fibrosis, in the bronchoalveolar lavage fluid (BALF) (FIG. 6). In summary, COMPOUND 2 and COMPOUND 33 were shown to prevent pulmonary fibrosis after lung injury, as well as suppress the expression of IL-6 in the pulmonary tissue.

Additionally, the HDAC6 inhibitors, COMPOUND 2 and COMPOUND 33, were tested for their effect in aiding animal recovery from lung injury and pulmonary fibrosis post injury. The HDAC6 inhibitors demonstrate protective effect in pulmonary inflammatory response and pulmonary fibrosis.

FIG. 5 shows that COMPOUND 2 and COMPOUND 33 decreased lung fibrosis.

FIG. 6 shows that COMPOUND 2 and COMPOUND 33 suppressed IL-6 level in the BALF.

Example 74: Cytokine Profiles in Response to the Treatment of HDAC6 Inhibitors in Fibrotic Diseases The HDAC6 inhibitor compounds were tested in a commercially available platform, BioMAP, for the cytokine profiles in related to tissue injuries. The BioMAP Fibrosis panel included 3 systems stimulated to model TGFβ and TNFα driven myofibroblast differentiation during chronic inflammation and wound healing in different tissue settings. Fibrotic disease of the kidney associated with end-stage renal failure was captured in the REMyoF system consisting of a co-culture of renal proximal tubule epithelial cells and adult fibroblasts. Interstitial lung diseases, including pulmonary fibrotic diseases such as idiopathic pulmonary fibrosis (IPF), was modeled by co-culturing small airway epithelial cells and adult fibroblasts in the SAEMyoF system. Both co-culture systems modeled the paracrine interaction between myofibroblasts and the proximally located epithelial cells, while the impact on fibroblasts alone was interrogated using the monoculture MyoF system. A signature BioMAP profile that is reflective of the changes in protein biomarker readouts within an individual system was generated for each testing compounds. Biomarker readouts selected for therapeutic and biological relevance were predictive for disease outcomes or specific drug effects, and was validated using agents with known clinical efficacy. Each readout was measured quantitatively by immune-based methods that detect protein (e.g., ELISA).

BioMap readouts showed that COMPOUND 2 suppressed inflammation-related activities (decreased M-CSF, VCAM-1, sIL-6, MCP-1; increased I-TAC), myofibroblast activation-related activities (decreased αSMA, N-Cadherin), fibrosis-related matrix activities (decreased TIMP-1, MMP-1, Collagen I, Collagen III, MMP-9), and tissue remodeling/wound healing activities (decreased EGFR, tPA, uPA, bFGF, sVEGF). COMPOUND 33 also suppressed inflammation-related activities (decreased M-CSF, sIL-6, MCP-1; modulated IP-10, I-TAC), myofibroblast activation-related activities (decreased αSMA, E-Cadherin, N-Cadherin), fibrosis-related matrix activities (decreased Collagen III, MMP-9; increased Collagen IV; modulated MMP-1, Collagen I), and tissue remodeling/wound healing activities (decreased EGFR, tPA, uPA; modulated sVEGF). Moreover, when compared with nintedanib, a treatment approved for idiopathic pulmonary fibrosis and has shown beneficial effect in treating liver fibrosis (Wollin et al 2020) and kidney fibrosis (Liu et al 2017) in animal models. Both COMPOUND 2 and COMPOUND 33 showed marked activities in decreasing TNF-α, IL-1, IL-6, MMP-9, VEGF, and collagen I, the cytokines known to mechanistically contribute to the disease state of pulmonary fibrosis, renal fibrosis, and liver fibrosis.

Taken together, the HDAC6 inhibitors, taken COMPOUND 2 and COMPOUND 33 for example, demonstrate their potency in suppressing inflammatory response, and may be used to treat or ameliorate cytokine-induced tissue injury. The HDAC6 inhibitors may exert their efficacy in treating fibrotic diseases, such as idiopathic pulmonary fibrosis, virus-induced pulmonary fibrosis, renal fibrosis, and liver fibrosis through regulating levels of inflammatory cytokines.

Example 75: Table II Compounds Shows High Selectivity of HDAC6 Inhibition

The activities of HDAC 1 and 6 were measured by using an acetylated-AMC-labeled peptide substrate, a fluorogenic peptide from p53 residues 379-382 (RHKKAc). The proteins involved in the assay are as the followings (1) Human HDAC1 (GenBank Accession No. NM_004964): Full length with C-terminal GST tag, MW=79.9 kDa, expressed by baculovirus expression system in Sf9 cells; and (2) Human HDAC6 (GenBank Accession No. BC069243): Full length with N-terminal GST tag, MW=159 kDa, expressed by baculovirus expression system in Sf9 cells.

Table 11 Compounds shows high selectivity of HDAC6 inhibition and superior pharmacological properties

TABLE II

| Compound No. | HDAC1 $IC_{50}$ (A) (nM) | HDAC6 $IC_{50}$ (B) (nM) | HDAC6 selectivity (A)/(B) | Oral Cmax (ng/mL) | AUC |
|---|---|---|---|---|---|
| 1 | 3940 | 12 | 328 | 4132 | 5834 |
| 2 | 5170 | 2 | 2585 | 1152 | 12519 |
| 6 | 5100 | 60 | 85 | 3632 | 42612 |
| 11 | 6900 | 159 | 43 | 727 | 7178 |
| 22 | 4240 | 55 | 77 | 3333 | 9916 |
| 26 | 4320 | 24 | 180 | 2685 | 11961 |
| 33 | 4440 | 33 | 134 | 2723 | 11001 |
| 34 | 4550 | 26 | 175 | 873 | 10982 |
| 44 | 2580 | 20 | 129 | 719 | 5717 |
| J22214 | 1940 | 8 | 243 | 258 | 646 |
| J22211 | 3000 | 14 | 214 | 2 | 2 |
| J17374 | 2090 | 32 | 65 | 307 | 1182 |

Example 76: Compound 2 Alleviated Paclitaxel-Induced Peripheral Neuropathy

Male Sprague-Dawley (SD) rats, weighing 320±30 grams, were given paclitaxel intraperitoneally at the dose of 6 mg/kg for 5 consecutive days with a total cumulative dose of 30 mg/kg to induce chemotherapy-induced peripheral neuropathy.

Compound 2 or vehicle was administered orally once daily for 2 weeks during the weekdays (Days 8 to 12 and 15-19). Mechanical allodynia is assessed by the manual Von Frey test once per week. The animals are given 20 to 30 minutes to acclimatize prior to the testing. The paw is pressed with a series of 8 manual Von Frey monofilaments with logarithmically incremental stiffness [3.61 (0.4 g), 3.84 (0.6 g), 4.08 (1.0 g), 4.31 (2.0 g), 4.56 (4.0 g), 4.93 (8.0 g), 5.18 (15.0 g) and (26.0 g)]. The manual Von Frey monofilament was applied perpendicularly from underneath the mesh floor to the central plantar surface with sufficient force to cause a slight buckling against the paw, and held for approximately 6-8 seconds. A positive response was noted if the paw is sharply withdrawn; ambulation is considered an ambiguous response, and in such cases, the stimulus is reapplied. The 50% paw withdrawal threshold (PWT) to a static mechanical stimulus was assessed using Von Frey filament and up-and-down method.

Von Frey data were presented as mean±SEM (Standard Error of the Mean). Treatment groups were compared to the paclitaxel control using Student's T-test. A p value<0.05 is considered to represent a significant difference.

Paclitaxel-treated animals showed a significant decrease in the mean withdrawal force threshold, starting from day 7, compared to the sham animals: 6.22±1.6 g (vehicle group) vs. 25.18±0.49 g (sham group).

Treatment with Pregabalin, a positive control of the transient pain relief, administered one hour prior to Von Frey stimulus test at a dose level of 15 mg/kg resulted in a marked increase in the mean withdrawal force threshold of the treated animals, when compared to the vehicle, starting at study Day 14 (vehicle group, 8.22±2.5 g vs. Pregabalin group 24.1±3.45 g) and Day 21 (vehicle group, 7.75±1.4 g vs. Pregabalin group 26±Og).

Animals treated with Compound 2 showed a significant increase in the threshold of mean withdrawal force, when compared to the vehicle from study Day 14. The Compound 2-related pain-relief was maintained for at least two weeks after dosing was stopped, while Pregabalin failed to show the efficacy (FIG. 7).

Compound 2 at 15 and 30 mg/kg significantly reduced the sensitivity of the treated animals to the mechanical stimulation, starting from study Day 14, and the effect lasted at least for 14 days after the dosing was stopped. The extended duration of pain relief activity suggests that the neurons were restored by Compound 2 treatment.

Figure 7:
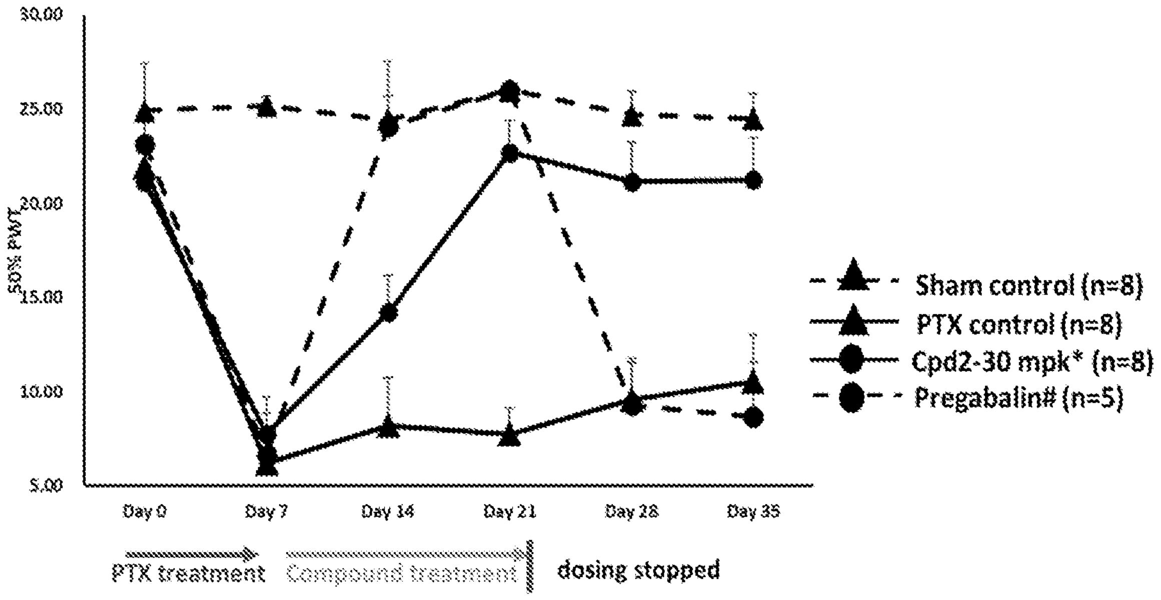
FIG. 7 shows the 50% paw withdrawal threshold (PWT) to a static mechanical stimulus, using Von Frey filaments and the up-and-down method.

FIG. 7 shows the 50% paw withdrawal threshold (PWT) to a static mechanical stimulus, using Von Frey filaments and the up-and-down method.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed:

1. A compound of Formula (I):

Formula (I)

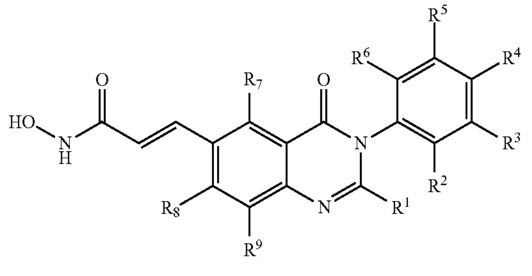

or a pharmaceutically acceptable salt thereof, wherein $R^1$ is methyl or ethyl;
$R^2$ is methyl;
$R^3$ is hydrogen;
$R^4$ is hydrogen;
$R^5$ is hydrogen;
$R^6$ is hydrogen, $(C_{1-3})$alkyl, or halogen;
$R^7$ is hydrogen;
$R^8$ is methyl or fluoro; and
$R^9$ is hydrogen.

2. The compound of claim 1, wherein $R^6$ is methyl or isopropyl.

3. The compound of claim 2, wherein $R^2$ and $R^6$ are each methyl.

4. The compound of claim 3, wherein $R^1$ is ethyl or $R^8$ is fluoro.

5. The compound of claim 1, wherein the compound is of Formula (IB)

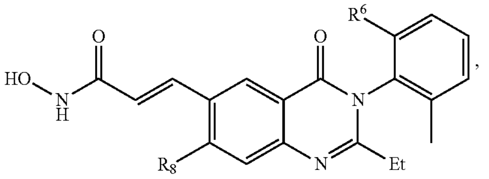

wherein $R^8$ is fluoro.

6. A compound or a pharmaceutically acceptable salt thereof, wherein the compound is selected from:

| Compound No. | Structure |
|---|---|
| 1 | 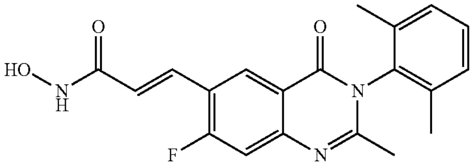 [SMILES: Cc1cccc(C)c1-n1c(C)nc2cc(F)c(/C=C/C(=O)NO)cc2c1=O] |
| 2 | 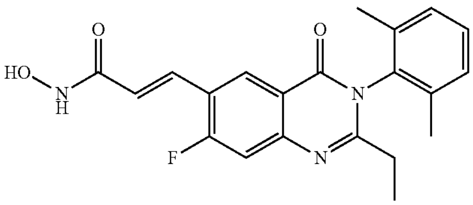 [SMILES: CCc1nc2cc(F)c(/C=C/C(=O)NO)cc2c(=O)n1-c1c(C)cccc1C] |
| 16 | 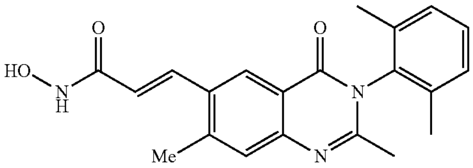 [SMILES: Cc1cc2nc(C)n(-c3c(C)cccc3C)c(=O)c2cc1/C=C/C(=O)NO] |
| 17 | 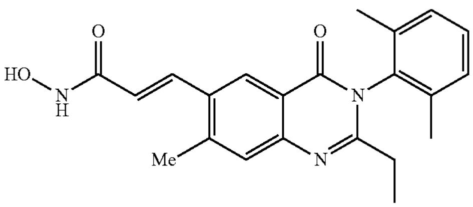 [SMILES: CCc1nc2cc(C)c(/C=C/C(=O)NO)cc2c(=O)n1-c1c(C)cccc1C] |

7. A pharmaceutical composition comprising a therapeutically effective amount of the selective HDAC6 inhibitor (HDAC6i) of claim 6, or a pharmaceutically acceptable salt thereof, and a pharmaceutically acceptable carrier or vehicle.

8. A method for promoting neurite outgrowth in a subject in need thereof, wherein said subject is administered with an effective amount of the selective HDAC6 inhibitor of claim 6, or a pharmaceutically acceptable salt, and a pharmaceutically acceptable carrier or vehicle.

9. A method for the prevention or treatment of peripheral neuropathy, diabetes induced neuropathy, or fibrosis in a subject in need thereof, wherein said subject is administered with effective amount of the selective HDAC6 inhibitor of claim 6, or a pharmaceutically acceptable salt, and a pharmaceutically acceptable carrier or vehicle.

10. The method according to claim 9, wherein said peripheral neuropathy is chemotherapy-induced peripheral neuropathy, diabetic neuropathy, post-herpes zoster pain, or postherpetic neuralgia from shingles.

11. A method for enhancing tubulin hyperacetylation of cells in a subject, wherein said subject is treated with effective amount of the selective HDAC6 inhibitor of claim 6, or a pharmaceutically acceptable salt thereof, and a pharmaceutically acceptable carrier or vehicle.

12. A method of decreasing expression of IL-1, TNF-α, IL-6 or Collagens in a subject in need thereof, wherein said subject is administered with effective amount of the selective HDAC6 inhibitor of claim 6, or a pharmaceutically acceptable salt, and a pharmaceutically acceptable carrier or vehicle.

13. A method of treating or ameliorating cytokine-induced inflammatory conditions in a subject in need thereof, wherein said cytokine comprises IL-1, TNF-α, IL-6, M-CSF, VCAM-1, or MCP-1, and said subject is administered with effective amount of the selective HDAC6 inhibitor of claim 6, or a pharmaceutically acceptable salt, and a pharmaceutically acceptable carrier or vehicle.

14. The method according to claim 10, wherein:

said chemotherapy is platinum-based chemotherapy, alkaloid-based, or taxane-based chemotherapy;

said peripheral neuropathy is chemotherapy-induced peripheral neuropathy; and said fibrosis is pulmonary fibrosis, hepatic fibrosis, or renal fibrosis.

15. The method according to claim 14, wherein said pulmonary fibrosis is associated with increased expression of IL-1, TNF-α, IL-6 or Collagens in said subject.

16. The method according to claim 14, wherein said pulmonary fibrosis is idiopathic pulmonary fibrosis or virus-induced fibrosis.

17. The method according to claim 13, wherein said conditions are selected from a group consisting of coronavirus-induced pulmonary inflammation, acute respiratory distress syndrome, acute pulmonary inflammation, pulmonary fibrosis, liver fibrosis, and renal fibrosis.

* * * * *